US008309086B2

(12) United States Patent
Jacquemin et al.

(10) Patent No.: US 8,309,086 B2
(45) Date of Patent: *Nov. 13, 2012

(54) ANTIBODIES WHICH BIND FACTOR VIII

(75) Inventors: Marc G. Jacquemin, Sart-Bernard (BE); Jean-Marie R. Saint-Remy, Grez-Doiceau (BE)

(73) Assignee: Life Sciences Research Partners VZW, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/779,399

(22) Filed: May 13, 2010

(65) Prior Publication Data

US 2010/0285021 A1    Nov. 11, 2010

Related U.S. Application Data

(63) Continuation of application No. 11/298,560, filed on Dec. 9, 2005, now Pat. No. 7,829,085, which is a continuation-in-part of application No. 10/030,522, filed as application No. PCT/EP00/06677 on Jul. 13, 2000, now Pat. No. 7,067,313, said application No. 11/298,560 is a continuation-in-part of application No. PCT/BE2004/000118, filed on Aug. 16, 2004.

(60) Provisional application No. 60/143,891, filed on Jul. 14, 1999.

(30) Foreign Application Priority Data

| Jul. 14, 1999 | (GB) | 9916450.1 |
| Aug. 14, 2003 | (GB) | 0319118.6 |
| Aug. 18, 2003 | (GB) | 0319345.5 |

(51) Int. Cl.
*A61K 39/395* (2006.01)

(52) U.S. Cl. ............... 424/139.1; 424/133.1; 424/141.1; 424/145.1; 514/14.1

(58) Field of Classification Search .................. None
See application file for complete search history.

(56) References Cited

U.S. PATENT DOCUMENTS

| 4,451,454 | A |  | 5/1984 | Wong |
| 5,545,403 | A |  | 8/1996 | Page |
| 5,545,404 | A |  | 8/1996 | Page |
| 5,545,405 | A |  | 8/1996 | Page |
| 5,602,015 | A |  | 2/1997 | Sudhir |
| 5,714,350 | A |  | 2/1998 | Co et al. |
| 5,744,446 | A |  | 4/1998 | Lollar et al. |
| 6,005,091 | A |  | 12/1999 | Blackburn et al. |
| 6,127,337 | A |  | 10/2000 | Konishi et al. |
| 6,210,675 | B1 |  | 4/2001 | Highfield et al. |
| 6,881,408 | B1 |  | 4/2005 | Heinrich et al. |
| 6,984,649 | B1 |  | 1/2006 | Murata et al. |
| 6,989,401 | B2 |  | 1/2006 | Maeda et al. |
| 7,008,962 | B2 |  | 3/2006 | Palovich et al. |
| 7,067,313 | B1 | * | 6/2006 | Jacquemin et al. ......... 435/326 |
| 7,214,785 | B2 |  | 5/2007 | Nakashima et al. |
| 7,785,594 | B2 | * | 8/2010 | Saint-Remy et al. ...... 424/145.1 |
| 7,829,085 | B2 |  | 11/2010 | Jacquemin et al. |
| 2001/0018052 | A1 |  | 8/2001 | Feuerstein |
| 2002/0182208 | A1 |  | 12/2002 | Page et al. |
| 2003/0035799 | A1 |  | 2/2003 | Page et al. |
| 2003/0175268 | A1 |  | 9/2003 | Saint Remy et al. |
| 2004/0120951 | A1 |  | 6/2004 | Nakashima et al. |
| 2004/0228857 | A1 |  | 11/2004 | Page et al. |
| 2006/0115474 | A1 |  | 6/2006 | Jacquemin et al. |
| 2006/0292149 | A1 |  | 12/2006 | Saint Remy et al. |
| 2008/0206254 | A1 |  | 8/2008 | Jacquemin et al. |
| 2010/0266586 | A1 |  | 10/2010 | Saint-Remy et al. |
| 2010/0272715 | A1 |  | 10/2010 | Saint-Remy et al. |
| 2010/0285021 | A1 |  | 11/2010 | Jacquemin et al. |
| 2011/0070226 | A1 |  | 3/2011 | Saint-Remy et al. |

FOREIGN PATENT DOCUMENTS

| EP | 0 822 255 | 2/1998 |
| EP | 1222929 A | 7/2002 |
| EP | 1396539 A | 3/2004 |
| EP | 1706079 A | 10/2006 |
| EP | 1194528 B1 | 3/2007 |
| EP | 1910420 | 4/2008 |
| WO | WO 96/27010 A1 | 9/1996 |
| WO | WO 97/26010 | 7/1997 |
| WO | WO 99/58680 | 11/1999 |
| WO | WO 01/04269 | 1/2001 |
| WO | WO 02/101040 | 12/2002 |
| WO | WO 03/048328 A2 | 6/2003 |
| WO | WO 2005/016455 | 2/2005 |
| WO | WO 2005/046583 | 5/2005 |
| WO | WO 2007/017154 | 2/2007 |

OTHER PUBLICATIONS

Algiman et al (1992), "Natural antibodies to factor VIII (antihemophilic factor) in healthy individuals", Proc. Natl. Acad. Sci. U. S. A 89, 3795-3799.

Amit et al (1986), "Three-dimensional structure of an antigen-antibody complex at 2.8 A resolution", Science 233, 747-753.

Batlle et al (1997), "Alloantibody from a patient with severe von Willebrand disease inhibits von Willebrand factor-FVIII interaction", Ann. Hematol. 75, 111-115.

Beers (1999), "Bacteremia and septic shock In The Merck Manual of Diagnosis and Therapy", M.H.Beers and R.Berkow, eds. Merck Research Laboratories), pp. 1143-1147.

Begany (2000), "Monoclonal Antibodies improves sepsis", Pulmonary Reviews.__com 5. No. 8.

Campbell (1984), "General properties and applications of monoclonal antibodies In Laboratory Techniques in Biochemistry and Molecular Biology. Monoclonal Antibody Technology", R.H. Burdon and P.H.Knippenberg, eds. (Amsterdam: Elsevier Science Publishers), pp. 1-4.

(Continued)

*Primary Examiner* — Michael Szperka
(74) *Attorney, Agent, or Firm* — Nixon & Vanderhye P.C.

(57) ABSTRACT

The invention, in general, features a method of treatment and/or prevention of a thrombotic pathological condition, in a mammal, which includes administering to the mammal in need of such treatment a therapeutically effective amount of a composition including an antibody directed against the C1 domain of Factor VIII, which is a partially inhibitory antibody of Factor VIII.

2 Claims, 19 Drawing Sheets

OTHER PUBLICATIONS

Cobb (1984), "Septic polyarthritis in a hemophiliac", J. Rheumatol. 11, 87-89.
Davies et al (1996), "Affinity improvement of single antibody VH domains: residues in all three hypervariable regions affect antigen binding", Immunotechnology. 2, 169-179.
Endo et al (1995), "Glycosylation of the variable region of immunoglobulin G—site specific maturation of the sugar chains", Mol. Immunol. 32, 931-940.
Fay et al (1999), Human inhibitor antibodies specific for the factor VIII A2 domain disrupt the interaction between the subunit and factor IXa, J. Biol. Chem. 274, 29826-29830.
Ferenz et al (1989), "Sepsis due to an infected pseudocyst of hemophilia. A case report", Clin. Orthop. Relat Res. 254-257.
Foster et al (1988), "An immunogenic region within residues Val1670-Glu1684 of the factor VIII light chain induces antibodies which inhibit binding of factor VIII to von Willebrand factor", J. Biol. Chem. 263, 5230-5234.
Freeman et al, (1999), "The role of inflammation in sepsis and septic shock: a meta-analysis of both clinical and preclinical trials of anti-inflammatory therapies", In Inflammation: Basic Principles and Clinical Correlates, J.I.Gallin and R.Snyderman, eds. (Philadelphia: Lippincott Williams & Wilkins), pp. 965-975.
Fukui et al (1981), "Laboratory evidence of DIC under FEIBA treatment of a hemophilic patient with intracranial bleeding and high titre factor VIII inhibitor", Thromb. Res. 22, 177-184.
Fulcher et al (1985), "Human factor VIII procoagulant protein. Monoclonal antibodies define precursor-product relationships and functional epitopes", J. Clin. Invest 76, 117-124.
Gawryl et al (1982), "Inactivation of factor VIII coagulant activity by two different types of human antibodies", Blood 60, 1103-1109.
Gilles et al (1993), "Anti-factor VIII antibodies of hemophiliac patients are frequently directed towards nonfunctional determinants and do not exhibit isotypic restriction", Blood 82, 2452-2461.
Gilles et al (1996), "Neutralizing antiidiotypic antibodies to factor VIII inhibitors after desensitization in patients with hemophilia A", J. Clin. Invest 97, 1382-1388.
Gilles et al (1999),"Antibodies to idiotypes of human monoclonal anti-factor VIII (FVIII) antibodies neutralise their inhibitory activity", Blood 94, 460a.
Gilles et al (1997), "Factor VIII inhibitors", Thromb. Haemost. 78, 641-646.
Gilles et al (1998), "The Arg 2150 His mutation within the factor VIII C1 domain eliminates a B cell epitope that is present only on factor VIII-von Willebrand factor complexes", Blood 92, 710.
Gilles et al (1994), "Healthy subjects produce both anti-factor VIII and specific anti-idiotypic antibodies", J. Clin. Invest 94, 1496-1505.
Healey et al (1995), "Residues 484-508 contain a major determinant of the inhibitory epitope in the A2 domain of human factor VIII", J. Biol. Chem. 270, 14505-14509.
Holt et al (2003), "Domain antibodies: proteins for therapy", Trends Biotechnol. 21, 484-490.
Ingerslev et al (1988), "Applications of immunoperoxidase techniques in specificity testing of monoclonal antibodies (Mabs) against von Willebrand factor (vWf)", Clin Chim. Acta 174, 65-81.
Jacquemin et al (2000), "A human antibody directed to the factor VIII C1 domain inhibits factor VIII cofactor activity and binding to von Willebrand factor", Blood 95, 156-163.
Jacquemin et al (1998), "Mutation ARG2150 -> HIS in the factor VIII C1 domain alters the binding of factor VIII to von Willebrand factor and is responsible for a mild hemophilia A phenotype", Blood 92, 710.
Jacquemin et al (1998), "Mechanism and kinetics of factor VIII inactivation: study with an IgG4 monoclonal antibody derived from a hemophilia A patient with inhibitor", Blood 92, 496-506.
Jacquemin et al (2003), "Glycosylation of a type 2 factor VIII inhibitor determines its maximum level of FVIII inhibition", Blood 102, 163a.
Janeway (1997), "The interaction of the antibody molecule with specific antigen In Immunobiology. The Immune System in Health and Disease", C.A. Janeway, P.Travers, S.Hunt, and M.Walport, eds. Current Biology Ltd. / Garland Publishing Inc.), p. 3:7-3:11.
Janeway (2005), "Germinal center B cells undergo V-region somatic hypermutation,and cells with mutations that improve affinity for antigen are selected in Immunobiology. The Immune System in Health and Disease", C.A.Janeway, P.Travers, S.Hunt, and M.Walport, eds. Garland Science Publishing), pp. 379-381.
Kailas et al (2002), "Epitope specificity of anti-FVIII antibodies during immune tolerance therapy with factor VIII preparation containing von Willebrand factor", Thromb. Res. 107, 291-302.
Kato et al (1993), Activity enhancement of a lung cancer-associated human monoclonal antibody HB4C5 by N-deglycosylation, Hum. Antibodies Hybridomas 4, 9-14.
Kaufman et al (1988), "Synthesis, processing, and secretion of recombinant human factor VIII expressed in mammalian cells", J. Biol. Chem. 263, 6352-6362.
Khurana et al, (1997), "The variable domain glycosylation in a monoclonal antibody specific to GnRH modulates antigen binding", Biochem. Biophys. Res. Commun. 234, 465-469.
Lenting et al (1994), "Identification of a binding site for blood coagulation factor IXa on the light chain of human factor VIII", J. Biol. Chem. 269, 7150-7155.
Lollar et al (1994), "Inhibition of human factor VIIIa by anti-A2 subunit antibodies", J. Clin. Invest 93, 2497-2504.
Lubahn et al (1990), "Characterization of a monoclonal anti-idiotype antibody to human anti-factor VIII antibodies", Proc. Natl. Acad. Sci. U. S. A 87, 8232-8236.
Ly et al (1982), "Characterization of an antibody to factor VIII in a patient with acquired hemophilia with circulating immune complexes", Scand. J. Haematol. 28, 132-140.
Manivel et al (2000), "Maturation of an antibody response is governed by modulations in flexibility of the antigen-combining site", Immunity. 13, 611-620.
Martinell et al (1985), "Peritonitis and septic shock—an evaluation of two experimental models in the rat", Eur. Surg. Res. 17, 160-166.
Muhle et al (2004), "Epitope mapping of polyclonal clotting factor VIII-inhibitory antibodies using phage display", Thromb. Haemost. 91, 619-625.
Near et al (1993), "Characterization of an anti-digoxin antibody binding site by site-directed in vitro mutagenesis", Mol. Immunol. 30, 369-377.
Nystrom (1998), The systemic inflammatory response syndrome: definitions and aetiology, J. Antimicrob. Chemother. *41 Suppl A*, 1-7.
Owens et al (1994), "The genetic engineering of monoclonal antibodies", J. Immunol. Methods 168, 149-165.
Palmer et al (1997), "Identification of novel factor VIII inhibitor epitopes using synthetic peptide arrays", Vox Sang. 72, 148-161.
Peerlinck et al (1999), "Antifactor VIII antibody inhibiting allogeneic but not autologous factor VIII in patients with mild hemophilia A", Blood 93, 2267-2273.
Portolano et al (1993), "Lack of promiscuity in autoantigen-specific H and L chain combinations as revealed by human H and L chain roulette", J. Immunol. 150, 880-887.
Pratt et al (1999), "Structure of the C2 domain of human factor VIII at 1.5 A resolution", Nature 402, 439-442.
Precup et al (1991), "A monoclonal antibody to factor VIII inhibits von Willebrand factor binding and thrombin cleavage", Blood 77, 1929-1936.
Price et al (2004), "Tissue factor and tissue factor pathway inhibitor", Anaesthesia 59, 483-492.
Riedemann et al (2003), "Anti-inflammatory strategies for the treatment of sepsis", Expert. Opin. Biol. Ther. 3, 339-350.
Rudikoff et al (1982), "Single amino acid substitution altering antigen-binding specificity", Proc. Natl. Acad. Sci. U. S. A 79, 1979-1983.
Saenko et al (1999), "Role of the low density lipoprotein-related protein receptor in mediation of factor VIII catabolism", J. Biol. Chem. 274, 37685-37692.
Saint-Remy (2000), "Hemophilia factor VIII therapy. B- and T-cell tolerance: from basic concepts to clinical practice", Haematologica 85, 93-96.
Sato et al (1996), "Humanization of an anti-human IL-6 mouse monoclonal antibody glycosylated in its heavy chain variable region", Hum. Antibodies Hybridomas 7, 175-183.

Scandella et al (1989), "Localization of epitopes for human factor VIII inhibitor antibodies by immunoblotting and antibody neutralization", Blood 74, 1618-1626.

Shima et al (1993), "A factor VIII neutralizing monoclonal antibody and a human inhibitor alloantibody recognizing epitopes in the C2 domain inhibit factor VIII binding to von Willebrand factor and to phosphatidylserine", Thromb. Haemost. 69, 240-246.

Singh et al (2002), "Antithrombotic effects of controlled inhibition of factor VIII with a partially inhibitory human monoclonal antibody in a murine vena cava thrombosis model", Blood 99, 3235-3240.

Declaration of Marc G. Jacquemin, Ph.D. Under 37 CFR § 1.131 dated Sep. 1, 2001.

Wright et al. (1991), EMBO J 10, 2717-2723.

Stoilova-McPhie et al. (2002), Blood 99, 1215-1223.

Van den Brink et al. (2000), Blood 96, 540-545.

Spiegel et al. (2001), Blood 98, 13-19.

Sultan et al. (1987), PNAS 84, 828-831.

Taylor et al. (1997), Blood 89, 4078-4084.

Van den Brink et al. (2002), Blood 99, 2828-2834.

Yan et al. (2004), Nature Medicine 10, 161-167.

Yelton et al. (1995), J Immunol 155, 1994-2004.

Ziegler et al. (1991), New Engl J Med 324, 429-436.

Final Decision rejection JP 509473/2001, mailed Apr. 8, 2008—English translation.

Restriction Requirement U.S. Appl. No. 10/566,851), mailed Dec. 24, 2008.

Office Action EP 02 447 005.6, Jun. 5, 2009.

Office Action CA 2,381,125, May 5, 2009.

Response to Written Opinion issued in PCT/BE2004/000118, dated Apr. 22, 2005.

Chatellier et al, (1995), "Codon-based combinatorial alanine scanning site-directed mutagenesis: design, implementation, and polymerase chain reaction screening", Anal. Biochem. 229, 282-290.

Lenting et al, (1999), "The light chain of factor VIII comprises a binding site for low density lipoprotein receptor-related protein", J. Biol. Chem. 274, 23734-23739.

Saint-Remy et al, (1999), "Anti-idiotypic antibodies:from regulation to therapy of factor VIII inhibitors". Vox Sang. 77 (*Suppl. 1*), 21-24.

Sawamoto et al, (1997), "Anti-factor VIII inhibitor alloantibodies recognizing the A2 domain in the human factor VIII heavy chain poorly bind to porcine factor VIII", Int. J. Hematol. 65, 151-158.

Wilbur et al, (1983), "Rapid similarity searches of nucleic acid and protein data banks", Proc. Natl. Acad. Sci. U. S. A 80, 726-730.

Office Action dated Apr. 26, 2011, issued in connection with U.S. Appl. No. 12/732,556.

The Merck Manual of Diagnosis and Therapy, $17^{th}$ edition, Merck Research Laboratories, 1999, pp. 2816-2819.

Alberts et al, Molecular Biology of the Cell, $3^{rd}$ edition, 1994, pp. 589-591.

Jefferis, R., "Recombinant antibody therapeutics: the impact of glycosylation on mechanisms of action", Trends in Pharmacological Sciences Jul. 2009; 30(7):356-62. Epub Jun. 22, 2009.

International Preliminary Report on Patentability for PCT/BE2004/000118, dated Dec. 2, 2005.

International Search Report for PCT/BE2004/000118, mailed Feb. 2, 2005.

Merck Manual of Diagnosis and Disease, $17^{th}$ Ed., Beers et al (Eds.), Merck Research Laboratories, Whitehouse, NJ, pp. 1143-1147 (1999).

Written Opinion for PCT/BE2004/000118 mailed Feb. 2, 2005.

Office Action issued in connection with U.S. Appl. No. 11/298,560, dated Jul. 30, 2009.

Office Action issued in connection with U.S. Appl. No. 11/298,560, dated Feb. 24, 2010.

Official Communication issued in connection with European Patent Application No. 04 761 479.7, dated Mar. 26, 2010.

Official Communication issued in connection with European Patent Application No. 04 761 479.7, dated May 24, 2011.

Q & A with Amy D. Shapiro, MD, An Overview of Thrombophilia, vol. 6, Issue 5, HEMAWARE, pp. 13-16 (2001).

* cited by examiner

BO2C11 Variable heavy chain (SEQ ID NO: 45 and 46)

```
1/1                                      31/11
atg gac tgg acc tgg agg atc ctc ttc ttg gtg gca gca gct aca ggc acc cac gcc cag
met asp trp thr trp arg ile leu phe leu val ala ala ala thr gly thr his ala gln 61/21                                    91/31
gtc caa ctg gta cag tct ggg gct gag gtg aag aag cct ggg gcc tca gtg aag gtc tcc
val gln leu val gln ser gly ala glu val lys lys pro gly ala ser val lys val ser 121/121                                  151/51
tgc aag gtt tcc gga tac acc ctc act gaa tta ccc gtg cac tgg gtc gga cag gct cct
cys lys val ser gly tyr thr leu thr glu leu pro val his trp val gly gln ala pro
                    ←-----------CDR1----------→

181/61                                   211/71
gga aaa ggg ctt gag tgg gtg gga agt ttt gat cct gaa agt gga gaa tca atc tac gca
gly lys gly leu glu trp val gly ser phe asp pro glu ser gly glu ser ile tyr ala
                        ←---------------------CDR2--------------

241/81                                   271/91
cgg gag ttc cag ggc agc gtc acc atg acc gcg gac aca tct aca gac ata gcc tac atg
arg glu phe gln gly ser val thr met thr ala asp thr ser thr asp ile ala tyr met
-------------------→

301/101                                  331/111
gag ctg agc agc ctg aga tct gac gac acg gcc gtg tat tac tgt gca gtc cct gac cct
glu leu ser ser leu arg ser asp asp thr ala val tyr tyr cys ala val pro asp pro
                                                            ←------------------

361/121                                  391/131
gat gct ttt gat atc tgg ggc caa ggg aca atg gtc acc gtc tct tca gcc tcc acc aag
asp ala phe asp ile trp gly gln gly thr met val thr val ser ser ala ser thr lys
-------CDR3---------→

421/141
ggc cca tcg gtc ttc ccc ctg gga tcc cgt
gly pro ser val phe pro leu gly ser arg
```

Figure 6

BO2C11 Variable light chain (SEQ ID NO: 47 and 48)

```
1/1                                     31/11
atg gaa acc cca gct cag ctt ctc ttc ctc ctg cta ctc tgg ctc cca gat acc acc gga
met glu thr pro ala gln leu leu phe leu leu leu leu trp leu pro asp thr thr gly 61/21                                   91/31
gaa att gcg ttg acg cag tct cca ggc acc ctg tct ttg tct cca ggg gaa aga gcc acc
glu ile ala leu thr gln ser pro gly thr leu ser leu ser pro gly glu arg ala thr 121/41                                  151/51
ctc tcc tgc agg gcc agt cag agt ttt agc agc agc tac tta gcc tgg tat cag cag aaa
leu ser cys arg ala ser gln ser phe ser ser ser tyr leu ala trp tyr gln gln lys
             ←---------------CDR1--------------→

181/61                                  211/71
cct ggc cag gct ccc agg ctc ctc atc tat ggt gca tcc acc agg gcc act ggc atc cca
pro gly gln ala pro arg leu leu ile tyr gly ala ser thr arg ala thr gly ile pro
                                   ←-----CDR2-----→

241/81                                  271/91
gac agg ttc agt ggc agt ggg tct ggg aca gac ttc act ctc acc atc agc aga ctg gag
asp arg phe ser gly ser gly ser gly thr asp phe thr leu thr ile ser arg leu glu 301/101                                 331/111
cct gaa gat ttt gca gtg tat tac tgt cag aag tat ggt acg tca gcg atc acc ttc ggg
pro glu asp phe ala val tyr tyr cys gln lys tyr gly thr ser ala ile thr phe gly
                              ←---------------CD3---------------→

361/121                                 391/131
caa ggg aca cga ctg gag att aaa gga act gtg gct gca cca tct gtc ttc atc ttc ccg
gln gly thr arg leu glu ile lys gly thr val ala ala pro ser val phe ile phe pro 421/141
cca tct
pro ser
```

Figure 7

Krix-1 Variable heavy chain (SEQ ID NO: 1 and 2)

```
1/1                                             31/11
ATG GAC TGG ACC TGG AGG ATC CTC TTC TTG GTG GCA GCA GCC ACA GGA GCC CAC TCC CAG
 M   D   W   T   W   R   I   L   F   L   V   A   A   A   T   G   A   H   S   Q
 <------------------------------ Leader peptide ------------------------------>

61/21                                           91/31
GTG CAA CTG GTG CAA TCT GGG GCT GAG GTG AAG AAG CCT GGG GCC TCA GTG AAG GTC TCC
 V   Q   L   V   Q   S   G   A   E   V   K   K   P   G   A   S   V   K   V   S

121/41                   47    49    151/51
TGC AAG ACC TCT GGA TAC AAC TTC ACC GGC TAC TCT GCT TCT GGA CAT ATC TTC ACC GCC
 C   K   T   S   G   Y   N   F   T   G   Y   S   A   S   G   H   I   F   T   A
                         *     *
                                           <----------------- CDR1 -----------

181/61                                          211/71
TAC TCT GTG CAC TGG GTG CGA CAG GCC CCT GGA CAA GGG CTT GAG TGG ATG GGA AGG ATC
 Y   S   V   H   W   V   R   Q   A   P   G   Q   G   L   E   W   M   G   R   I
 ----------->                                                        <---------

241/81                                          271/91
AAC CCT AAC AGT GGT GCC ACA GAC TAT GCA CAT AAA TTT CAG GGC AGG GTC ACC ATG TCC
 N   P   N   S   G   A   T   D   Y   A   H   K   F   Q   G   R   V   T   M   S
 --------------------- CDR2 --------------------->

301/101                                         331/111
AGG GAC ACG TCC ATC AGC ACA GCC TAC ATG GAA CTG AGC AGG CTG ACA TCT GAC GAC ACG
 R   D   T   S   I   S   T   A   Y   M   E   L   S   R   L   T   S   D   D   T

361/121                                         391/131
GCC ATG TAT TAC TGT GCG AGA GCC GAC AAC TAT TTC GAT ATT GTG ACT GGC TAT ACT TCT
 A   M   Y   Y   C   A   R   A   D   N   Y   F   D   I   V   T   G   Y   T   S
                          <-------------------------- CDR3 ---------

421/141                                         451/151
CAT TAC TTT GAC TAC TGG GGC CGG GGA ACC CTG GTC ACC GTC TCC TCA GCC TCC ACC AAG
 H   Y   F   D   Y   W   G   R   G   T   L   V   T   V   S   S   A   S   T   K
 --------->

481/161
GGC CCA TCG GTC TTC C
 G   P   S   V   F
```

Figure 8

Krix-1 Variable light chain (SEQ ID NO: 3 and 4)

```
1/1                                      31/11
ATG GAA ACC CCA GCT CAG CTT CTC TTC CTC CTG CTA CTC TGG CTC CCA GAT ACC ACC GGA
 M   E   T   P   A   Q   L   L   F   L   L   L   L   W   L   P   D   T   T   G
<------------------------------------ Leader ------------------------------------>

61/21                                    91/31
GAA ATT GTG TTG ACG CAG TCT CCA GGC ACC CTG TCT TTG TCT CCA GGG GAA AGA GCC ACC
 E   I   V   L   T   Q   S   P   G   T   L   S   L   S   P   G   E   R   A   T

121/41                                   151/51
CTC TCC TGC AGG GCC AGT CAG AGT GTT GCC AGC GCC TAC TTA GCC TGG TAC CAG CAA AAA
 L   S   C   R   A   S   Q   S   V   A   S   A   Y   L   A   W   Y   Q   Q   K
                 <---------------------- CDR1 ---------------------->

181/61                                   211/71
CCT GGC CAG GCT CCC AGG CTC CTC ATC TAT GGT GCA TCC AGT AGG GCC ACC GAC ATC CCA
 P   G   Q   A   P   R   L   L   I   Y   G   A   S   S   R   A   T   D   I   P
                                     <---------- CDR2 ---------->

241/81                                   271/91
CAC AGG TTC AGT GGC AGT GGG TCT GGG ACA GAC TTC ACT CTC ACC ATC AGC AGA CTG GAG
 H   R   F   S   G   S   G   S   G   T   D   F   T   L   T   I   S   R   L   E

301/101                                  331/111
CCT GAA GAT TTT GCA GTG TAC TAC TGT CAG CAA TAT GGT ACC TCA GCC TTA CTC ACT TTC
 P   E   D   F   A   V   Y   Y   C   Q   Q   Y   G   T   S   A   L   L   T   F
                                 <---------------------- CDR3 ---------------------->

361/121                                  391/131
GGC GGA GGG ACC AAG GTG GAG ATC AAA CGA ACT GTG GCT GCA CCA TCT GTC TTC ATC TTC
 G   G   G   T   K   V   E   I   K   R   T   V   A   A   P   S   V   F   I   F

421/141
CCG CCA TCT
 P   P   S
```

Figure 9

RHD5 heavy chain variable region (SEQ ID NO: 29 and 30)

```
1/1                                     31/11
ATG GAC TGG ACC TGG AGG TTC CTC TTT GTG GTG GCA GCA GCT GCA GGT GTC CAG TCC CAG
 M   D   W   T   W   R   F   L   F   V   V   A   A   A   A   G   V   Q   S   Q
<----------------------------------- Leader peptide ----------------------------------->
61/21                                   91/31
GTG CAG CTG GTG CAG TCT GGG GCT GAG GTG AAG AAG CCC GGG TCG TCG GTG ATG GTC TCC
 V   Q   L   V   Q   S   G   A   E   V   K   K   P   G   S   S   V   M   V   S 121/41                                  151/51
TGC AAG GCT TCT GGA GGC ACC TTC AGC AGC TTT GGT ATC AGC TGG GTG CGA CAG GCC CCT
 C   K   A   S   G   G   T   F   S   S   F   G   I   S   W   V   R   Q   A   P
                                  <------------------ CDR1 ------------------>

181/61                                  211/71
GGA CAA GGG CTT GAG TGG GTG GGA GGG ATC ATC CCT ATC TTT GGT ACA GCA AAC ACC GCA
 G   Q   G   L   E   W   V   G   G   I   I   P   I   F   G   T   A   N   T   A
                                  <--------------------------------- CDR2 ------

241/81                                  271/91
CAG AAC TTC CAG AAT AGA GTC ACC ATT ACC GCG GAC GAA TTC ACG AGC ACA GCC TAC ATA
 Q   N   F   Q   N   R   V   T   I   T   A   D   E   F   T   S   T   A   Y   I
--------------------->

301/101                                 331/111
CGA CTG AGG AGC CTG AGA TCT GAA GAT ACG GCT GTG TAT TAC TGT GTC GGC GGT GGA GAT
 R   L   R   S   L   R   S   E   D   T   A   V   Y   Y   C   V   G   G   G   D
                                                                <-----------

361/121                                 391/131
GCC TAC AGC TTT GAT GGT TTT GAT GTC TGG GGC CAA GGG ACA ATG GTC ACC GTC TCT TCA
 A   Y   S   F   D   G   F   D   V   W   G   Q   G   T   M   V   T   V   S   S
---------- CDR3 ------------------>

421/141
GCC TCC ACC AAG GGC CCA TCG GTC TTC CCC
 A   S   T   K   G   P   S   V   F   P
<------------constant region----------->
```

Figure 14

RHD5 Light Chain Variable Region ( SEQ ID NO: 31 And 32)

```
1/1                                     31/11
ATG GCA TGG ATC CCT CTC TTC CTC GGC GTC CTT GTT TAC TGC ACA GGA TCC GTG GCC TCC
 M   A   W   I   P   L   F   L   G   V   L   V   Y   C   T   G   S   V   A   S
<------------------------------- Leader peptide ------------------------------->

61/21                                   91/31
TCT GGG CTG ACT CAG CCA CAC TCA GTG TCC GTG TCC CCA GGA CAG ACA GCC AAC ATC ACC
 S   G   L   T   Q   P   H   S   V   S   V   S   P   G   Q   T   A   N   I   T
                                                                     *       *

121/41                                  151/51
TGC TCT AGA GAT AAG TTG GGT CAT AAA TTT GCT TCC TGG TAT CAA CAG AAG CCA GGC CAG
 C   S   R   D   K   L   G   H   K   F   A   S   W   Y   Q   Q   K   P   G   Q
         <------------------- CDR1 ------------------>

181/61                                  211/71
TCC CCT GCT CTT CTC ATC TAT CAA GAC AGC AAG CGG CCC TCA GGG ATC CCT GAG CGA TTC
 S   P   A   L   L   I   Y   Q   D   S   K   R   P   S   G   I   P   E   R   F
                         <----------- CDR2 ----------->

241/81                                  271/91
TCT GGC TCC AAC TCT GGG AAC ACA GCC ACT CTG ACC ATC AGC GGG ACC CAG GCT ATG GAT
 S   G   S   N   S   G   N   T   A   T   L   T   I   S   G   T   Q   A   M   D

301/101                                 331/111
GAG GCT GAC TAT TAC TGT CAG GCG TGG GAC AAC ACC ACT GCC GTA TTC GGC GGA GGG ACC
 E   A   D   Y   Y   C   Q   A   W   D   N   T   T   A   V   F   G   G   G   T
                         <------------------ CDR3 ------------------>
                                                 *       *

361/121                                 391/131
AAG TTG ACA GTC CTA AGT CAG CCC AAG GCT GCC CCC TCG GTC ACT CTG TTC CCG CCC TCC
 K   L   T   V   L   S   Q   P   K   A   A   P   S   V   T   L   F   P   P   S
                         <----------------constant region----------------
```

Figure 14 (continued)

DEG = Deglycosylated KRIX-1    NAT = Native KRIX-1

ANTIBODIES WHICH BIND FACTOR VIII

CROSS-REFERENCE TO RELATED APPLICATIONS

This application is a continuation of U.S. application Ser. No. 11/298,560, filed Dec. 9, 2005 now U.S. Pat. No. 7,829,085 (published as US 2006-0115474 A1 on Jun. 1, 2006), which is a continuation-in-part of U.S. application Ser. No. 10/030,522, filed May 2, 2002 (issued as U.S. Pat. No. 7,067,313 on Jun. 27, 2006), which is a U.S. National Stage application of PCT/EP2000/06677, filed Jul. 13, 2000, which, in turn, claims the benefit of U.S. Provisional Patent Application No. 60/143,891, filed Jul. 14, 1999 and British Patent Application No. GB 9916450.1, filed Jul. 14, 1999. Application Ser. No. 11/298,560 is also a continuation-in-part of International Patent Application PCT/BE2004/000118, filed Aug. 16, 2004, which claims the benefit of British Patent Application Nos. GB 0319118.6, filed Aug. 14, 2003 and GB 0319345.5, filed Aug. 18, 2003. The entire contents of each of these patent and patent applications is hereby incorporated by reference in this application.

FIELD OF THE INVENTION

The present invention relates to novel cell lines and to ligands, namely human and/or humanized monoclonal antibodies, as well as fragments such as Fab, Fab', F(ab')$_2$, scFv, single variable domains, complementarily determining regions, derivatives, homologs and combinations thereof, obtainable from the said cell lines. It also relates to pharmaceutical compositions comprising said ligands and to methods of preventing and treating coagulation disorders and resulting thrombotic pathologic conditions in humans by administration of the said ligands to patients in need thereof. It also relates to methods of obtaining specific mammalian antibodies.

BACKGROUND OF THE INVENTION

The formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place. It involves a cascade of complicated and regulated biochemical reactions between circulating blood proteins (coagulation factors), blood cells (in particular platelets) and elements of an injured vessel wall. Anticoagulation and antithrombotic treatment aim at inhibiting the formation of blood clots in order to prevent these dangerous consequences, such as myocardial infarction, stroke, loss of a limb by peripheral artery disease or pulmonary embolism. Given the importance of these diseases, it is rather surprising that antithrombotic therapy relied on a few drugs for many years, namely Aspirin to inhibit platelets, Heparin that indirectly inhibits the coagulation Factors IX, X and II (thrombin), and oral Warfarin that inhibits Vit K-dependent factors (VII, IX, X, II and Prot C). After some time, low molecular weight Heparins (inhibiting Factors X and II to various degrees) became anticoagulants of choice, largely because of their ease of application (once a day subcutaneous injection with no monitoring need). With growing understanding of the processes involved in thrombosis a growing number of specific inhibitors of coagulation factors have been developed. However, a better efficacy/safety ratio could to date not be obtained with them. Direct thrombin inhibitors, in particular, were linked to increased bleeding complications in large clinical trials.

Aspirin also provides a protective effect against thrombosis. It induces a long-lasting functional defect in platelets, detectable clinically as a prolongation of the bleeding time, through inhibition of the cyclooxygenase activity of the human platelet enzyme prostaglandin H-synthase (PGHS-1) with doses as low as 30 to 75 mg. Since gastrointestinal side effects of aspirin appear to be dose-dependent, and for secondary prevention, treatment with aspirin is recommended for an indefinite period, there are practical reasons to choose the lowest effective dose. Further it has been speculated that a low dose (30 mg daily) might be more anti-thrombotic but attempts to identify the optimal dosage have yielded conflicting results. It has been claimed that the dose of aspirin needed to suppress fully platelet aggregation may be higher in patients with cerebrovascular disease than in healthy subjects and may vary from time to time in the same patient. However, aspirin in any daily dose of 30 mg or higher reduces the risk of major vascular events by 20% at most, which leaves much room for improvement.

Further, the inhibiting role of aspirin may lead to prevention of thrombosis as well as to excess bleeding. The balance between the two depends critically on the absolute thrombotic versus hemorrhage risk of the patient.

In patients with acute myocardial infarction, reduction of infarct size, preservation of ventricular function and reduction in mortality has been demonstrated with various thrombolytic agents. However these agents still have significant shortcomings, including the need for large therapeutic doses, limited fibrin specificity, and significant associated bleeding tendency. Recombinant tissue plasminogen activator (t-PA) restores complete patency in just over one half of patients, whereas streptokinase achieves this goal in less than one third. Further, reocclusion after thrombolytic therapy occurs in 5 to 10% of cases during the hospital stay and in up to 30% within the first year according to Verheugt et al., *J. Am. Coll. Cardiol.* (1996) 27:618-627. Thus numerous studies have examined the effects of adjunctive antithrombin therapy for patients with acute myocardial infarction. As an example, U.S. Pat. No. 5,589,173 discloses a method for dissolving and preventing reformation of an occluding thrombus comprising administering a tissue factor protein antagonist, which may be a monoclonal or polyclonal antibody, in adjunction to a thrombolytic agent. Monoclonal antibodies have already been shown to be of therapeutic value as antithrombotic agents. The first approved drug in this field was Abciximab (ReoPro™), a humanized Fab fragment of a murine monoclonal antibody (7E3) against platelet GP IIbIIIa receptors. Murine antibodies have characteristics which may severely limit their use in human therapy. As foreign proteins, they may elicit an anti-immunoglobulin response termed human anti-mouse antibody (HAMA) that reduces or destroys their therapeutic efficacy and/or provokes allergic or hypersensitivity reactions in patients, as taught by Jaffers et al., *Transplantation* (1986) 41:572. The need for readministration in therapies of thromboembolic disorders increases the likelihood of such immune reactions. While the use of human monoclonal antibodies would address this limitation, it has proven difficult to generate large amounts of such antibodies by conventional hybridoma technology.

Recombinant technology has therefore been used to construct "humanized" antibodies that maintain the high binding affinity of murine monoclonal antibodies but exhibit reduced immunogenicity in humans. In particular, chimeric antibodies have been suggested in which the variable region (V) of a non-human antibody is combined with the constant (C)

region of a human antibody. As an example, the murine Fc fragment was removed from 7 E3 and replaced by the human constant immunoglobulin G Fab region to form a chimera known as c7 E3 Fab or abciximab. Methods of obtaining such chimerical immunoglobulins are described in detail in U.S. Pat. No. 5,770,198.

The potential for synergism between GPIIb/IIIa inhibition by monoclonal antibody 7 E3 Fab and thrombolytic therapy was evaluated by Kleiman et al., *J. Am. Coll. Cardiol* (1993) 22:381-389. Major bleeding was frequent in this study. Hence, the potential for life-threatening bleeding is clearly a major concern with this combination of powerful antithrombotic compounds.

Tissue Factor (TF), being a membrane glycoprotein functioning as a receptor for Factor VII and VIIa and thereby initiating the said extrinsic pathway, has been investigated as a target for anticoagulant therapy. In addition to this role, TF has been implicated in pathogenic conditions such as vascular disease and gram-negative septic shock. A study attempting to characterize the anticoagulant potential of murine monoclonal antibodies showed that the inhibition of TF function by most of the monoclonal antibodies assessed was dependent upon the dissociation of the TF/VIIa complex that is rapidly formed when TF contacts plasma. One monoclonal antibody, TF8-5G9, was capable of inhibiting the TF/VIIa complex without dissociation of the complex, thus providing an immediate anticoagulant effect in plasma, as disclosed in WO 96/40,921.

Targeted clotting factors exhibit both a medium molecular weight range (about 45,000 to 160,000) and a relatively high normal plasma concentration (at least 0.01 micromol/L).

One persistent concern with all available anti-thrombotic agents is the risk of overdose and therefore of excessive and life-threatening bleeding. Most current antithrombotic agents therefore warrant close monitoring of the patient.

Thus, there is a need for efficient compounds for the treatment of coagulation disorders, which cannot be overdosed, require no monitoring and are free from bleeding problems. For a therapeutic agent based on antibodies, the ideal compound would be a human antibody with full anticoagulant efficacy that does not induce immunogenicity.

Factor VIII is a protein providing important coagulant cofactor activity and is one of human clotting factors with a rather high molecular weight (265,000) and a very low normal plasma concentration (0.0007 micromol./liter). With its 2,332 amino-acid residues, Factor VIII is one of the longest known polypeptide chains and is synthesized in the liver, the spleen and the placenta. Its gene has been shown to include 186,000 nucleotides.

Factor VIII circulates as inactive plasma protein. Factors V and VIII are homologous proteins sharing a common structural configuration of triplicated A domains and duplicated C domains with structurally divergent B domains connecting the A2 and A3 domains. Factor VIII circulates in a multiplicity of fragmented species in a tightly associated complex with von Willebrand factor at a concentration of 1 nmol/L. Factor VIII activation occurs by a cleavage between the A1 and A2 domains, resulting in the unstable heterotrimeric Factor VIIIa molecule. Factor VIIIa binds tightly to membranes that contain acidic phospholipids. Factor VIII contains a phospholipid binding site in the C2 domain, between amino-acids 2302 and 2332, according to Arai et al. in *J. Clin. Invest.* (1989) 83:1978. Within the same Factor VIII region, there is also a von Willebrand factor binding site acting in conjunction with amino-acid residues 1645-1689 in the A3 domain according to Shima et al. in *Throm. Haemost.* (1993) 69:240 and *J. Biol. Chem.* (1994) 269:11601.[2]

Polyclonal antibodies inhibiting the co-factor activity of Factor VIII have been classified as type I or type II inhibitors according to their capacity to inhibit Factor VIII either completely (type I) or only partially (type II). According to Gawryl et al., *Blood* (1982) 60:1103-9, the reduced inactivation of Factor VIII by human type II autoantibodies is believed to be due to a steric effect of von Willebrand factor. Monoclonal antibodies are not mentioned and, to date, no therapeutic use was made of such type II inhibitors. Biggs et al., *Br. J. Haematol.* (1972) 23:137 previously provided an interpretation derived from data obtained by using human polyclonal antibodies, that a type II inhibitory pattern could be related to low affinity. B. Ly et al., *Scandinavian Journal of Haematology* (1982), 28:132-140 discloses polyclonal antibodies to Factor VIII which most often belong to the IgG class both in hemophiliacs developing alloantibodies and in the more rare patients having autoantibodies against their own Factor VIII. These polyclonal antibodies partially inactivate Factor VIII activity like the antibodies described in Biggs et al. (1972) and Hoyer et al. (1982), This document again fails to mention whether monoclonal antibodies can reproduce the pattern of Factor VIII inactivation shown by patient's polyclonal antibodies. Again, no monoclonal antibodies are mentioned.

European patent applications EP-A-123,945, EP-A-152, 746 and EP-A-432,134 all disclose monoclonal antibodies produced by hybridoma cell lines and having a specific reactivity pattern with Factor VIIIc polypeptide fragments. These monoclonal antibodies are said to be useful for detecting the presence of Factor VIIIc and related polypeptides in plasma by immunoassay techniques, but a therapeutic potential use is not suggested in these documents.

J. Battle et al., *Annals of Hematology* (1997) 75:111-115, discloses a polyclonal alloantibody from a patient with severe von Willebrand disease showing, alike a rabbit polyclonal antibody against von Willebrand factor, a partial inhibitory activity to plasma Factor VIII. These polyclonal anti-Factor VIII antibodies therefore inactivate Factor VIII following a pattern similar to anti-Factor VIII type II antibodies found in patients with hemophilia A (Gawryl et al., *Blood* (1982) 60:1103-9). However, Factor VIII antibodies were not detected in the said human alloantibody, thus suggesting that it was a non-specific inhibition.

J. Ingerslev et al., *Clinica Chimica Acta* (1988) 174:65-82 discloses a series of murine monoclonal antibodies against human von Willebrand factor: two of them, belonging to the immunoglobulin isotype IgG1, exhibit an extremely low (1.3 BU/mg immunoglobulin) inhibition of Factor VIII as shown in table I of said document. By comparison, human monoclonal antibody BO2C11, derived from a hemophilia A patient with inhibitor, has a specific activity of 7,000 BU/mg protein (Jacquemin et al. *Blood*, (1998) 92:496-506). This indicates that administration of antibodies as described by Ingerslev to an animal or a human being would not affect Factor VIII activity, unless an extremely high amount of antibody (hundreds of mg/ml) was present in plasma. The authors do not disclose whether when used in large excess these antibodies exhibit inhibitory activity like type I or type II (i.e. partial inactivation) polyclonal human Factor VIII inhibitor, such as described in Gawryl et al., *Blood* (1982) 60:1103-9.

Maragnore et al., *Circulation* (1992) 86:413, showed that a synthetic 12-aminoacid peptide corresponding to residues 1675-1686 of Factor VIII inhibits cleavage by thrombin of the heavy chain required for the activation of the procoagulant activity of Factor VIII and also of the light chain required to dissociate Factor VIII from von Willebrand factor and that tyrosine sulfation of said peptide potentiates its recognition by Factor VIII.

O'Brien et al., *J. Clin. Invest.* (1988) 82:206-211 describes obtaining an animal model for hemophilia A by infusion of human anti-Factor VIII antibody in rabbits. According to WO 95/01570, antibodies against the light chain of human or porcine Factor VIIIc were produced in a first animal and subsequently a temporary hemophilia was induced in a second animal by means of the purified monospecific antibody obtained. U.S. Pat. No. 5,804,159 also discloses inducing a temporary clotting disorder in a mammal by means of an anti-plasma antibody preparation acting on several blood coagulation factors, e.g. a preparation comprising antibodies against human von Willebrand factor and Factor VIII, or against Factor VIII/von Willebrand factor-complex, or against procoagulants, anticoagulants, clot structure factors, fibrinolysis factors and phospholipids.

However, none of the above-mentioned antibodies compounds involving Factor VIII have been described for therapeutic purposes. In fact there is a prejudice among those skilled in the art against investigating anti-Factor VIII antibodies for anti-thrombotic therapy because it is assumed that, a deficiency in Factor VIII being the cause of hemophilia A, such antibodies would induce a bleeding state.

WO97/26010 discloses monoclonal antibodies having self-limiting neutralizing activity against a coagulation factor which are useful in pharmaceutical compositions for thrombotic disorders. Self-limiting neutralizing activity in this document is defined as the activity of an antibody that binds to a human coagulation factor and inhibits thrombosis in a manner such that limited modulation of coagulation is produced. Limited modulation of coagulation in turn is defined as an increase in clotting time as measured by prolongation of the activated partial thromboplastin time (aPTT) where plasma remains clottable with aPTT reaching a maximal value, preferably 35 to 100 seconds, despite increasing concentrations of the monoclonal antibody. APTT is thus used as the primary criterion for the evaluation of efficacy versus bleeding liability of antithrombotic agents.

More particularly, this document demonstrates that a sheep polyclonal to Factor VIII (SAF8C-IG, purchased from Affinity Biologicals) induces a self-limiting prolongation of aPTT (the aPTT increased to a maximum of about 65 seconds). We have demonstrated, however, that SAF8C-IG totally inhibits the activity of human Factor VIII (see FIG. 10), i.e. is a type I inhibitor in the classification of Gawryl et al., Blood (1982) 60: 1103-9. This demonstrates that a limited increase in clotting time up to a certain maximum value is not necessarily correlated with partial inactivation of a clotting factor, and far less to a decrease in the risk of bleeding. For instance, it is well known that patients with a complete deficit of coagulation factors have a limited prolongation of aPTT, usually in the area of 60 to 100 seconds, but are nevertheless exposed to a dramatic risk of bleeding (Hathaway et al. Am J Clin Pathol (1979) 71: 22-25, and Hoffmann et al. Thromb Haemostas (1978) 39: 640-645).

Conversely, it is well known that a prolonged APTT does not provide a valid parameter of the reduction of thrombosis risk. Notably, deficiency in Factor XII, another coagulation factor of the intrinsic coagulation pathway results in APTT prolonged up to 6-fold (Hathaway et al. Am J Clin Pathol (1979) 71: 22-25, and; Hoffmann et al. Thromb Haemostas (1978) 39: 640-645). However, a significant number of patients with this deficiency have experienced myocardial infarction or thromboembolism, demonstrating the lack of protection from thrombotic disease in patient deficient in Factor XII, despite important prolongation of the APTT (McPherson R A Am J Clin Pathol (1977) 68: 420, and; Glueck H I et al. Ann Intern Med (1966) 64:390).

Jacquemin et al. in *Blood* (1998) 92:496-506 refers to a Factor VIII-specific human IgG4 monoclonal antibody (BO2C11) produced by a cell line derived from the memory B-cell repertoire of a hemophilia A patient with inhibitors. BO2C11 is said to recognize the C2 domain of Factor VIII and to inhibit its binding to both von Willebrand factor and phospholipids. It is said to completely inhibit the procoagulant activity of native and activated Factor VIII with a specific activity of 7,000 Bethesda units/mg. The present inventors have further shown that BO2C11, while totally inhibiting the activity of human Factor VIII, provides a prolongation of about 110 seconds in clotting time as measured by aPTT, which again demonstrates that an increase in clotting time up to a certain maximum value is not necessarily correlated to partial inactivation of a coagulation factor. Such a reduction of Factor VIII levels would expose the patient to severe risks of bleeding, like in patients with severe hemophilia A (Levine P H Ann NY Acad Sci (1975) 240:201; Gilbert M S Mount Sinai J Med (1977) 44: 339).

SUMMARY OF THE INVENTION

The present invention is related to new ligands, namely new monoclonal human or humanized antibodies, fragments, derivatives and homologs thereof, which bind to a factor involved in hemostasis, in particular to a factor or factors of the coagulation cascade and more in particular bind to Factor VIII or a complex thereof. The present invention further provides polypeptides and other molecules which bind to a factor or factors involved in hemostasis. The invention provides novel cell lines from which said monoclonal antibodies may be obtained. The invention provides pharmaceutical compositions comprising the ligands of the invention and methods of prevention and treatment of coagulation disorders and resulting thrombotic pathologic conditions in humans by the administration of said ligands to patients in need thereof.

A first main object of the present invention is therefore to provide an effective and safe anti-thrombotic therapy which reduces the risk of bleeding in mammals, more particularly in humans.

It is a further object of this invention to provide therapeutic compositions which provide an effective anti-thrombotic therapy which reduces the risk of bleeding in mammals, more particularly in humans.

It is still a further object of the present invention to provide an anti-thrombotic therapy and anti-thrombotic therapeutic compounds which are safer to use than the previously known therapies and compositions.

One aspect of the present invention is to target a human protein factor involved in hemostasis, in particular in the coagulation cascade, more particularly Factor VIII or a complex thereof, using specific inhibitory ligands. Preferably, these ligands, being other than polyclonal antibodies, provide a therapeutically useful plateau level of inhibition by only partially inhibiting the function of the targeted factor so that a residual activity of the factor remains, even when the ligand is used in a molar excess. A curve may be established of the inhibiting effect of a ligand in accordance with the present invention with respect to a certain targeted factor against the concentration of the said ligand and the concentration may be determined at which a minimal residual factor activity still exists which is at least 1%, preferably at least 2%. The residual factor activity at five times this concentration should not be substantially different from the residual activity at the minimal point.

It is especially a further aspect of the present invention to provide high affinity monoclonal antibodies, both human and humanized, as well as fragments, derivatives, and homologs of any of these, having the capacity to only partially inactivate a factor or factors in hemostasis, in particular in the coagulation cascade and more in particular Factor VIII or a complex thereof, even in molar excess of the ligand, thereby preventing the risk of overdosage and the resulting bleeding complications. In a particular embodiment, the present invention provides ligands, more in particular (high affinity and purified) monoclonal antibodies binding to the C1 domain of Factor VIII, both human and humanized antibodies, as well as fragments, derivatives, and homologs of any of these, having the capacity to only partially inactivate Factor VIII.

In a yet more particular embodiment, the invention provides monoclonal antibody Krix-1, obtained from the Krix-1 cell line as deposited with the Belgian Coordinated Collections of micro-organisms, under accession number LMBP 5089CB, as well as fragments, derivatives, and homologs thereof.

In one particular embodiment, the present invention provides monoclonal antibodies binding to the C1 domain of Factor VIII, most particularly antibodies which compete with the binding of the antibody Krix-1 produced by Krix-1 cell line deposited with the Belgian Coordinated Collections of micro-organisms, under accession number LMBP 5089CB to Factor VIII as well as fragments, derivatives, and homologs thereof. Such competition for binding to Factor VIII can be tested with an ELISA as described herein.

In a further particular embodiment, the present invention provides monoclonal antibodies and fragments thereof capable of binding to the C1 domain of Factor VIII and capable of competing with the Krix-1 antibody for the binding to Factor VIII, more particularly binding to the same antigen, most particularly to the same epitope as is bound by the antibody Krix-1.

In another particular embodiment, the present invention provides monoclonal antibodies and fragments thereof binding to the C1 domain of Factor VIII, which are derivatives, more particularly modified versions of the Krix-1 antibody, comprising a variable heavy chain sequence being at least 80% identical to the amino acid sequence depicted in FIG. 8 (SEQ ID NO: 2) and/or a variable light chain sequence being at least 80% identical to the amino acid sequence depicted in FIG. 9 (SEQ ID NO:4). In a particular embodiment, the invention provides monoclonal antibodies and fragments, derivatives and homologs thereof of which the variable heavy chain sequence, respectively light chain sequence, is al least 90%, yet more in particular 95% identical to the amino acid sequence depicted in FIG. 8 (SEQ ID NO: 2), and FIG. 9 (SEQ ID NO: 4), respectively. In another particular embodiment, said monoclonal antibodies binding to the C1 domain of Factor VIII, comprise a variable heavy chain sequence comprising at least one, more in particular two CDRs being at least 80%, more in particular 90% or 95%, identical to the amino acid sequence of one of the CDRs depicted in FIG. 8 and/or a variable light chain sequence comprising at least one, more in particular two, CDRs being at least 80%, more in particular 90% or 95%, identical to the amino acid sequence of the CDRs depicted in FIG. 9. In another particular embodiment, said monoclonal antibodies binding to the C1 domain of Factor VIII, comprise a variable heavy chain sequence comprising CDRs being at least 80%, more in particular 90% or 95%, identical to the amino acid sequence of the corresponding CDRs depicted in FIG. 8 and/or a variable light chain sequence comprising CDRs being at least 80%, more in particular 90% or 95%, identical to the amino acid sequence of the CDRs depicted in FIG. 9. In another particular embodiment, said monoclonal antibodies binding to the C1 domain of Factor VIII or fragments thereof, comprise a sequence comprising one ore more CDR sequences corresponding to SEQ ID NO: 33, SEQ ID NO: 34 and/or SEQ ID NO: 35 (corresponding to the sequence of CDR1, CDR2 and CDR3, respectively of the heavy chain variable region of Krix-1) or a sequence which comprises one ore more CDR sequences corresponding to sequences having at least 80%, more particularly 90%, most particularly at least 95% sequence identity with SEQ ID NO: 33, SEQ ID NO: 34 and/or SEQ ID NO: 35, within the corresponding CDR sequence. Additionally or alternatively, the monoclonal antibodies and fragments thereof according to the present invention comprise a sequence comprising one or more CDR sequences corresponding to SEQ ID NO: 36, SEQ ID NO: 37 and/or SEQ ID NO: 38 (corresponding to the sequence of CDR1, CDR2 and CDR3, respectively of the light chain variable region of Krix-1) or a sequence which comprises one or more CDR sequences having at least 80%, more particularly 90%, most particularly at least 95% sequence identity with SEQ ID NO: 36, SEQ ID NO: 37 and/or SEQ ID NO: 38, within the corresponding CDR sequence.

In a further particular embodiment, the invention provides derivatives of antibodies directed against the C1 domain of Factor VIII, more particularly derivatives of the antibodies described herein, such as but not limited to derivatives of the Krix-1 antibody, which are modified antibodies or modified antibody fragments. Most particularly the modified antibody or antibody fragment is an antibody or fragment with a modified glycosylation, more specifically a modification of the glycosylation in the variable regions of the antibody or fragment, most particularly in one or more of the CDRs of the antibody or antibody fragment, whereby the antibody or fragment still binds Factor VIII and partially inactivates Factor VIII activity. A further particular embodiment of the present invention provides antibodies and fragments which are modified versions of the Krix-1 antibody, which comprise a mutated glycosylation site at one or more of positions Asn47 to Thr49 of the heavy chain variable region. Most particularly the invention provides antibodies and fragments which are modified versions of the Krix-1 antibody, whereby the modifications are selected from the group consisting of heavy chain variable region Asn47 changed to Gln47 (KRIX-1Q), heavy chain variable region Asn47 changed to Glu47 (KRIX-1E) or heavy chain variable region Asn47 changed to Asp47 (KRIX-1D) and/or heavy chain variable region Thr49 changed to Ala49 (KRIX-1A).

In another embodiment, the invention provides monoclonal antibody RHD5, obtained from the cell line as deposited with the Belgian Coordinated Collections of micro-organisms, under accession number LMBP 6165CB, as well as fragments, derivatives, and homologs thereof RHD5 binds to the C1 domain of Factor VIII and only partially inhibits the activity of Factor VIII, namely for 97-98%. The present invention thus relates to the human antibody RHD5, fragments, derivatives and homologs thereof, which bind to Factor VIII, as well as relating to the novel cell line deposited with the Belgian Coordinated Collections of micro-organisms, under accession number LMBP 6165CB, from which RHD5 may be obtained; the invention further provides pharmaceutical compositions comprising said antibody RHD5, fragments, derivatives and homologs thereof and to methods of prevention and treatment of coagulation disorders and resulting thrombotic pathologic conditions in humans by the administration of said RHD5 antibody, fragments, derivatives and homologs thereof, to patients in need thereof.

In one particular embodiment, the present invention provides monoclonal antibodies binding to the C1 domain of Factor VIII, most particularly antibodies which compete with the binding of the antibody RHD5 produced by RHD5 cell line deposited with the Belgian Coordinated Collections of micro-organisms, under accession number LMBP 6165CB to Factor VIII, as well as fragments, derivatives, and homologs thereof Such competition for binding to Factor VIII can be tested with an ELISA as described herein.

In a further particular embodiment, the monoclonal antibodies binding to the C1 domain of Factor VIII of the present invention, are antibodies which bind to the same antigen, more in particular to the same epitope, bound by the antibody RHD5 deposited with the Belgian Coordinated Collections of micro-organisms, under accession number LMBP 6165CB.

In a further particular embodiment, the present invention provides monoclonal antibodies binding to the C1 domain of Factor VIII, and fragments thereof which are derivatives, more particularly modified versions of antibody RHD5, comprising a variable heavy chain sequence being at least 80%, more in particular 90% or 95%, identical to the amino acid sequence depicted in FIG. 14 (SEQ ID NO: 30) and/or a variable light chain sequence being at least 80%, more in particular 90% or 95%, identical to the amino acid sequence depicted in FIG. 14 (SEQ ID NO: 32). In another particular embodiment, said monoclonal antibodies binding to the C1 domain of Factor VIII or fragments thereof, comprise a variable heavy chain sequence comprising at least one, more in particular two CDRs being at least 80%, more in particular 90% or 95%, identical to the amino acid sequence of one of the CDRs of the variable heavy chain depicted in FIG. 14 and/or a variable light chain sequence comprising at least one, more in particular two, CDRs being at least 80%, more in particular 90% or 95%, identical to the amino acid sequence of the CDRs depicted in the variable light chain in FIG. 14. In another particular embodiment, said monoclonal antibodies binding to the C1 domain of Factor VIII and fragments thereof, comprise a variable heavy chain sequence comprising three CDRs being at least 80%, more in particular 90% or 95%, identical to the amino acid sequence of the three CDRs depicted in the variable heavy chain sequence of RHD5 in FIG. 14 and/or a variable light chain sequence comprising CDRs being at least 80%, more in particular 90% or 95%, identical to the amino acid sequence of the three CDRs depicted in the variable light chain sequence of RHD5 in FIG. 14. In another particular embodiment, said monoclonal antibodies binding to the C1 domain of Factor VIII or fragments thereof, comprise a sequence comprising one or more CDR sequences corresponding to SEQ ID NO: 39, SEQ ID NO: 40 and/or SEQ ID NO: 41 (corresponding to the sequence of CDR1, CDR2 and CDR3, respectively of the heavy chain of RHDS) and/or a sequence which comprises one ore more CDR sequences corresponding to sequences having at least 80%, more particularly 90%, most particularly at least 95% sequence identity with SEQ ID NO: 39, SEQ ID NO: 40 and/or SEQ ID NO: 41, within the corresponding CDR sequence. Additionally or alternatively, the monoclonal antibodies and fragments thereof according to the present invention comprise a sequence comprising one ore more CDR sequences corresponding to SEQ ID NO: 42, SEQ ID NO: 43 and SEQ ID NO: 44 (corresponding to the sequence of CDR1, CDR2 and CDR3, respectively of the light chain of RHDS) or a sequence which comprises one or more CDR sequences having at least 80%, more particularly 90%, most particularly at least 95% sequence identity with SEQ ID NO: 42, SEQ ID NO: 43 and/or SEQ ID NO: 44, within each corresponding CDR sequence.

It is still another aspect of the present invention to provide novel cell lines producing the respective monoclonal antibodies disclosed herein. A particular embodiment of the present invention provides cell lines of human monoclonal antibodies capable of binding to the C1 domain of Factor VIII and capable of partially inhibiting Factor VIII activity. A further particular embodiment of this aspect of the present invention provides the Krix-1 cell line as deposited with the Belgian Coordinated Collections of micro-organisms, under accession number LMBP 5089CB and the RHDS cell line, deposited with the Belgian Coordinated Collections of micro-organisms, under accession number LMBP 6165CB.

Yet a further aspect of the present invention provides polynucleotide sequences which encode the antibodies or fragments thereof mentioned above. It will be appreciated that a multitude of nucleotide sequences exist which fall under the scope of the present invention as a result of the redundancy in the genetic code. The present invention also includes complementary sequences to the sequences encoding the monoclonal antibodies, or fragments thereof, mentioned above. In particular, the present invention includes probes constructed from the monoclonal antibodies, or fragments thereof, mentioned above or from the polynucleotides or from the complementary sequences mentioned above. Particular embodiments of the nucleotide sequences provided in accordance with the present invention include the nucleotide sequences encoding the heavy and light chain CDRs of Krix-1, i.e. corresponding to the nucleotide sequences encoding the amino acid sequences provided in SEQ ID Nos 33, 34, 35, 36, 37, and 38. Further particular embodiments of the nucleotide sequences provided in accordance with the present invention include the nucleotide sequences encoding the heavy and light chain CDRs of RHDS, i.e. corresponding to the nucleotide sequences encoding the amino acid sequences provided in SEQ ID Nos 39, 40, 41, 42, 43, and 44. Further embodiments include nucleotide sequences encoding modified versions of the above-mentioned CDRs, which encode a protein capable of binding to Factor VIII and of partially inhibiting Factor VIII activity. More particular embodiments of the present invention include sequences encoding modified versions of the above-mentioned CDRs, which modified versions comprise modifications resulting in the modified glycosylation of the CDRs, more particularly the modified N-glycosylation of the CDRs. Most particular embodiments of the nucleotide sequences of the present invention include sequences encoding a modified version of the Krix-1 antibody or a fragment thereof which comprises a mutated glycosylation site at one or more of positions Asn47 to Thr49 of the heavy chain variable region, most particularly sequences encoding antibodies and fragments thereof which are modified versions of the Krix-1 antibody, whereby the modifications are selected from the group consisting of heavy chain variable region Asn47 changed to G1n47 (KRIX-1Q), heavy chain variable region Asn47 changed to G1u47 (KRIX-1E) or heavy chain variable region Asn47 changed to Asp47 (KRIX-1D) and/or heavy chain variable region Thr49 changed to A1a49 (KRIX-1A).

Yet a another aspect of the present invention provides a method of attenuation of coagulation in humans, comprising administering a ligand, being other than a polyclonal antibody, such as a monoclonal antibody, either human or humanized, a fragment, derivative or homolog thereof, capable of only partially inactivating a factor or factors in hemostasis, in particular in the coagulation cascade and more in particular Factor VIII or a complex thereof to a patient in need of such attenuation even when the said ligand is in a molar excess. It further provides a method of treatment or prevention of a thrombotic pathologic condition in mammals, namely in humans, comprising administering a therapeutically effective amount of a ligand, other than a polyclonal antibody, for instance a monoclonal antibody, either human or humanized, or a fragment, derivative or homolog thereof, capable of only partially inactivating, even when the said ligand is in a molar excess, a factor or factors involved in hemostasis, in particular in the coagulation cascade, and more particularly Factor VIII or a complex including Factor VIII, to a mammal in need of such treatment or prevention. In a preferred embodiment, the thrombotic pathologic condition may be selected for instance from intravascular coagulation, arterial thrombosis, arterial restenosis, venous thrombosis and arteriosclerosis. The methods of treatment and prevention of a thrombotic pathological condition in a mammal of the present invention comprise the administration of one or more of the ligands of the present invention, capable of partially inhibiting Factor VIII, to a mammal in need thereof.

Another aspect of the present invention is directed to providing a composition, more in particular a pharmaceutical composition comprising a ligand, other than a polyclonal antibody, having the capacity of binding to a site on a factor or factors involved in hemostasis, in particular in the coagulation cascade, and more particularly Factor VIII or a complex including Factor VIII, for only partially inactivating the said factor or factor complex even when the ligand is in molar excess, in admixture with a pharmaceutically acceptable carrier. The said ligand preferably is a high affinity anti-Factor VIII or anti-Factor VIII—von Willebrand factor complex monoclonal antibody, either human or humanized, or hybridized, or a fragment, derivative or homolog thereof Particular embodiments of the pharmaceutical compositions provided comprise one or more of the ligands of the present invention described herein, capable of partially inhibiting Factor VIII. The pharmaceutical composition of the present invention may further optionally comprise a therapeutically effective amount of a thrombolytic agent.

Another aspect of the present invention is directed to providing methods for the selection of specific monoclonal antibodies. The conventional technique of immunizing an animal such as a mouse with a protein such as Factor VIII elicits an immunological response which may involve several epitopes on the Factor VIII molecule. The present invention provides more selective methods of obtaining specific monoclonal antibodies against an epitope of a wild-type protein. First, a donor, e.g. a mammal such as a human, is provided (i.e. selected) which has an at least partially functional modified version of a wild-type protein. The modification, which more particularly lies in a domain of the protein of interest, may be due to any cause, e.g. race or variety, to genetic defects at birth, to an illness or by human interference, e.g. immunotolerance against the functionally modified version. The mammal donor is then administered the wild-type protein in order to elicit an immune response; at this stage, it is important that a sufficient quantity of the wild-type protein (e.g. Factor VIII) be administered until an immune response is generated. Then, in a final step of the method, selection of B-cells from the mammal donor will result in a much greater chance of obtaining monoclonal antibodies against an epitope in the region of the modification, for instance by selecting B-lymphocytes from the donor which produce antibodies only partially inactivating the wild type protein.

The anticoagulant potential of inhibiting Factor VIII has to date not been explored, perhaps because of the well known bleeding complications that occur in hemophilia A patients that lack Factor VIII activity completely (severe hemophilia) or to a large extent (moderate hemophilia). Hemophilia A, however, not only demonstrates the importance of Factor VIII as limiting co-factor of coagulation, but also the existing link between coagulation and the development of atherosclerosis. Atherosclerosis and its thrombotic complications were indeed found to be significantly rarer among patients with hemophilia A. Antagonizing Factor VIII activity at a level that allows sufficient hemostasis to prevent bleeding but protects from pathologic intravascular thrombus formation therefore holds substantial promise for safe anticoagulation in prothrombotic diseases such as deep vein thrombosis (DVT), pulmonary embolism (PE), postoperatively, in pregnancy, in coronary artery disease (CAD), cerebrovascular disease (CVD), peripheral artery disease (PAD) and in vascular interventions.

The present invention is based on the surprising determination of new ligands, namely new human and humanized monoclonal antibodies and fragments, derivatives and homologs thereof These may exhibit an unforeseen "plateau effect", i.e. the achievement of only a partial inactivation of a factor involved in hemostasis, in particular in the coagulation cascade, either individually or in combination, whatever the excess of ligand. The ligands may bind to a factor or a complex of factors resulting in only partially impairing the function of a physiologically functional site of the said factor or factor complex. This "plateau effect" makes the ligands particularly suitable for treating coagulation disorders and resulting thrombotic pathologic conditions while minimizing the risk of bleeding, by comparison, notably, to antibodies with self-limiting neutralizing activity mentioned in WO97/26010, There is therefore a sharp contrast between the "the self-limiting neutralizing activity of antibodies to coagulation factors disclosed in WO97/26010 and the clinically meaningful plateau inhibition that the present invention covers, where anti-Factor VIII antibodies such as KRIX-1 inhibit Factor VIII activity by no more than 85% or such as RHD5 inhibit Factor VIII activity by no more than 97-98%.

Particularly useful is a property of ligands in accordance with the present invention to allow some physiological function of the affected target protein even when the ligand is in molar excess. The ligands may be anti-Factor VIII antibodies or antibodies against a Factor VIII complex, in particular human or human hybrid monoclonal antibodies which bind to Factor VIII or a Factor VIII complex and at least partially inhibit the activity of Factor VIII. Data indicate that type II inhibitors react with different antigenic determinants than type I antibodies and that these determinants are partially blocked in the Factor VIII/von Willebrand factor complex.

The present invention will now be described in more details with reference to the following drawings.

BRIEF DESCRIPTION OF THE DRAWINGS

FIG. 1 presents the results of producing human monoclonal antibodies derived from a hemophilia A patient, expressed in the form of IgG antibody binding to Factor VIII in ELISA.

FIG. 2 shows inhibition of Factor VIII activity by the monoclonal antibody BO2C11.

FIG. 3 shows inhibition of Factor VIII activity by the monoclonal antibody produced from the cell line KRIX-1.

FIG. 4 shows inhibition of the binding of activated Factor VIII on phosphatidyl-L-serine by the monoclonal antibody produced from the cell line KRIX-1.

FIG. 5 shows the influence of certain polyclonal antibodies on the dissociation of activated Factor VIII from von Willebrand factor.

FIGS. 6 and 8 show amino acid sequences (the lower lines) and nucleotide sequences (upper lines) for the variable regions $V_H$ of the heavy chains of BO2C11 and the KRIX-1 monoclonal antibodies, respectively. Also shown are the three complementarity determining regions (CDR) of each chain which are each an individual polypeptide ligand in accordance with an individual embodiment of the present invention. (For FIG. 8: Asn and Thr residues of the glycosylation consensus site are indicated with an asterisk).

FIGS. 7 and 9 show amino acid sequences (the lower lines) and nucleotide sequences (upper lines) for the variable regions $V_L$ of the light chains of BO2C11 and the KRIX-1 monoclonal antibodies, respectively. Also shown are the three CDR's of each chain each of which is an individual polypeptide ligand in accordance with particular embodiments of the present invention.

FIG. 10 provides a graph showing inhibition of Factor VIII activity by the antibody SAF8C-Ig mentioned in WO97/26010

Figure 13:
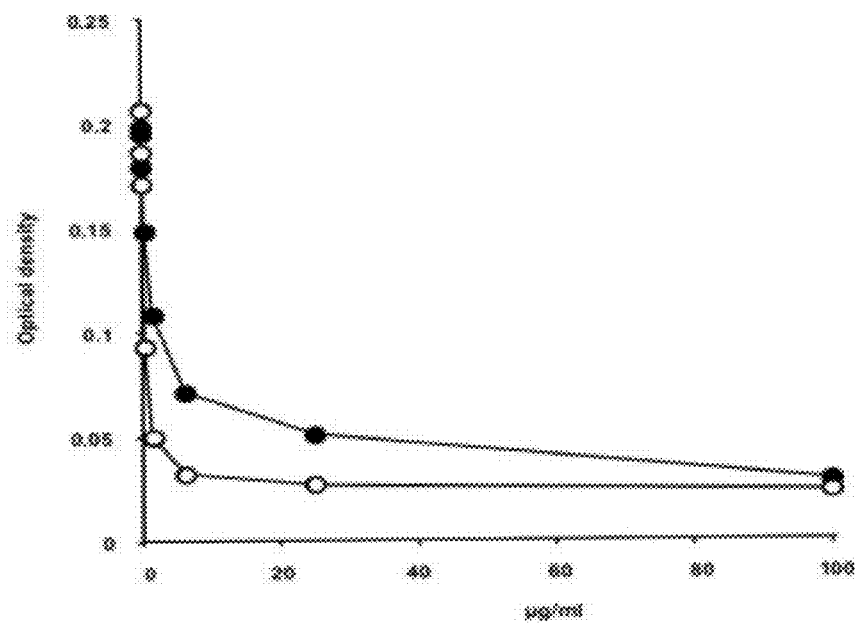

FIG. 13: Graph of experimental results showing the inhibition of Factor VIII binding to RHD5 by Krix-1 and RHD5. Biotinylated recombinant Factor VIII was mixed with different concentrations of RHD5 (closed symbols) or Krix-1 (open symbols) before addition to RHD5 coated plates. The plates were then incubated for 2 hours at 4° C. and the binding of Factor VIII was detected by the addition of avidine peroxidase and OPD.

FIG. 14: nucleotide and amino acid sequence of RHD5 variable heavy and light chain (Asn and Thr residues of putative glycosylation consensus sites are indicated with an asterisk)

Figure 15:
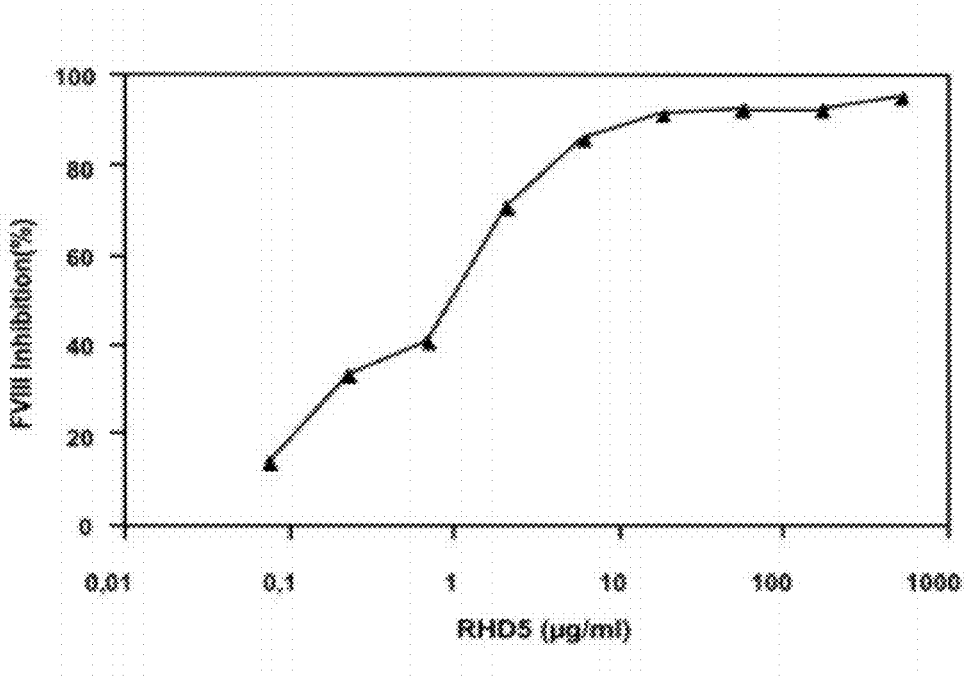

FIG. 15: Inhibition of Factor VIII functional activity in coagulation assays.

Equal volumes of RHD5 and of a pool of normal plasma were incubated for 2 hours at 37° C. RHD5 concentrations before mixing with plasma were as indicated. The residual Factor VIII activity was measured in a chromogenic Factor VIII assay. Results were expressed as the percentage Factor VIII inhibition in presence of RHD5 by comparison with samples treated identically in the absence of RHD5.

Figure 16:
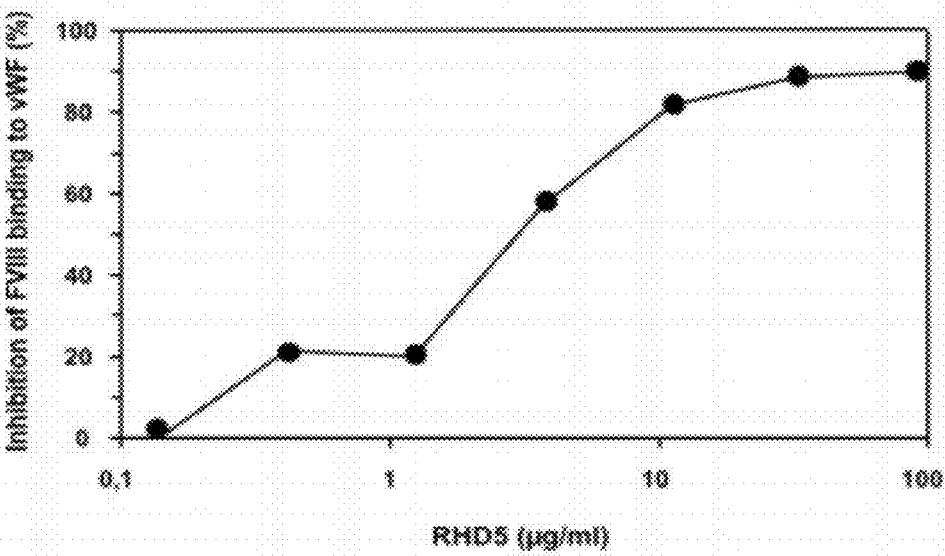

FIG. 16: RHD5 inhibition of Factor VIII binding to vWF. Recombinant biotinylated Factor VIII was mixed with different concentrations of RHD5 before addition to vWF coated plates. The plates were then incubated for 2 hours at room temperature and the binding of Factor VIII was detected by the addition of avidine peroxidase.

Figure 17:
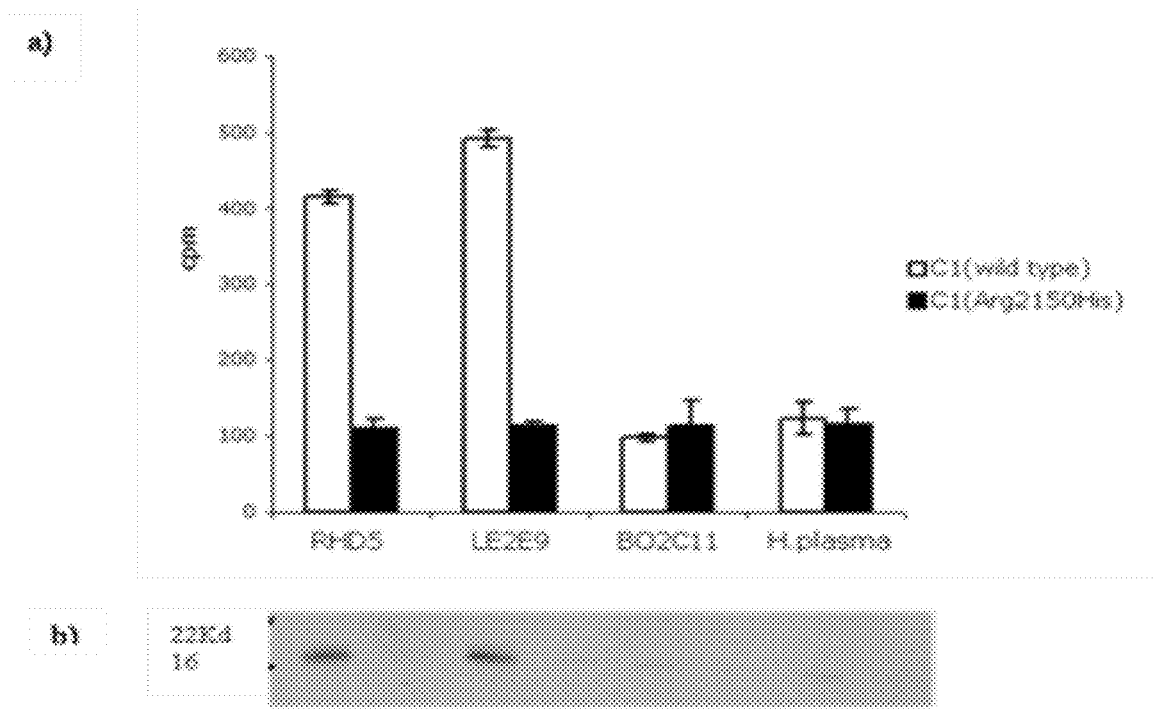

FIG. 17: Epitope mapping of Krix-1 and RHD5 via immunoprecipitation.

Figure 18:
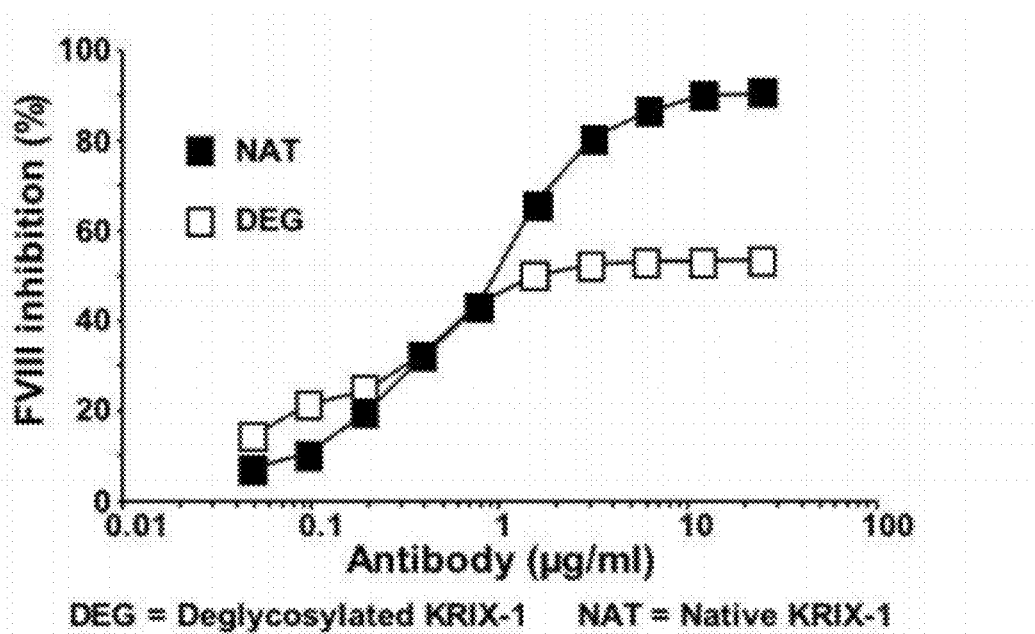

FIG. 18: Graph of experimental results showing the inhibitory activity of native and deglycosylated KRIX-1, in accordance with an embodiment of the invention. KRIX-1 was deglycosylated by treatment with N-glycosidase-F. To assess the inhibitory activity of native (NAT; closed symbol) and deglycosylated KRIX-1 (DEG; open symbol), one volume of antibody at various dilutions was mixed with one volume of a pool of normal human plasma and incubated for 2 h at 37° C. The residual Factor VIII activity was then measured in a chromogenic assay.

Figure 19:
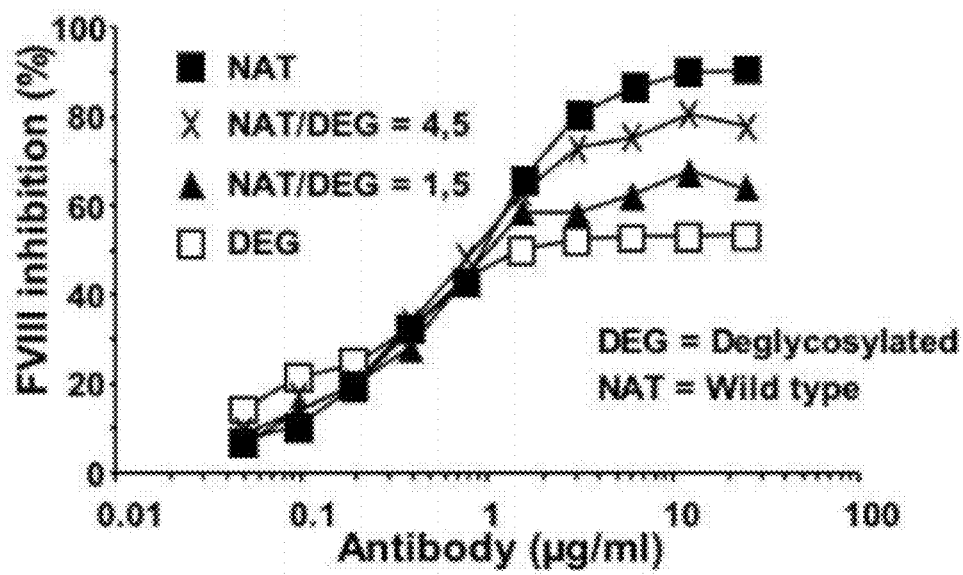

FIG. 19: Graph of experimental results showing that mixing deglycosylated KRIX-1 with native KRIX-1 reduces the maximal "plateau" inhibition of Factor VIII, in accordance with an embodiment of the invention. Normal plasma was incubated for 2 h at 37° C. with various concentrations of Krix-1, deglycosylated Krix-1, and mixtures of native and deglycosylated Krix-1 at a ratio of 4.5 and 1.5 native versus deglycosylated antibody. After a 2h incubation period at 37° C., the residual Factor VIII activity was measured in a Factor VIII chromogenic assay.

Figure 20:
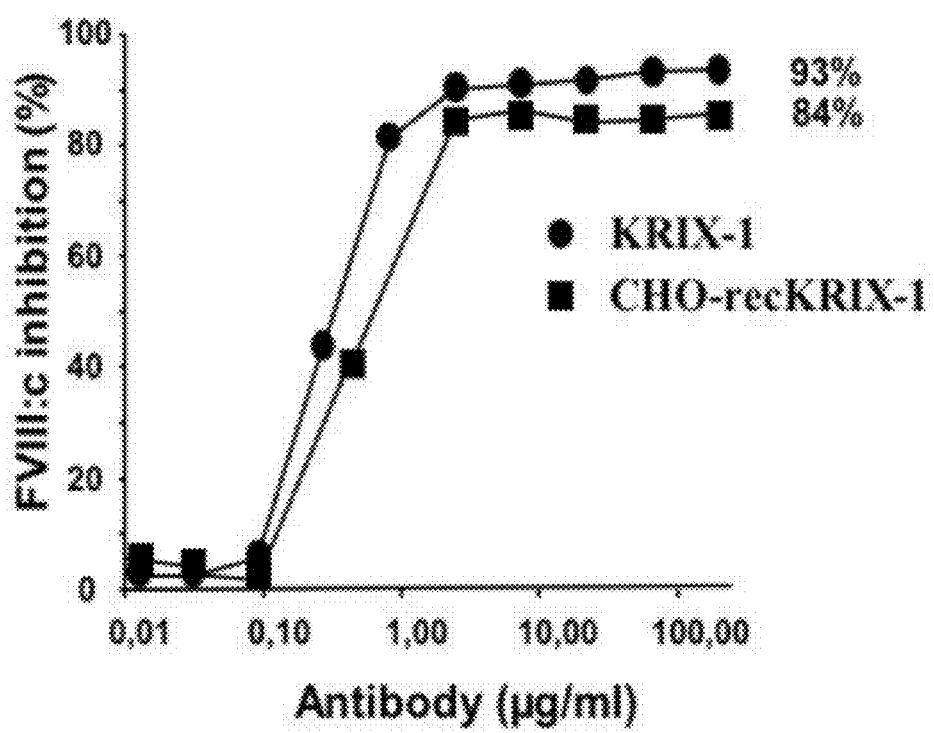

FIG. 20: Graph of experimental results showing the inhibitory activity of CHO-recKRIX-1 and KRIX-1 on Factor VIII activity in plasma, in accordance with an embodiment of the invention. To assess the inhibitory activity of the antibody produced by the human cell line (KRIX-1) and the recombinant antibody produced in CHO (CHO-recKRIX-1), one volume of antibody at various dilutions was mixed with one volume of a pool of normal human plasma and incubated for 2 h at 37° C. The residual Factor VIII activity was then measured in a chromogenic assay.

Figure 21:
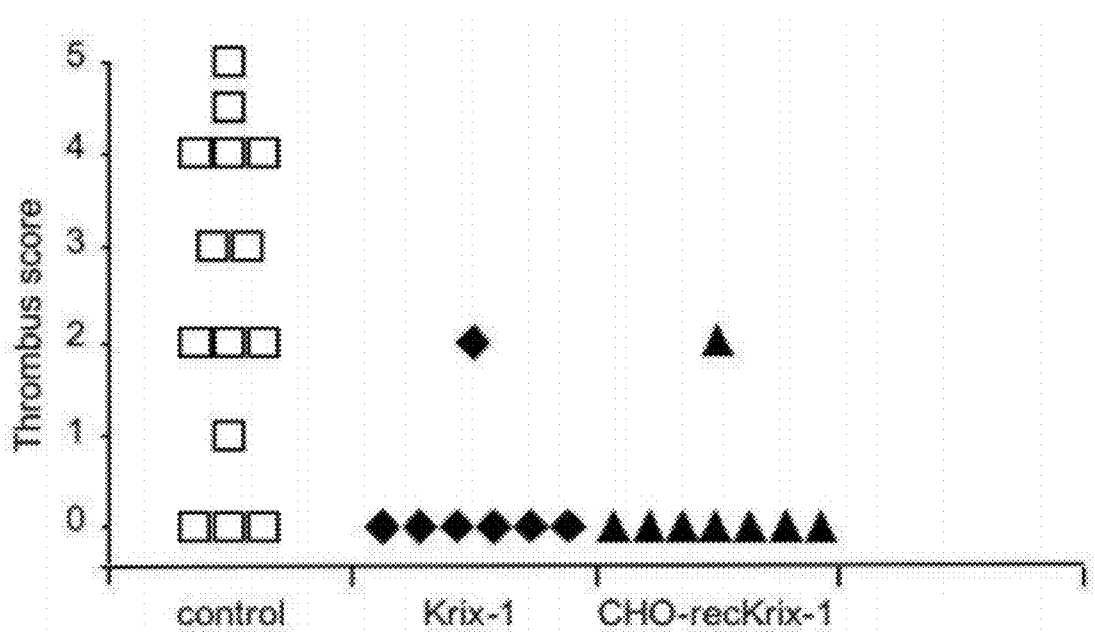

FIG. 21: Graph of experimental results showing the effect of KRIX-1 and CHO-recKRIX-1 on vena cava thrombosis in mice, in accordance with an embodiment of the invention. Thrombus was induced in the inferior vena cava 16 hours after subcutaneous administration of 150 microgram KRIX-1 and CHO-recKRIX-1 or saline. Animals were sacrificed after 4 hours. Five transverse segments at 0.5 mm intervals through the infrarenal vena cava were scored 1 if thrombus was present or zero if absent, and the scores were summed.

Figure 22:
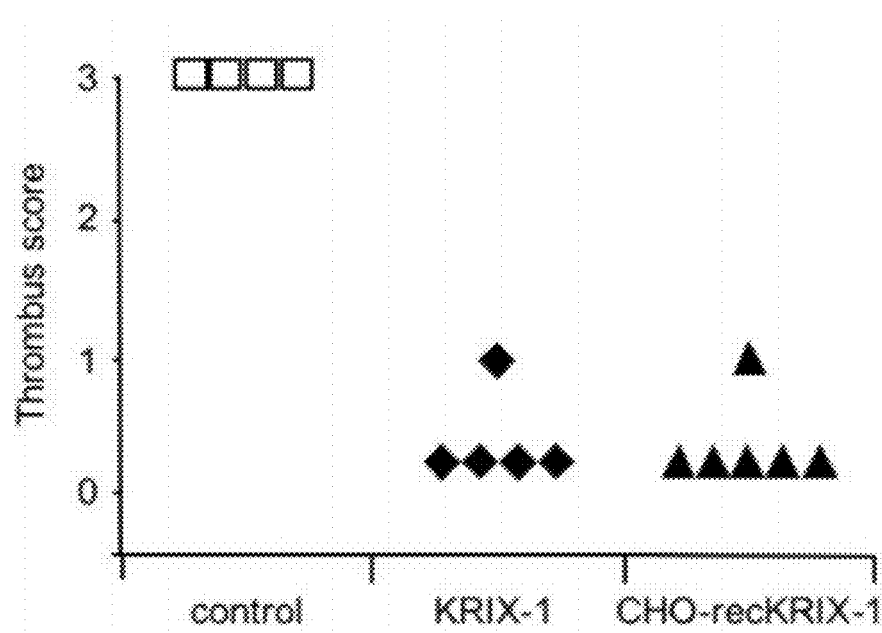

FIG. 22: Graph of experimental results showing that KRIX-1, CHO-rec-KRIX-1 protect against penile thrombosis and priapism in mated $AT^{m/m}$ males, in accordance with an embodiment of the invention. Males were injected twice subcutaneously with vehicle (PBS), or with 100 microgram antibody mAb Krix-1 or rec-mAB Krix-1, three days before and on the day of mating. Thrombotic outcome was scored zero if the mice were free of thrombosis at the end of the 8-day follow-up, 1 if microscopic thrombosis without priapism was observed, 2 if macroscopic thrombosis without priapism occurred, and 3 if the males developed severe thrombosis with irreversible priapism. (#) One mouse each in the mAb Krix-1 or rec-mAb Krix-1 treated group was free of macroscopic thrombosis at the end of the experiment but could not be analyzed by microscopy and were therefore scored 1.

Figure 23:
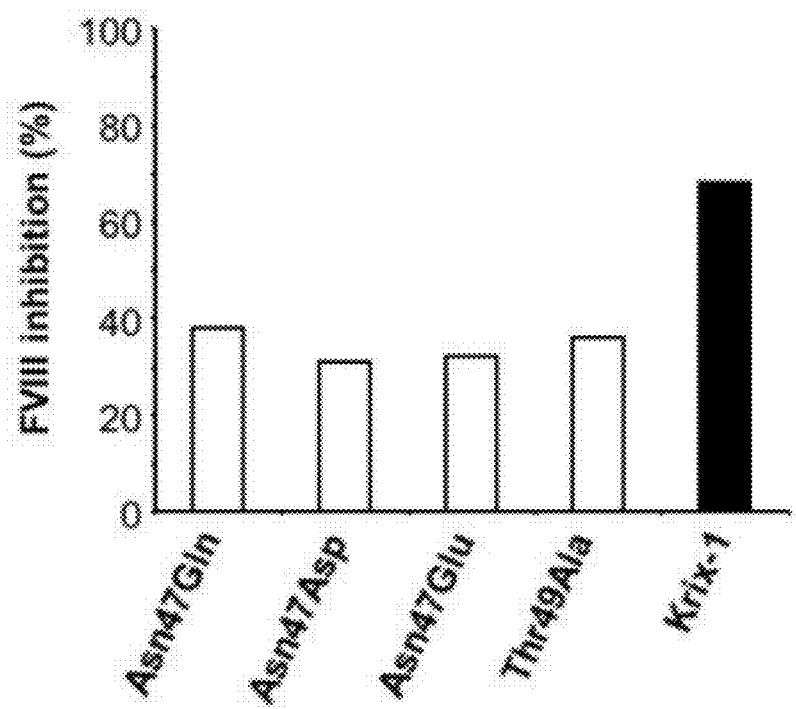

FIG. 23: Graph of experimental results showing the inhibitory activity of CHO-recKRIX-1 and mutated antibodies with N-glycosylation site in the variable region, in accordance with an embodiment of the invention. To assess the inhibitory activity of the antibodies, one volume of antibody at various dilutions was mixed with one volume of a pool of normal human plasma and incubated for 2 h at 37° C. The residual Factor VIII activity was then measured in a chromogenic assay.

Figure 24:
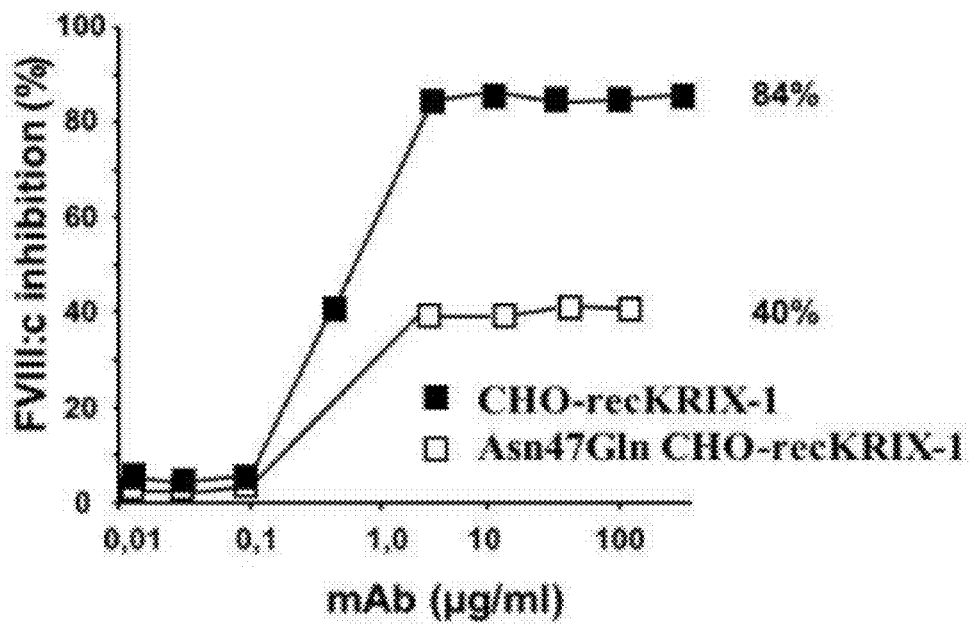

FIG. 24: Graph of experimental results showing the inhibitory activity of CHO-recKRIX-1 and CHO-recKRIX-1Q, in accordance with an embodiment of the invention. To assess the inhibitory activity of the antibodies, one volume of antibody at various dilutions was mixed with one volume of a pool of normal human plasma and incubated for 2h at 37° C. The residual Factor VIII activity was then measured in a chromogenic assay.

Figure 25:
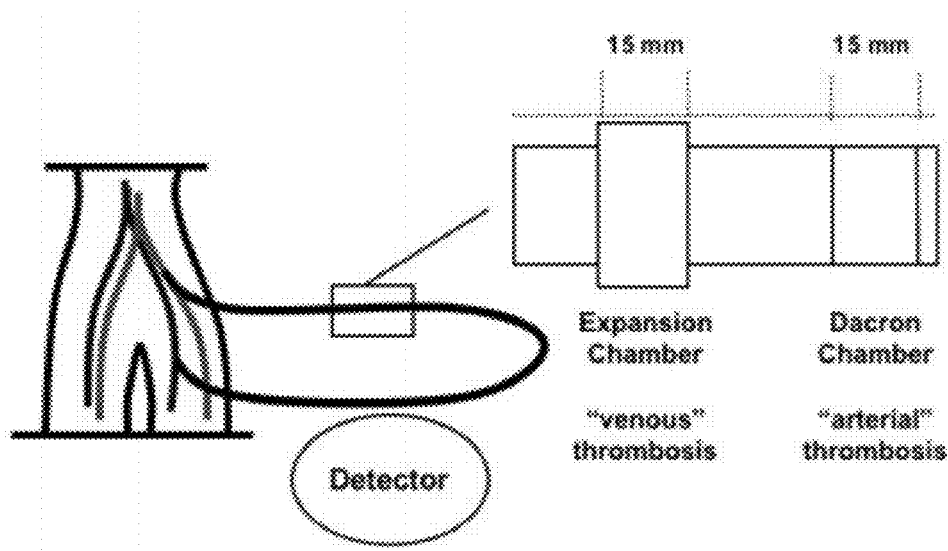

FIG. 25: Drawing representing the experimental protocol for extracorporeal thrombosis in baboons. Arterial and venous thrombogenic devices. Arteriovenous shunts were implanted in male baboon femoral vessels. Thrombogenic devices prefilled with saline were incorporated as extension segments into the permanent arteriovenous shunt. Platelet-dependent arterial thrombus was induced by inserting Dacron into the wall of Silastic tubing. Coagulation-dependent venous thrombosis was generated in an expansion chamber. The deposition of autologous radiolabeled platelets was followed with a gamma scintillation camera.

Figure 26:
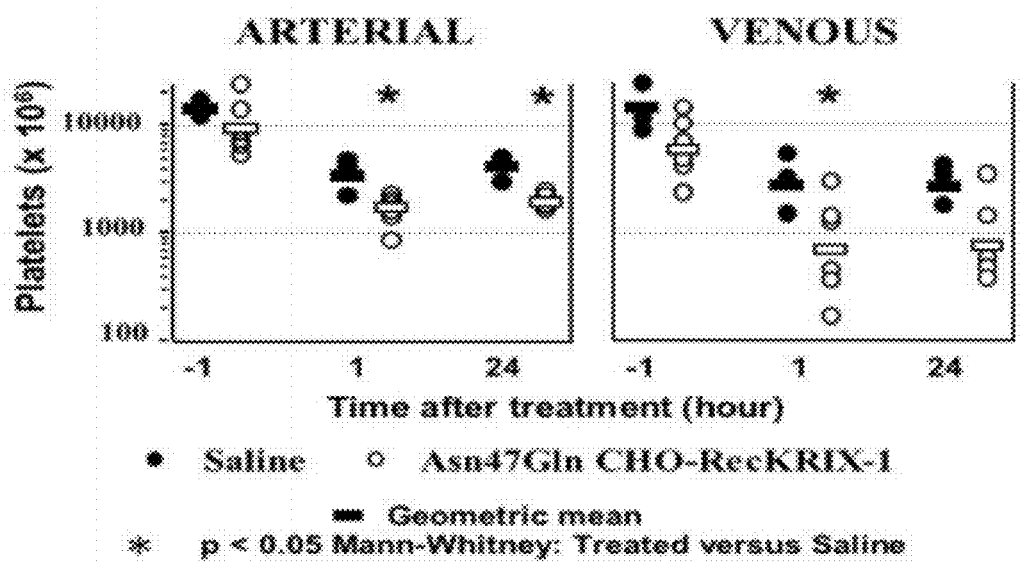

FIG. 26: A graph of experimental results showing the inhibition of platelet deposition in the arterial and venous thrombosis chambers before and after administration of CHO-recKRIX-1Q, in accordance with an embodiment of the invention. Platelet deposition was recorded as a function of time in the expansion ("venous") thrombosis chamber (A) and in the Dacron ("arterial") thrombosis chamber (B) incorporated in an extracorporeal arteriovenous shunt implanted between femoral vessels. In the control studies, the devices were kept in place for 60 min or until occlusion of the catheter. The baboons were then treated with a single intravenous bolus of antibody. New thrombogenic devices were placed then for 60 minutes, 1 h, 24 h after the bolus injection. The extracorporeal shunts were then removed.

Figure 27:
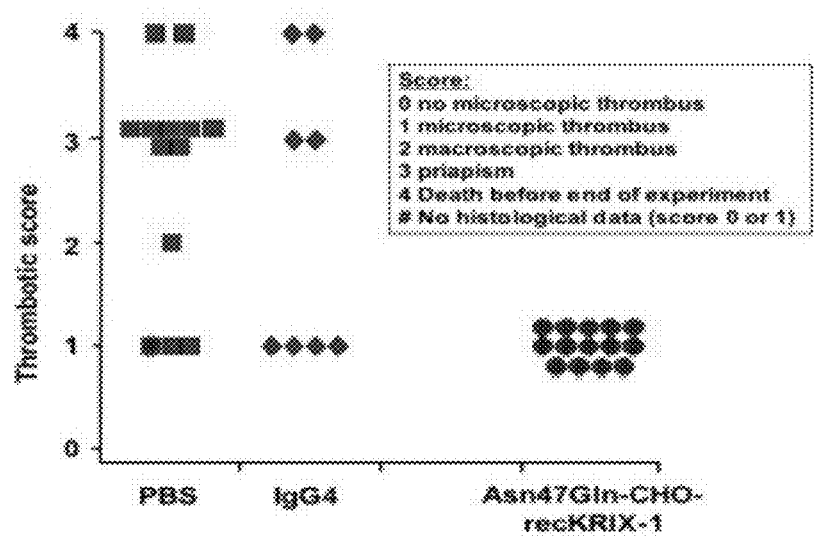

FIG. 27: Graph of experimental results showing that CHO-recKRIX-1Q protects against penile thrombosis and priapism in mated $AT^{m/m}$ males, in accordance with an embodiment of the invention. Males were injected twice subcutaneously with vehicle (PBS), or with 100 μg antibody CHO-recKRIX-1Q or a control IgG4 human monoclonal antibody (IgG4), three days before and on the day of mating. Thrombotic outcome was scored zero if the mice were free of thrombosis at the end of the 8-day follow-up, 1 if microscopic thrombosis without priapism was observed, 2 if macroscopic thrombosis without priapism occurred, and 3 if the males developed severe thrombosis with irreversible priapism. (#) Animals free of macroscopic thrombosis at the end of the experiment but which could not be analyzed by microscopy were scored 1.

Figure 28:
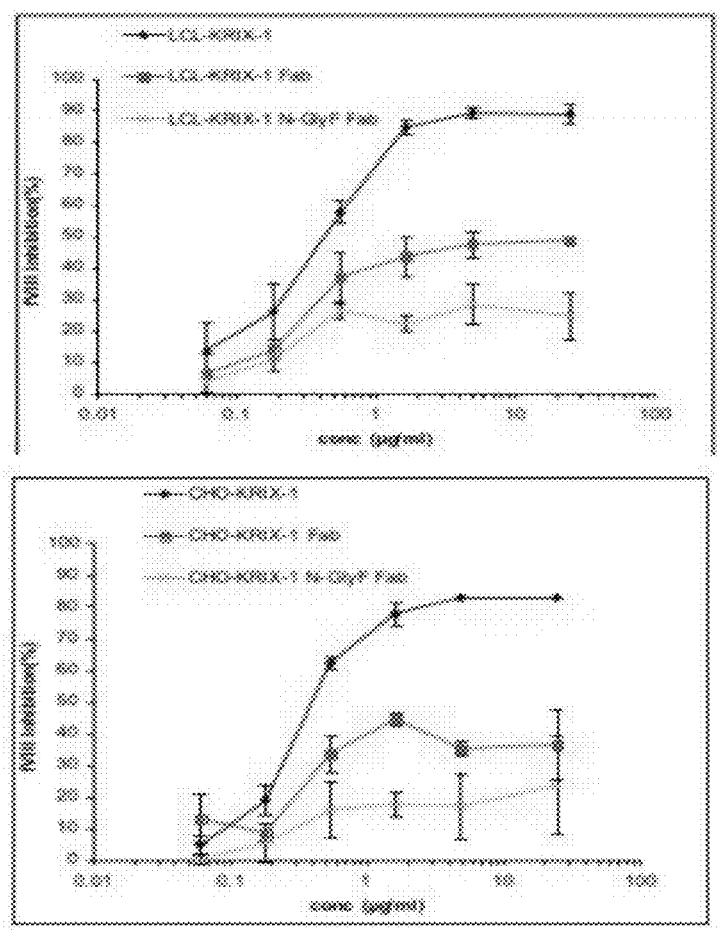

FIG. 28: Graph of experimental results showing the inhibitory activity of native and deglycosylated Fab fragment of LCL-KRIX-1 and CHO-KRIX-1, in accordance with an embodiment of the invention. KRIX-1 was deglycosylated by treatment with N-glycosidase-F and Fab were produced by digestion with papain. To assess the inhibitory activity of intact antibodies and native and deglycosylated Fab, one volume of antibody at various dilutions was mixed with one volume of a pool of normal human plasma and incubated for 2 h at 37° C. The residual Factor VIII activity was then measured in a chromogenic assay.

Figure 29:
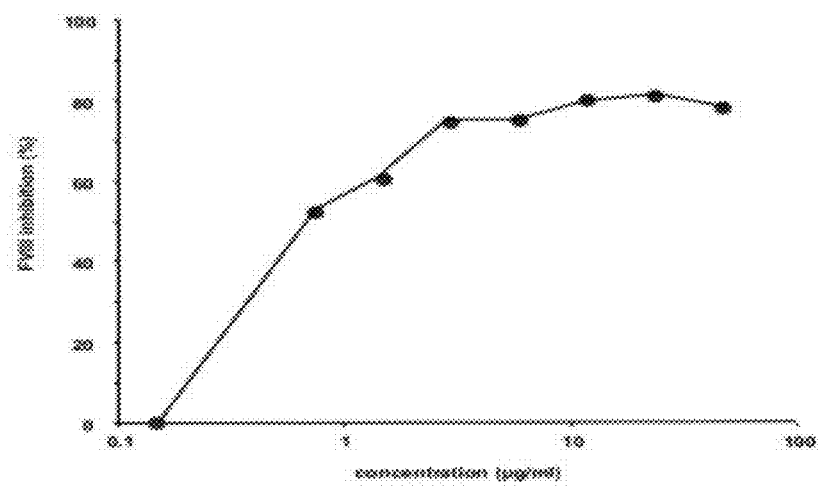

FIG. 29: Graph of experimental results showing the Factor VIII inhibitory activity of scFv fragment of KRIX-1 (scFv-KRIX-1VLVH(His)) produced in *Pichia pastoris*, in accordance with an embodiment of the invention. To assess the inhibitory activity of scFv-KRIX-1VLVH(His), one volume of buffer with scFvKRIX-1VLVH(His) at various concentrations was mixed with one volume of a pool of normal human plasma and incubated for 2 h at 37° C. The residual Factor VIII activity was then measured in a chromogenic assay.

Figure 30:
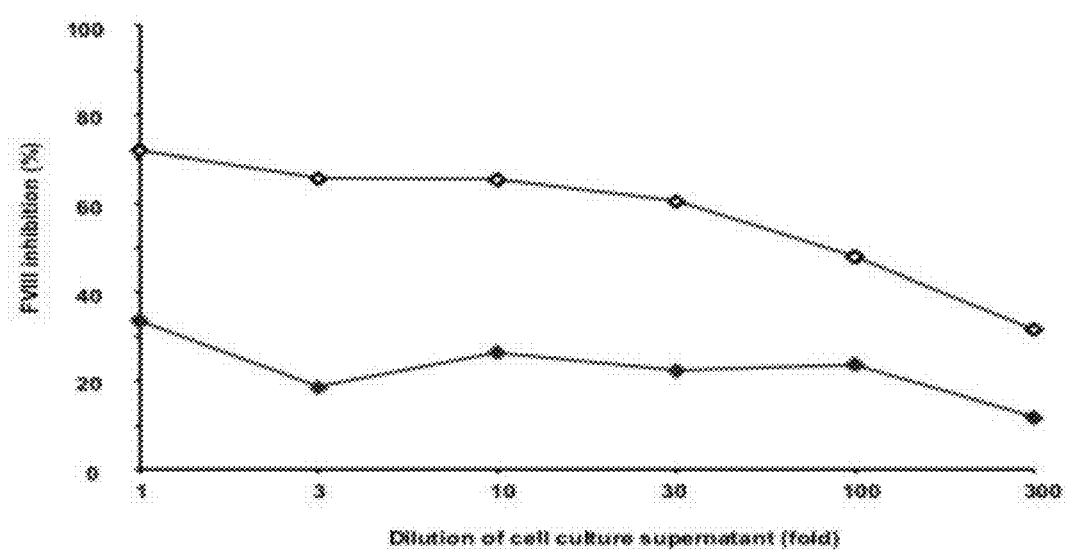

FIG. 30: Graph of experimental results showing the Factor VIII inhibitory activity of scFv fragment of KRIX-1 and KRIX-1Q, in accordance with an embodiment of the invention. To assess the inhibitory activity of scFv fragment of KRIX-1 and KRIX-1Q, one volume of culture supernatant of CHO cells, transfected with an expression vector for scFv-KRIX-1VLVH(His) (open symbols) or scFv-KRIX-1VLVHQ(His) (closed symbols), at various dilutions was mixed with one volume of a pool of normal human plasma and incubated for 2 h at 37° C. The residual Factor VIII activity was then measured in a chromogenic assay.

DEFINITIONS

The term "antibody" generally refers to an antibody of any origin such as from human, murine, camel or other origin, and includes an antibody of any class or isotype such as IgG, IgA, IgM, IgD, and IgE, and any subclass within such a class, such as for IgG, IgG1, IgG2, IgG3 and IgG4.

The term "fragment" when referring to an antibody against Factor VIII includes molecules comprising either parts of both heavy and light chains, (such as Fab, F(ab)$_2$, F(ab')$_2$ or ScFV) or single heavy or light chains (e.g. light chain dimers), optionally including their constant region (or parts thereof), or optionally minor modifications (such as allotypic variants) of that constant region. It moreover includes parts of said heavy and/or light chains, such as the variable regions of the antibodies, subparts thereof, in particular the hypervariable (HV) or complementarity determining region(s) (CDR(s)). Thus antibody fragments include peptides made up of stretches of amino acids comprising at least one CDR, optionally with adjacent framework sequences, e.g. of up to about 10 amino acid sequences at one or both ends of the CDR(s).

A "complementarity determining region (CDR)" in the present invention refers to a hypervariable amino acid sequence isolated from or present within an antibody variable region, which interacts with the epitope on the antigen. Traditionally, based on their position in the intact antibody, CDR regions are numbered "CDR1", "CDR2" and "CDR3" of the variable light (VL) and heavy (VH) chains, respectively (also referred to as L1, L2, L3 and H1, H2, H3 respectively).

A "humanized" antibody or antibody fragment as used herein, refers to antibody molecules or fragments thereof in which amino acids have been replaced in the non-antigen binding regions in order to more closely resemble a human antibody.

A "Reshaped" human antibody or antibody fragment or a "Human hybrid" antibody or antibody fragment as used herein, refers to a human antibody or fragment thereof in which amino acids in the antigen binding regions have been replaced with sequences in accordance with the present invention, e.g. CDR's, or other parts of variable regions which have been derived from the repertoire of human antibodies.

The term "native antibody" as used herein refers to the original antibody as obtained from a cell line producing said antibody under standard culturing of a lymphoblastoid cell line, i.e. unmodified by the addition of enzymes or by mutations. Such a native antibody is also referred to as a wild-type antibody. For instance, in the context of the present invention, when reference is made to the native Krix-1 antibody, a comparison to the antibody as obtained from the Krix-1 cell line (deposited as LMBP 5089CB), under standard cultivation conditions is intended.

The term "derivative" of an antibody or antibody fragment as used herein refers to an antibody or fragment thereof which has been altered chemically or genetically thereby retaining at least part of or improving its ability to bind to the epitope of the native antibody. Examples of derivatives of antibodies and antibody fragments include antibodies or fragments in which either the amino acid sequence has been modified and/or antibodies or fragments in which glycosylation has been modified as well as "polymorphisms" of antibodies.

An antibody or fragment having a modified amino acid sequence includes a molecule in which one or more amino-acids have been either substituted by any other amino-acid residue or deleted compared to the native antibody. Such amino-acid substitution or deletion can be located anywhere in the antibody or antibody fragment molecule. It also includes molecules in which amino-acid residues have been substituted and/or deleted at more than a single location.

When referring in the present application to an antibody or antibody fragment of which the glycosylation has been "modified" it is intended to refer to antibodies or fragments thereof which have been engineered or produced in a way that their glycosylation differs from that of the native antibody, meaning that certain extra carbohydrates are present or certain carbohydrates are missing, or both, relative to the native antibody. The modification of the glycosylation can occur at one or at different positions in the antibody or antibody fragment.

The term "polymorphisms" refers to the result of the regular and simultaneous occurrence in a single interbreeding population of two or more alleles of a gene, where the frequency of the rarer alleles is greater, typically greater than 1%, than can be explained by recurrent mutation alone.

The term "homology" or "homologous" as used herein with reference to the antibodies or antibody fragments in accordance with the present invention refers to a molecule which will compete with or inhibit binding of one of the antibodies or antibody fragments in accordance with the present invention to the antigen. The binding should be specific, i.e. the binding of the alternative molecule should be as specific to the antigen as the antibody or antibody fragment in accordance with the present invention. Where used to refer to the antibodies or antibody fragments in accordance with the present invention, homology includes, but is not limited to, molecules having at least 80%, more preferably 90% and most preferably 95% amino acid sequence similarity or sequence identity with the sequence of the relevant antibody or antibody fragment.

Sequence comparisons: Comparisons of protein or nucleotide sequences can be designated in terms of sequence identity or sequence similarity. Nucleotide or amino acid sequences which are "identical" means that when two sequences are aligned, the percent sequence identity, i.e. the number of positions with identical nucleotides or amino acids divided by the number of nucleotides or amino acids in the shorter of the sequences, is higher than 80%, preferably at least 90%, even more preferably at least 95%, most preferably at least 99%, more specifically is 100%. The alignment of two nucleotide sequences is performed by the algorithm as described by Wilbur and Lipmann (1983) *Proc. Natl. Acad. Sci. U.S.A.* 80:726, using a window size of 20 nucleotides, a word length of 4 nucleotides, and a gap penalty of 4.

Two amino acids are considered as "similar" if they belong to one of the following groups GASTCP; VILM; YWF; DEQN; KHR. Thus, sequences which are similar means that when the two protein sequences are aligned the number of positions with identical or similar nucleotides or amino acids divided by the number of nucleotides or amino acids in the shorter of the sequences, is higher than 80%, preferably at least 90%, even more preferably at least 95% and most preferably at least 99%, more specifically is 100%.

Alternatively, comparisons of protein or nucleotide sequences can be designated in terms of number of the number of amino acids or nucleotides (or codons) that are different. When referring to a modified Krix-1 antibody for instance, it includes antibodies or antibody fragments comprising an amino acid sequence in which the CDR sequences, when compared to native Krix-1 each differ in maximally 3 amino acids. The maximal number of modified amino acids within the CDRs, when compared to Krix-1 is thus 18.

An "inhibitory antibody" or an "antibody with inhibitory activity" as used herein refers to an antibody which inhibits the activity of its target protein at least partially. The term "partial inhibition" or "plateau inhibition" as used herein refers to an inhibition of activity which is less than 100%.

The term "thrombotic pathological condition" or a thrombotic disorder is a disorder wherein unwanted clot or 'thrombus' is produced or wherein the risk of clot formation is increased. Examples of thrombotic pathological conditions include, but are not limited to intravascular coagulation, arterial thrombosis, peripheral artery disease (PAD), coronary arterial disease (CAD), arterial restenosis, venous thrombosis (notably deep vein thrombosis (DVT), pulmonary embolism (PE), cerebral ischemic disorders, atrial fibrillation and arteriosclerosis.

As used herein "comprising" is to be interpreted as specifying the presence of the stated features, integers, steps, reagents or components as referred to, but does not preclude the presence or addition of one or more features, integers, steps or components, or groups thereof. Thus, e. g., a nucleic acid or protein comprising a sequence of nucleotides or amino acids, may comprise more nucleotides or amino acids than the actually cited ones, i. e., be embedded in a larger nucleic acid or protein.

DETAILED DESCRIPTION OF THE INVENTION

The present invention will be described with reference to certain embodiments and to certain figures but the present invention is not limited thereto. In particular, the present invention will mainly be described with reference to ligands to Factor VIII but the present invention is not limited thereto.

The present invention relates to a general concept of obtaining a therapeutically useful "plateau inhibition" of coagulation by only partially inactivating a factor involved in coagulation. More particularly, the invention relates to the selection of certain monoclonal antibodies, as well as to the production of such human or humanized monoclonal antibodies, or fragments, derivatives or homologs thereof, and using these for anti-thrombotic therapy and in anti-thrombotic therapeutic compositions. These partial inhibitors and compositions comprising such inhibitors have the advantageous property that the inactivation of the factor they target is only partial even when the ligand is in a molar excess. This is of interest for the coagulation cascade in that complete inhibition may cause side effects such as uncontrolled bleeding. Partial inhibition means that even though the ligand is used in an amount which might be expected to inactivate completely the targeted factor, the inactivation is still incomplete, and that there is as such no risk of 'overdosing'.

According to a first aspect, the present invention relates to antibodies, also referred to herein as 'ligands' herein, which are reactive with human Factor VIII and more specifically have the capacity of inactivating the co-factor activity of human factor VIII by interfering with proteolytic cleavage site or von Willebrand factor or tenase complex reaction or by inducing a three-dimensional conformational change in Factor VIII, in particular by targeting a domain of Factor VIII and by recognizing epitopes located in the said domain.

Thus, according to the invention, monoclonal antibodies are provided which inhibit Factor VIII activity. According to a particular embodiment Factor VIII activity refers to the ability of Factor VIII to act as co-factor in the coagulation cascade, which can be evaluated by its effect on coagulation, such as but not limited to by the methods described herein (see below). This inhibition can be caused by the fact that Factor VIII is inhibited from binding other factors such as vWF and/or phospholipids. According to a particular embodiment of the invention, the inhibitory antibodies are directed to the C1 domain of Factor VIII. Although the inventors do not wish to be bound to a single explanation or theory, it is believed that the binding of such human monoclonal antibodies results in partial impairment of the binding of activated Factor VIII to phospholipids, a necessary step for cofactor activity expression. According to a further particular embodiment, the antibodies of the present invention are of the class IgG.

A particular embodiment of the present invention relates to the KRIX-1 antibodies produced by the KRIX-1 cell line described herein which has been obtained as described herein. Krix-1 antibodies are directed against the C1 domain of Factor VIII and are capable of partially inhibiting the co-factor activity of Factor VIII. The invention further provides antibodies capable of binding to the same antigen as the Krix-1 antibody, more in particular antibodies binding to the same epitope as bound by the Krix-1 antibody, bound by the antibody produced by cell lines mentioned hereinabove; even more particularly, the present invention provides antibodies which compete with Krix-1 for binding to Factor VIII as tested with an ELISA as described herein. Particularly, the antibodies have at least 80% sequence identity, more particularly at least 90% sequence identity, even more particularly at least 95% sequence identity, most particularly at least 98% sequence identity, with the Krix-1 antibody within their CDR regions. Additionally or alternatively, the antibodies have an amino acid sequence which differs from Krix-1 in maximally 3 amino acids within each CDR. More particularly, the total number of modified amino acids within all of the CDRs is 15, even more particularly the maximum number of modified amino acids for all of the CDRs, compared to native Krix-1, is 12.

According to an alternative embodiment, the present invention relates to RHD5 antibodies produced by the RHD5 cell line described herein which has been obtained as described herein. RHD5 antibodies are directed against the C1 domain of Factor VIII and are capable of partially inhibiting the co-factor activity of Factor VIII. The invention further provides antibodies capable of binding to the same antigen as the RHD5 antibody, more in particular antibodies binding to the same epitope as bound by the RHD5 antibody, bound by the antibody produced by cell lines mentioned hereinabove; even more particularly, the present invention provides antibodies which compete with RHD5 for binding to Factor VIII as tested with an ELISA as described herein. Particularly, the antibodies have at least 80% sequence identity, more particularly at least 90% sequence identity, even more particularly at least 95% sequence identity, most particularly at least 98% sequence identity, with the RHD5 antibody within their CDR regions. Additionally or alternatively, the antibodies have an amino acid sequence which differs from RHD5 in maximally 3 amino acids within each CDR. More particularly, the total number of modified amino acids within all of the CDRs is 15, even more particularly the maximum number of modified amino acids for all of the CDRs, compared to native RHD5, is 12.

Alternatively or additionally, a site on the C2 domain of Factor VIII may also be partially inhibited. The present invention also includes ligands other than polyclonal antibodies, in particular monoclonal antibodies, which reduce the release rate of Factor VIII from von Willebrand factor. These monoclonal antibodies specifically target Factor VIII when bound to von Willebrand factor and hence target an epitope associated with the complex of Factor VIII and von Willebrand factor.

The antibodies of the present invention may be of human or animal origin. They can be a result of a purposely directed immunization or can be alloantibodies produced against exogenous Factor VIII.

The present invention further provides monoclonal antibodies having substantially the same characteristics as the antibodies disclosed herein. Such antibodies can be produced by on purpose immunization in animals, preferably in mouse, for instance by injecting human Factor VIII in mice and then fusing the spleen lymphocytes with a mouse myeloma cell line, followed by identifying and cloning the cell cultures producing anti-Factor VIII antibodies. The monoclonal antibodies produced in animals are then humanized, for instance by associating the binding complementarity determining region ("CDR") from the non-human monoclonal antibody with human framework regions—in particular the constant C region of human gene—such as disclosed by Jones et al. in Nature (1986) 321:522 or Riechmann in Nature (1988) 332: 323. The present invention also relates to recombinant antibodies of antibodies according to the description hereof such as Krix-1 or RHD5, produced in any suitable host cell (e.g. CHO cells).

The present invention also provides fragments of monoclonal antibodies such as Fab, Fab', F(ab')$_2$, scFv, CDR's, single variable domains as well as derivatives, homologs and combinations of these. More particularly, these monoclonal antibodies and fragments may target a domain of Factor VIII, in particular the C1 domain of Factor VIII. They may also partially inhibit a site on the C2 domain of Factor VIII. They may also target an epitope associated with the complex of von Willebrand factor and factor VIII. An aspect of the present invention is therefore to provide ligands other than polyclonal antibodies which bind to a first site (e.g. in the C1 domain of Factor VIII) remote from a functional second site (e.g. the site in the C2 domain of Factor VIII which is responsible for binding phospholipids) in such a way that the function of the second site is only partially impaired even when the ligand is in a molar and therapeutic excess.

Such fragments, which contain the antibody binding site, have lost a number of properties of the parent antibody, such as complement activation or capacity to bind to Fc gamma receptors. The present invention also includes single chain fragment variables (scFv), single variable domain fragments of the antibodies and combination of these fragments and of the above mentioned fragments.

The present invention thus also provides fragments and derivatives, in particular complementarity determining regions ("CDR's") of the monoclonal anti-Factor VIII antibodies described herein as well as homologs thereof For instance, the invention provides antigen-binding fragments Fab, Fab' and F(ab')$_2$ generated by proteolytic digestion of the said monoclonal antibodies using methods well known in the art, such as described by Stanworth et al., Handbook of Experimental Immunology (1978), vol. 1 chapter 8 (Blackwell Scientific Publications). Briefly, an F(ab')$_2$ is obtainable after pepsin cleavage and is built up of both light chains and parts of the heavy chains disulfide linked via the hinge region. The Fab fragment is obtainable from the intact antibody or from the F(ab')$_2$ by papain digestion of the hinge region and contains a one light chain and one part of the heavy chain. Fragments of antibodies can also be obtained by synthesis or by recombinant methods described in the art.

The invention also provides soluble or membrane anchored single-chain variable parts (scFv fragments) of the above monoclonal antibodies. Methods for obtaining scFv fragments are known to the skilled person and include the method as follows. The DNA sequences of the variable parts of human heavy and light chains are amplified in separated reactions and cloned. A fifteen amino-acid linker sequence, for instance (Gly4 Ser)3, is inserted between VH and VL by a two-steps polymerase chain reaction (PCR), for instance according to Dieffenbach and Dveksler, "PCR Primer, a laboratory manual" (1995), Cold Spring Harbour Press, Plainview, N.Y., USA. The resulting fragment is then inserted into a suitable vector for expression of single chain fragment variable (scFv) as soluble or phage-displayed polypeptide. This can be achieved by methods well known to those skilled in the art, such as described by Gilliland et al., *Tissue Antigens* (1996) 47:1-20. The present invention also includes a ligand comprising peptides representative of hypervariable regions of a monoclonal antibody which can be obtained by synthesis using an applied biosystem synthesizer, for instance a polypeptide synthesizer such as model 9050 available from Milligen (USA) or a model from a related technology, which alone or in combination with other or similar hypervariable regions will exert properties similar to that of the parent antibody.

The present invention further provides reshaped human monoclonal antibodies or human hybrid monoclonal antibodies against Factor VIII, which bind to and only partially inactivate Factor VIII or a complex including Factor VIII and von Willebrand factor which comprise only elements derived from the repertoire of human antibodies. Conventionally in the art, until now it has only been possible to obtain antibodies against Factor VIII derived from animals, e.g. mice, or to construct chimeric antibodies from human antibodies with the variable portions derived from mice antibodies.

According to a further embodiment of the present invention, modified antibodies of the herein described monoclonal antibodies are provided, wherein the amino acid sequence is modified. Most particularly, modified versions of the partially inhibitory antibodies or fragments of antibodies described herein are provided, whereby the modification results in a modified glycosylation pattern, whereby these modified antibodies are still capable of binding to Factor VIII and partially inactivating Factor VIII.

Methods for obtaining antibodies with a modified glycosylation are known in the art and described herein. Briefly, such methods include the following steps:

exposing antibodies to carbohydrate cleaving or transforming enzymes;
 producing the antibodies in cell lines with suitable glycosylation enzymes or by modifying the cell culture conditions to modify the activity of the glycosylation enzymes of the cell line producing the antibodies
 genetically modifying the antigen binding site of the antibody in order to remove or introduce glycosylation sites, for example by site-directed mutagenesis.

In a particular embodiment, said modified inhibitory antibodies or fragments thereof have a modified glycosylation and, as a result thereof, a modified (i.e. increased or decreased) inhibitory activity. Most particularly, according to the present invention the modified antibodies and fragments thereof have a decreased inhibitory activity compared to the unmodified antibody. The present invention thus discloses antibodies or fragments thereof, derived from the antibodies of the present invention, inhibiting Factor VIII activity by about 85, 50, 40, 30 and 20%. More particularly the invention relates to a monoclonal antibody or fragment thereof, which is a modified monoclonal antibody or fragment, inhibiting less than 65% of Factor VIII activity.

According to a further particular embodiment, the modified inhibitory antibodies of the present invention having a modified glycosylation are characterised in that the affinity of said antibodies or fragments thereof for their target protein is substantially unaffected compared to the unmodified antibody. As indicated above, the invention also relates to modified fragments and derivatives of the antibodies of the present invention. Thus, the modified antibodies of the present invention include fragments thereof such as, but not limited to, Fab fragments, F(ab')$_2$ fragments and scFvs.

The modification of the glycosylation of native antibodies can be obtained through different methods known in the art. Modification of the glycosylation pattern in the antigen binding site of the antibodies of the present invention can be achieved by enzymatic treatment of purified antibodies. Alternatively, modification of the glycans of the antibodies of the present invention can be achieved by producing the antibodies in cell lines with suitable glycosylation enzymes or by modifying the cell culture conditions to modify the activity of the glycosylation enzymes of the cell line producing the antibodies. Alternatively, the antibodies of the present invention can also be produced by genetically modifying the antigen binding site of the antibody in order to remove or to introduce glycosylation sites.

Many carbohydrate cleaving or transferring enzymes can be applied in order to modify the glycosylation pattern of a native antibody. The glycosylation can be increased or decreased completely or partially. In a particular embodiment, the modification is obtained in the antigen binding region of the antibody. Enzymes can be applied on a native antibody in a different order and under variable circumstances (concentrations, time, temperature, buffer, etc.) in order to obtain antibodies with different glycosylation patterns.

Enzymes such as peptide N-4(N-acetyl-beta-glucosaminyl)asparagine amidase F (PNGase F), also called N-glycosidase F can be used. This enzyme has a broad specificity, and it releases nearly all known N-linked oligosaccharide chain from proteins (Plummer T H Jr et al. (1984) *J Biol Chem.* 259, 10700-10704). This enzyme releases tetra-and penta-antennary chains. It is noteworthy that the activity of the enzyme can only be predicted when the glycoprotein is fully denatured. Accordingly, the activity of the enzyme on an intact antibody must be controlled in each case. Methods to control the deglycosylation of the antibody are described in Current Protocols in Protein Science, Ed. G. Taylor, Unit 12.4; John Wiley & Sons, Inc.

In particular, the glycosylated and deglycosylated antibodies are compared by isoelectrofocusing. Truncated glycoforms of IgG can be generated by sequential enzymatic treatment as described in Mimura et al. (2001) *J Biol Chem.* 276, 45539-45547, and summarized in FIGS. 1 and 2.

Sialic acids are the terminal sugars on many N-and O-linked oligosaccharides. To remove sialic acid, the native IgG in acetate buffer, pH 5.0, are exposed to sialidase (such as the sialidase from *Arthrobacter ureafaciens*, Roche Molecular Diagnostics, East Sussex, UK) at 37° C. for 24 h. Removal of sialic acids results in an increase in the isoelectric point of the protein. IEF can therefore be used to control removal of sialic acids.

Upon removal of sialic acids, galactose can be removed by treatement with beta-galactosidase (*Diplococcus pneumoniae*, Roche Molecular Biologicals) in acetate buffer, at 37° C. for 24 h. Following removal of sialic acid and galactose, N-acelylglucosamine can be cleaved by treatment with N-acetyl-beta-D-glucosaminidase (*D. pneumoniae*, Roche, Molecular Biochemicals) in 37° C. for 24 h. Mannose residues can then be removed by treatment with cc-mannosidase (jack bean, Glyko, Oxfordshire, UK) at 37° C. for 48 h (Mimura Y. et al. cited supra).

Different types of sialidase have also been described. The sialidase (neuraminidase) from *Arthrobacter ureafaciens* releases both alpha 2,3-and alpha 2,6-linked sialic acids, whereas the sialidase from the Newcastle disease virus releases only alpha 2,3 linked sialic acids (Jassal et al. (2001) *Biochem Biophys Res Comm.* 286: 243-249). The endoglycosidase F2 cleaves the bound between the two GlcNAc residues in the core region, leaving one GlcNAc still bound to the protein. Endoglycosidase F2 preferentially releases biantennary complex-type oligosaccharides chains from glycoproteins but does not cleave tri-or tetraantennary chains Endoglycosidase F3 is another endoglycosidase with a narrow substrate range: it cleaves triantennary chains. A core fucosylated biantennary chain is the only other demonstrated substrate. It does not cleave high-mannose hybrid, nonfucosylated biantennary or tetraantennary chains. All linkages which can be cleaved by endoglycosydase F2 and F3 are not exposed in a mature antibody. Methods suitable to determine whether an antibody can be usefully modified by these endoglycosidase include SDS-PAGE, lectin binding methods using Ricinus communis agglutinin-1 and IEF as described above. Conversely, glycan residues can be enzymatically added to carbohydrate expressed in the variable part of the antibody. For example, treatment with sialidase as described above can be followed by treatment with galactosyl-transferase and UDP-Gal in a suitable buffer (Krapp et al. (2003) *J Mol Biol.* 325, 979-989). The modified antibodies are then homogenous for galactosylation of the carbohydrate chain (biantennary digalactosylated glycoform).

The purification of antibodies carrying different oligosaccharides is also known to persons skilled in the art. The antibodies carrying different oligosaccharides can be purified by lectin affinity chromatography, such as Concanavalin A (binding to a bisecting GlcNAc). Aleuria aurantia differentiates on the basis of core fucosylation. *Ricinus communis* agglutinin 1 fractionates according to the number of galactose residues because this lectin exhibits specific affinity to oligosaccharides ending with galactose (Youings et al. (1996) *Biochem J.* 314, 621).

An alternative method for modifying the glycosylation of an antibody is to generate recombinant antibodies with modified glycosylation pattern by producing recombinant antibodies in cell lines selected as a function of their repertoire of glycosylation enzymes. Chinese Hamster Ovary cells (CHO) are well known example of such a cell line.

Although CHO cells have most of the human repertoire of glycosylation enzymes, they are deficient in particular glycosyltransferases. In particular, the alpha 2,6-sialyl-transferase gene (1,2) is not expressed endogenously in CHO cells. This enzyme adds terminal galactose sugars with sialic acid in the alpha 2,6 position on the Gal beta 1, 4G1cNAc-R sequence. However, CHO cells express a functional alpha 2,3-sialyl-transferase so that the terminal sialic acids are in alpha 2,3 linkage to galactose. Alpha-3/4 fucosyltransferase is also not synthesized by these cells (Grabenhorst et al. (1999) *Glycoconj. J.* 16, 81).

Another method to produce recombinant antibody with modified glycosylation pattern is to use a cell line genetically modified to express glycosylation enzyme from other strains. In particular, a CHO-K1 cell line transfected with an alpha 2,6-sialyltransferase gene cloned from another strain can be used (cited supra).

Any expression system is potentially suitable for the generation of recombinant antibody with modified glycosylation pattern such as yeast (for example *Saccharomyces, Pichia, Hansenula*), insect cells (baculovirus expression), plant cells or plants, or mammalian cells. For the expression of fragments of an antibody yeast expression provide an alternative for insect or mammalian cell expression. If no glycosylation at all is needed, the expression in bacteria is considered.

With respect to yeasts, the methylotrophic yeast *Pichia pastoris* was reported to attach an average of 8 to 14 mannose units, i.e. Man(8-14)GlcNAc(2) per glycosylation site (Tschopp in EP0256421) and approximately 85% of the N-linked oligosaccharides are in the size range Man(8-14) GlcNAc(2) (Grinna and Tschopp (1989) *Yeast* 5,107-115.). Aspergillus niger is adding Man(5-10)GlcNAc(2) to N-glycosylation sites (Panchal and Wodzinski (1998) *Prep Biochem Biotechnol.* 28, 201-217). The *Saccharomyces cerevisiae* glycosylation deficient mutant mnn9 differs from wild-type *S. cerevisiae* in that mnn9 cells produce glycosylated proteins with a modified oligosaccharide consisting of Man (9-13)GlcNAc(2) instead of hyperglycosylated proteins (Mackay et al. in U.S. Pat. No. 5,135,854), However, characteristic for *S. cerevisiae* (wild-type and mnn9 mutant) core oligosaccharides is the presence of terminal alpha1,3-linked mannose residues (Montesino et al. (1998) *Protein Expr Purif.* 14, 197-207.). Oligosaccharides attached to N-glycosylation sites of proteins expressed in *P. pastoris* or *S. cerevisiae* och1mnn1 are devoid of such terminal alpha1,3-linked mannoses (Gellissen et al. (2000) *Appl Microbiol Biotechnol.* 54, 741-750). Terminal alpha1,3-linked mannoses are considered to be allergenic (Jenkins et al. (1996) Nat. Biotechnol. 14, 975-981). Therefor, proteins carrying on their oligosaccharides terminal alpha1,3-linked mannose residues are likely not suitable for diagnostic or therapeutic purposes.

The repertoire of glycosylating enzymes differs from cell type to cell type. In order to obtain a desired glycosylation pattern one or more glycosylating enzymes can be (over) expressed by transient or stable transfection. Equally one or more glycosylating enzymes can be temporarily (for example by antisense or siRNA technology) or permanently inhibited (gene inactivation). In certain embodiment yeast cells are used which have a limited repertoire of enzymes involved in glycosylation. Herein one or more human genes involved in glycosylation can be introduced to obtain a desired glycosylation pattern.

Additionally or alternatively, culture conditions can be exploited to modify the glycosylation of the recombinant antibody. The concentration of dissolved oxygen at steady state in serum free culture has an effect on glycosylation of antibody. The extent of galactosylation is reduced with reduced dissolved oxygen concentrations (Kunkel et al. (1998). *J Biotechnol.* 62, 55-71). Supplementing the medium with more than 20 mM N-acetylglycosamine can also induce new antibody glycoforms (Tachibana et al. (1992). *Biochem Biophys Res Commun.* 189, 625-32; Tachibana et al. (1996) *In Vitro Cell Dev Biol Anim.* 32, 178-183). Glucocorticoid hormones and interleukin 6 are involved in the modulation of protein glycosylation (Canella and Margni (2002) *Hybrid Hybridomics* 21, 203). Other factors which influence glycosylation are changes in the pH of culture medium and the availability of precursors and nutrients.

Another alternative to the enzymatical modifications and the recombinant production of the antibodies is to use (site-directed) mutagenesis. New glycosylation sites can be introduced or existing glycosylation sites can be removed with this technique. N-glycosylation sites can be introduced by site directed mutagenesis in the variable region of the antibody. Preferably, the mutations are introduced as single amino acid changes, to minimize the effect of the amino acid substitution on the affinity of the antibody for the antigen. Addition of and N-glycosylation site is performed by creation of an Asn-X-Ser/Thr sequence, most commonly by mutating a codon to encode Asn. Moreover, it is preferable that the sites for additional glycosylation are selected at positions predicted to be accessible to glycosyltransferases. Alternatively, amino-acid stretches containing N-glycosylation sites can be selected in the published sequences of antibodies glycosylated in the variable region. The selection of antibodies inhibiting Factor VIII activity in a desirable manner can be made using the Bethesda assay (Kasper et al. (1975) cited supra). The protein structure can also be modified to indirectly modify glycosylation (Lund et al. (1996) *J Immunol.* 157, 4963, Lund et al. (2000), *Eur J Biochem.* 267, 7246). Site-directed mutagenesis is a method well-known to the person skilled in the art, and include the Zoller and Smith method (Zoller and Smith (1987) *Methods Enzymol.* 154:329-50).

In the context of the present invention, the modifications in the glycosylation of the antibodies most particularly occur in the variable region (i.e. VH and/or VL) of the antibodies. In a more particular embodiment, the modified antibody is a modified Krix-1 antibody, with a modified N-glycosylation in the variable region, more particularly with a mutated glycosylation site at positions Asn47 to Thr49 of the heavy chain, more in particular with heavy chain Asn47 changed to Gln47 (KRIX-1Q), Glu47 (KRIX-1E) or Asp47 (KRIX-1D) and/or heavy chain Thr49 to Ala49 (KRIX-1A).

According to a further aspect of the invention, sets of at least two antibodies and/or antibody fragments, capable of binding the same antigen and demonstrating variable maximal inhibition of Factor VIII are disclosed. According to a particular embodiment, the set of at least two antibodies comprises the unmodified antibody or a fragment thereof and at least one modified version thereof, or a fragment thereof. Alternatively, the set of at least two antibodies comprises two modified versions of the anti-Factor VIII antibody of the invention.

According to a further aspect, the present invention provides cell lines producing human monoclonal antibodies which are reactive with human Factor VIII and more specifically have the capacity of inactivating the co-factor activity of human Factor VIII by interfering with proteolytic cleavage site or von Willebrand factor or tenase complex reaction or by inducing a three-dimensional conformational change in Factor VIII, in particular by targeting a domain of Factor VIII and by recognizing epitopes located in the said domain.

According to a particular embodiment, the present invention provides cell lines producing antibodies directed against the C1 domain of Factor VIII.

The cell line named KRIX -1 producing monoclonal antibodies according to the present invention was deposited with the BCCM /LMBP (Belgian Co-ordinated Collections of Microorganisms/Plasmid Collection Laboratorium voor Moleculaire Biologie, University of Ghent K.L. Ledeganckstraat 35, B-9000 Ghent, BE under accession number LMBP 5089CB on Jul. 1, 1999. The cell line named RHD5 also producing monoclonal antibodies according to the present invention was deposited with the Belgian Coordinated Collections of micro-organisms, under accession number 10 LMBP 6165CB, by the D. Collen Research Foundation (Onderwijs & navorsing, Campus Gasthuisberg, Herestraat 49, B-3000 Leuven, Belgium) as depositor (accession number LMBP 6165CB) on Jul. 30, 2004.

The present invention further provides cell lines producing human monoclonal antibodies having a reactivity substantially similar to that of the human monoclonal antibodies obtained from the above-mentioned deposited cell lines, as well as the human monoclonal antibodies obtainable from these further cell lines, and fragments and derivatives thereof. The present invention thus provides more in particular cell lines producing monoclonal antibodies which bind to the C1 domain of Factor VIII; more particularly the antibodies of the invention bind to the same antigen, more in particular to the same epitope, bound by the antibody produced by cell lines mentioned hereinabove; even more particularly, the present invention provides antibodies which compete with the antibodies disclosed herein for binding to Factor VIII as tested with an ELISA, as described herein.

According to the present invention ligands, other than polyclonal antibodies are provided, having the capacity of only partially inactivating a factor (or a complex including a factor) involved in hemostasis, in particular in the coagulation cascade of blood, most particularly Factor VIII or a complex including Factor VIII. Such partial inactivation is ensured by these ligands by binding to a site of the said factor or complex, whereby the said partial inactivation also occurs place when the ligand of the invention is in a molar excess with respect to the said factor. The site to which the ligand binds may or may not be directly or substantially involved in a physiological interaction of the said factor or complex. For instance, the ligand may bind to a site which is at a predetermined distance away from a physiologically functional site of the said factor.

According to a particular embodiment, the "partial" inhibition or "plateau" inactivation of the ligands or antibodies of the invention corresponds to at most 98% inactivation, preferably an at most 95% inactivation, as determined by a suitable test method such as for instance the chromogenic assay available from Coatest® (Kabi Vitrum, Brussels, Belgium) or from Chromogenix AB, Mölndal (Sweden). Alternatively, inhibition of Factor VIII activity can be measured by determining blood clotting in the Bethesda assay (Kasper et al. (1975). The level of activation required may depend upon the physiological function of the factor involved in hemostasis.

According to a particular embodiment of the invention, the partial inhibition achieved by the antibodies of the present invention is at least 10%, most particularly at least 20%. According to a particular embodiment of the invention, inactivation of the blood factor is at least about 65%, alternatively at least about 70%, as determined by the same test method as above. It will be appreciated that the ligands in accordance with the present invention operate in a different way from the mechanism conventionally ascribed to type II antibodies against Factor VIII. One conventional mechanism is that of competition with another factor, e.g. von Willebrand factor. The kinetics of a competition mechanism mean that if the one species is at a high concentration compared with the other (e.g. in a molar excess), the inhibition is effectively complete. In contrast, the ligands of the present invention reach a plateau in the inactivation of the relevant factor, which is substantially independent of the excess of the ligand. The other conventional mechanism ascribed to type II antibodies is that of low affinity: also in this case, an excess will drive the reaction to complete inhibition.

According to yet another aspect of the invention, two or more antibodies or antibody fragments with different partial inhibitory activity of Factor VIII can be combined resulting in a mixture with an intermediate inhibitory activity for Factor VIII. A particular embodiment of the invention is a mixture of two or more partially inhibitory antibodies against Factor VIII or fragments thereof, which ensures a given partial inhibition of Factor VIII, whatever the excess of the mixture of antibodies over Factor VIII. Using combinations of different inhibitory antibodies and/or fragments thereof in specific ratios, mixtures with specific inhibitory activity of Factor VIII can be obtained. Thus, the present invention relates to a combination of two or more antibodies or antibody fragments with different partial inhibitory activities. According to a specific embodiment, two different antibodies or fragments thereof with different inhibitory activity are combined. According to a further specific embodiment the native antibody is combined with one or more antibodies derived therefrom or fragments thereof having a lower inhibitory activity. According to a further embodiment of this aspect of the invention, the native antibody is combined with an antibody or antibody fragment having a modified glycosylation with respect to the native antibody, derived therefrom. Such combinations or mixtures are of interest for further adjustment of the inhibitory activity of the antibody, e.g. in the development of patient-specific pharmaceuticals. The present invention further shows that mixtures of inhibitory antibodies, being derived from the same native unmodified antibody, with different individual inhibitory activity, result in a mixture wherein an intermediate inhibitory activity is obtained. According to a particular embodiment such as a mixture comprises the unmodified monoclonal Krix-1 antibody or a fragment thereof, and a modified Krix-1 antibody, or a fragment thereof. A further embodiment provides a mixture comprising two different modified versions of the Krix-1 antibody. Alternatively, the invention provides mixtures of different antibodies which recognize the same antigen, and thus are competitive for each other. According to a particular embodiment such as a mixture comprises the monoclonal Krix-1 antibody (first antibody)or antibody fragment or a modified version thereof and a second monoclonal antibody or antibody fragment obtained from the RHD5 cell line or a modified version thereof The invention further provides a pharmaceutical composition for the prevention or treatment of disorders of hemostasis, in particular of the coagulation cascade and resulting thrombotic pathologic conditions in humans, comprising, as an active ingredient, a ligand other than a polyclonal antibody, preferably a human monoclonal antibody such as disclosed hereinabove, in admixture with a pharmaceutically acceptable carrier.

According to a particular embodiment the pharmaceutical composition comprises a monoclonal antibody which is a human monoclonal antibody, or a fragment, derivative or homolog thereof such as a modified version thereof, obtainable from the cell line KRIX-1 deposited with the Belgian Co-ordinated Collections of Micro-organisms under accession number LMBP 5089CB or from the cell line RHD5 deposited with the Belgian Co-ordinated Collections of Micro-organisms under accession number LMBP 6165CB. According to a particular embodiment, the pharmaceutical compositions of the present invention comprises a monoclonal antibody, or a fragment thereof which is a modified version of the antibodies described herein, more particularly a modified version having at least 80% sequence identity with antibodies described herein.

The degree of sequence identity or similarity with the said monoclonal antibody is preferably at least 80%, more preferably 90% even more preferably 95%, and most preferably at least 99% and the sequence identity or similarity is preferably particularly in respect to the variable regions (variable heavy and/or variable light regions), most particularly in respect to the complementarity determining regions (CDRs) of the antibody. Additionally or alternatively the degree of identity with the monoclonal antibody is expressed as having maximally 3 different amino acids within each CDR compared to Krix-1. In a particular embodiment, the total number of amino acids that can be changed within all the CDRs is 12. It will be understood that, within the framework regions in the variable regions and within the constant regions, the sequence identity or similarity with Krix-1 is less critical, as these regions affect binding to the antigen to a lesser extent.

A ligand or antibody in accordance with the present invention may also include a synthetic polypeptide of equivalent potency. The pharmaceutical composition of the present invention should comprise a therapeutically effective amount of the said above ingredient, such as indicated hereinafter in respect to the method of treatment or prevention.

The pharmaceutical composition of the present invention may further comprise, namely in view of a so-called adjunctive anti-thrombotic treatment, a therapeutically effective amount of a thrombolytic agent. Such thrombolytic agents, as well as their usual dosage depending on the class to which they belong, are well known to those skilled in the art. Among numerous examples of thrombolytic agents which may be included in the pharmaceutical compositions of the invention, the following non-limiting list may be particularly cited: t-PA, streptokinase, reptilase, TNK-t-PA or staphylokinase.

The pharmaceutical composition of the present invention may further comprise a pharmaceutical carrier. Suitable pharmaceutical carriers for use in the pharmaceutical compositions of the invention are described for instance in Remington's Pharmaceutical Sciences 16$^{th}$ ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxy-methylcellulose, protamine sulfate and the like. The rate of drug release and duration of action may also be controlled by incorporating the monoclonal antibody active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The present invention also provides the use of a ligand, other than a polyclonal antibody (as disclosed above) as a medicament. More preferably the medicament used in the present invention is a means for preventing and/or treating disorders of hemostasis, in particular, coagulation disorders and other thrombotic pathologic conditions in mammals, preferably in humans. The said ligand may be provided to a patient by any means well known in the art, i.e. orally, intranasally, subcutaneously, intramuscularly, intradermally, intravenously, intraarterially, parenterally or by catheterization. According to the present invention, the ligand may also be used as a medicament in conjunction or association with another medicament, for instance a thrombolytic agent such as disclosed hereinabove under the heading of pharmaceutical compositions.

The present invention therefore provides a method of treatment and/or prevention of hemostasis, coagulation disorder or thrombotic pathologic condition as well as a method of attenuation of coagulation in a mammal, preferably a human, comprising administering to a mammal in need of such treatment or prevention or attenuation of coagulation a therapeutically effective amount of a ligand or antibody other than a polyclonal antibody such as disclosed hereinabove.

According to a particular embodiment the method of treatment and/or prevention comprises the administration of a human or humanized monoclonal antibody obtainable from cell line KRIX-1 deposited with the Belgian Co-ordinated Collections of Micro-organisms under accession number LMBP 5089CB or an antigen-binding fragment Fab, Fab' or F(ab')$_2$, a complementarity determining region (CDR), a soluble or membrane-anchored single-chain variable part (scFv), a single variable domain or a derivative, such as a modified antibody, more particularly a glycosylation-modified antibody or combination of any of these elements. Alternatively, the method of treatment and/or prevention comprises the administration of a human or humanized monoclonal antibody obtainable from cell line RHD5 deposited with the Belgian Coordinated Collections of micro-organisms, under accession number LMBP 6165CB, or an antigen-binding fragment Fab, Fab' or F(ab')$_2$, a complementarity determining region (CDR), a soluble or membrane-anchored single-chain variable part (scFv), a single variable domain or a derivative, such as a modified antibody, more particularly a glycosylation-modified antibody or combination of any of these elements. In yet a further particular embodiment, the method of treatment and/or prevention comprises the administration of ligand which is a human or humanized monoclonal antibody binding to the antigen, more in particular to the epitope, bound by the antibody produced by Krix-1 cell line or the RHD5 cell line. In another particular embodiment, the antibody or fragment thereof used in the methods of the present invention is a human or humanized monoclonal antibody which competes with Krix-1 or with RHD5 for binding to Factor VIII as tested with an ELISA as described herein. In another particular embodiment, the antibody or fragment thereof used in the methods of the present invention is a human or humanized monoclonal antibody binding to the C1 domain of Factor VIII, as well as fragments, derivatives, and homologs thereof, with the amino acid sequence of its variable heavy chain being at least 80% (more in particular 90% or 95%) identical or similar to the amino acid sequence of the variable heavy chain of the described anti-Factor VIII antibodies of the invention, within the CDRs of said variable heavy chain and/or a variable light chain sequence being at least 80% (more in particular 90% or 95%) identical to the amino acid sequence of the variable light chain sequence of known anti-Factor VIII antibodies of the invention, within the CDRs of said variable light chain. Additionally or alternatively, the antibodies used in the methods of the invention are characterized in that, with regard to the CDR regions, they differ from the known anti-Factor VIII antibodies in maximally three amino acids within each CDR. Most particularly, the total number of amino acid differences within the CDRs is 12. In another particular embodiment, the antibody or fragment thereof used in the methods of the present invention is a monoclonal antibody, in particular human or humanized, as well as fragments, derivatives, and homologs of the antibodies described in the present invention and comprises a variable heavy chain sequence comprising CDRs being at least 80%, more in particular 90% or 95%, identical to the amino acid sequence of the CDRs of the variable heavy chain sequence of Factor VIIIKrix-1; and/or a variable light chain sequence comprising CDRs being at least 80%, more in particular 90% or 95%, identical to the amino acid sequence of the CDRs of the variable light chain sequence of Factor VIIIKrix-1.

According to a particular embodiment, d ligands used in the methods of the present invention are fragments and derivatives, including modified antibodies such as deglycosylated antibodies, in particular complementarity determining regions ("CDR's") of the herein described monoclonal anti-Factor VIII antibodies as well as homologs thereof.

A therapeutically effective amount as used herein means from about 1 microgram to about 10 milligrams per kilogram of body weight, more preferably from about 10 micrograms to about 1 milligram per kilogram of body weight of the mammal to be treated. It will be appreciated that, in view of the long half-life time of most IgG human antibodies, the ligands of the present invention which are monoclonal antibodies of the said class will enjoy a periodicity of treatment which participates in the comfort of the patient.

The present invention provides methods of treatment and prevention as well as pharmaceutical compositions for the treatment or prevention of a thrombotic pathological condition. Particular embodiments of the said thrombotic pathologic condition to be prevented or treated, include but are not limited to intravascular coagulation, arterial thrombosis (which may be responsible for acute myocardial infarction and stroke), peripheral artery disease, coronary arterial disease, arterial restenosis, venous thrombosis (which commonly occurs in peripheral veins as a consequence of accidental or surgical trauma or immobilization) or arteriosclerosis. When referring to the treatment or prevention of thrombotic pathological conditions, the disorders outlined herein above are thus envisaged A number of conditions are known to increase of the risk of thrombus formation such as arterial fibrillation, vascular interventions, mechanical heart valves, heart attack, unstable angina, acute ischemic stroke. Thus, it can be envisaged that the ligands or antibodies described herein are particularly suited for preventing a thrombotic pathological condition, when these conditions occur.

In a particular embodiment of the method of treatment of the present invention, the patient is provided with a bolus (intravenously injected) at a dosage determined by the ordinary skilled physician depending on criteria which establish the particular patient's clinical condition.

The method of treatment and/or prevention according to the invention may include further treatment or prevention of the same thrombotic pathologic condition by administrating, preferably by sequentially administrating, to the patient a therapeutically effective amount of a thrombolytic agent such as disclosed hereinabove under the heading of pharmaceutical compositions. Sequentially, as used herein, means that the ligand of the present invention and the known thrombolytic agent are administered to the patient sequentially but not simultaneously.

According to yet a further aspect, the present invention provides methods for the identification and/or selection of antibodies which are capable of partially inhibiting a wild type protein, more particularly Factor VIII, with the plateau effect described herein.

The conventional technique of immunizing an animal such as a mouse with a protein such as Factor VIII elicits an immunological response which may involve several epitopes on the Factor VIII molecule. Even when using specific antigens which are related to the activity of Factor VIII, the likeliness of obtaining an antibody which partially inhibits Factor VIII is limited. The present invention provides more selective methods of obtaining monoclonal antibodies capable of only partially inhibiting a wild-type protein. First, a donor, e.g. a mammal such as a human, is provided (i.e. selected) which has a partially functional, modified version of a wild-type protein. The said modification, which lies in a domain of the protein, may be due to any cause, e.g. race or variety, to genetic defects at birth, to an illness or by human interference, e.g. immunotolerance against the functionally modified version. The mammal donor is then administered the wild-type protein in order to elicit an immune response; at this stage, it is important that a sufficient quantity of the wild-type protein (e.g. Factor VIII) be administered until an immune response is generated in the mammal donor. Then, in a final step of the method, selection of B-cells from the mammal donor will result in a much greater chance of obtaining monoclonal antibodies against an epitope in the region of the modification, as this region of modification in the wild-type protein is recognized as foreign by the mammal host. As this region of modification is responsible for the partial inhibition of function of the protein in the mammal donor, it is likely that antibodies directed to this region in the wild-type protein will also affect the function of the protein. When applied to Factor VIII, this method will result in a greater chance of obtaining partially inhibitory antibodies to Factor VIII. Such a method of obtaining monoclonal antibodies from a non-human mammal against a domain of a protein thus comprises the steps of:

a) selecting a non-human mammal having a modified and at least partially functional (or partly physiologically active) protein, the modification being with respect to a wild type protein and lying in the relevant domain of the protein;
b) administering the wild type protein to the non-human mammal in order to elicit an immune response, and
c) selecting B-lymphocytes from the non-human mammal which produce antibodies which only partially inactivate the wild type protein.

According to this method, the standard practice is to sacrifice the non-human mammal and to remove its spleen in order to perform step (c).

The present invention additionally provides a method of obtaining monoclonal antibodies from the blood of a human being having a modified and (at least) partially functional physiologically active protein, the modification being with respect to a wild type protein and lying in a domain of the protein, and to whom the wild type protein was administered, the said method comprising the step of selecting, from the blood of said human being, B-lymphocytes which produce antibodies which only partially inactivate the wild type protein.

As described above, the present invention provides monoclonal antibodies directed to the C1 domain of Factor VIII and capable of partially inhibiting Factor VIII, whereby a number of specific antibodies are provided. Additionally, antibodies capable of competing with these partially inhibiting Factor VIII antibodies are also envisaged. Methods for identifying such antibodies capable of competing with the antibodies of the invention are known in the art. According to one embodiment of the invention, competing partially inhibitory Factor VIII antibodies are identified by a method which comprises the steps of contacting Factor VIII or a fragment of Factor VIII comprising the C1 domain with a first inhibitory antibody and a candidate inhibitory antibody, and assaying the capacity of said candidate antibody to compete with the binding of the Factor VIII inhibitory antibody said Factor VIII or fragment of Factor VIII. Said candidate antibody can be obtained by the methods described herein above or can be an uncharacterised antibody, which is part of a large pool of antibodies, each of which are screened by the competition assay. Alternatively, the uncharacterised antibody is first screened for its ability to bind factor VIII. This can be done for example by incubating the uncharacterized antibodies with factor VIII fixed on microtiter plates, whereafter labelled known Factor VIII inhibitory antibody, such as Krix-1, is added and assayed for its binding to Factor VIII. Alternatively, the known Factor VIII inhibitory antibody and the candidate antibody are mixed together before assaying the residual binding of the known inhibitory antibody to Factor VIII. In a particular embodiment of the invention the known inhibitory Factor VIII antibody used for the identification of novel, competing partially inhibitory antibodies is Krix-1 or RHD5, or fragments or derivatives thereof. According to a further particular embodiment of the invention the antibodies obtained in such a way are further screened for their Factor VIII inhibitory activity and for their plateau-effect.

The present invention thus also relates to (purified) antibodies obtained from this method which can be used in mixtures together with Krix-1, RHD5 or modified versions thereof according to the present invention and in the generation of pharmaceutical compositions.

The present invention, as embodied in the various above disclosed aspects, has a number of advantages. The major advantage of the therapeutic use of the human monoclonal antibodies of the invention is that the treatment is highly specific for the immune response under consideration. In hypercoagulation states, the specificity of the human monoclonal antibodies of the invention ensures that interaction within the coagulation cascade pathway is limited to the factor recognized by the antibody.

More specifically, the use of the anti-Factor VIII antibodies having the above-mentioned preferred characteristics brings a unique combination of the advantages related to the targeting of Factor VIII, those related to the characteristics of Factor VIII inhibition and those related to the use of antibodies:

- targeting Factor VIII means that neutralizing a co-factor activity such as that of Factor VIII carries no risk of completely inhibiting the enzymatic activity it enhances, thereby representing an advantage over methods targeting directly enzymes such as Factor IX.
- the embodiments of the inhibitors described above have in common that they efficiently but only partially inhibit the co-factor activity of Factor VIII, setting a therapeutically useful plateau, even when the monoclonal antibody of the invention is used in more than 100-fold excess. Monoclonal antibodies in accordance with the present invention achieve a plateau effect in inactivation of Factor VIII, allowing bolus application, yielding safe antithrombotic protection over several weeks without the need of monitoring or the risk of overdosage.
- where human IgG is used, an additional advantage is obtained. Human IgG antibodies exhibit a prolonged half-life time of three weeks (except for IgG3 which is one week), thus providing very stable plasma levels of the anti-thrombotic agent and allowing for a drastic reduction in the frequency of administration.
- Further, the use of human antibodies or derivatives carries a minimal risk of inducing immune responses.

The present invention relates to ligands or antibodies capable of partially inhibiting the activity of Factor VIII. As indicated herein, these are useful in the treatment of diseases in which the formation of blood clots is pathological. The effects of the reagents of the present invention on blood clotting is commonly evaluated using 'activated Prothrombin time' (aPTT).

The activated partial thromboplastin time (PTT) measures the clotting time from the activation of Factor XII, through the formation of fibrin clot. This measures the integrity of the intrinsic and common pathways of coagulation, whereas the prothrombin time (PT) measures the integrity of the extrinsic and common pathways of coagulation. PTT prolongations are caused by either factor deficiencies (especially of Factors VIII, IX, XI, and/or XII), or inhibitors (most commonly, lupus anticoagulants, or therapeutic anticoagulants such as heparin, hirudin, or argatroban). PTT results are reported as the number of seconds the blood takes to clot when mixed with a thromboplastin reagent. The normal values of aPTT range between around 25 to 35 seconds. In patients receiving anticoagulant therapy the aPTT value will be 1.5 to 2.5 times the control values. The International Normalized Ratio (INR) was created by the World Health Organization because PTT results can vary depending on the thromboplastin reagent used. The INR is a conversion unit that takes into account the different sensitivities of thromboplastins. The INR is widely accepted as the standard unit for reporting PT results.

The effectiveness of anticoagulants, more particularly coagulants taken orally, can vary over time, as changes in diet, (particularly foods high in vitamin K), alcohol use, other drugs and illness can all affect PTT. These factors require that the PTT is monitored regularly so the patient stays within the desired therapeutic range. Oral anticoagulant dosages are then adjusted according to the results of the PT test.

The present invention is further described by the following examples which are provided for illustrative purposes only. The Krix-1 antibody referred to herein above is also referred to as the KRIX-1 antibody hereunder.

EXAMPLE 1

Production of Monoclonal Antibodies Derived from Hemophilia A Patients

Human monoclonal antibodies of the desired specificity and characteristics are produced by transformation of B lymphocytes obtained from the peripheral blood of patients suffering from hemophilia A or acquired hemophilia. The method of selecting patients is an embodiment of the present invention. In order to elicit a more specific immunological response, patients are sought who have an impaired function of a physiologically active protein, e.g. Factor VIII. By "impaired" is meant that some residual function is available but that this is less than is known for the wild-type of the same protein. A comparison between the self-protein and the wild-type protein should exhibit a difference in the two proteins, preferably in a region or domain which is of interest. The difference may be a deletion or a substitution of one or more amino acids with others. The patients are then administered enough of the wild-type protein to elicit an immunological response. Then, B-lymphocytes are extracted from the patients and selected based on the production of antibodies which have desirable properties. Although reference is made to "patients" above, the method in accordance with this embodiment may be applied generally to mammals. The above procedure results in a greater chance of obtaining antibodies which target the domain containing the defect.

B cells are transformed by infection with the Epstein-Barr virus and activation of surface antigens using techniques well known by those skilled in the art. Cell supernatants containing appropriate antibodies are identified by a specific assay procedure such as described in more details hereinbelow.

Thus, antibodies towards Factor VIII are identified by reacting the supernatant with polystyrene microtitration plates coated with Factor VIII or with Factor VIII/von Willebrand factor complexes. The binding of specific antibodies is detected by addition of a non human IgG reagent coupled to an enzyme. Addition of an enzyme substrate which is converted to a colored compound in the presence of the enzyme allows the detection of specific antibodies. Such methods referred to as enzyme-linked immunoassays (ELISA) are well known to those skilled in the art and described in details e.g. in *Current Protocols in Immunology*, chapter 2, John Wiley & Sons (1994), the content of which is incorporated herein by reference.

Figure 1:
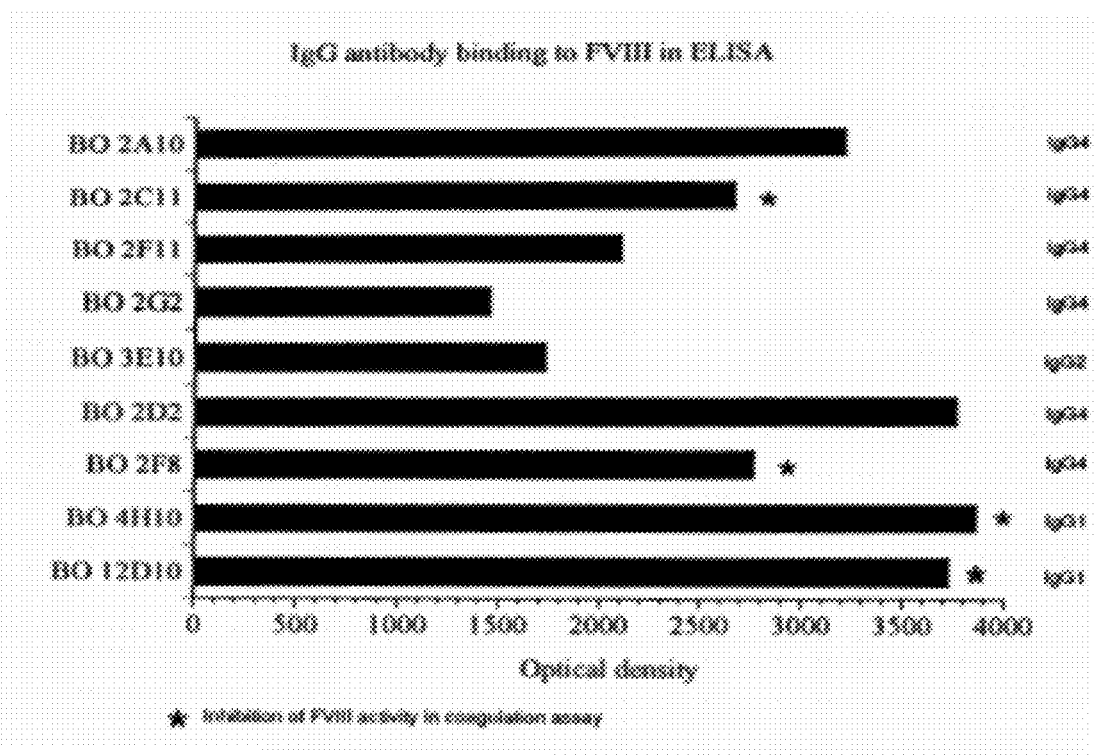
Figure 2:
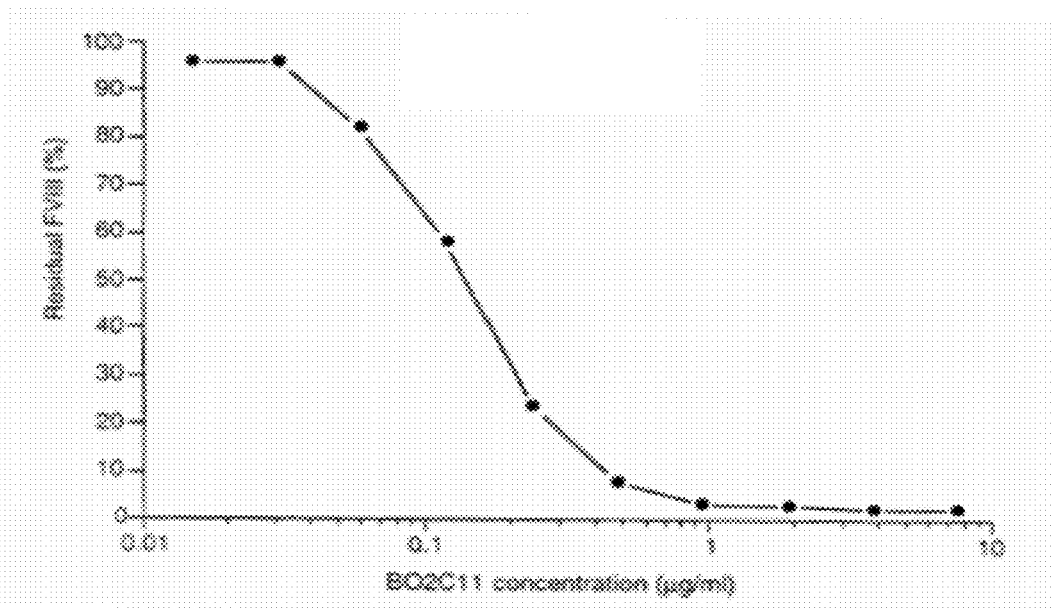

More specifically in the present case, the binding of anti-Factor VIII IgG antibodies was detected by addition of a horseradish peroxidase labeled mouse monoclonal antibody specific for human Fc gamma The IgG subclass of the anti-Factor VIII antibody was detected in ELISA, as presented in FIG. 1. The inhibition of Factor VIII functional activity was tested in a functional coagulation assay as follows. Equal volume of cell culture supernatant and of a pool of normal plasma were incubated for two hours at 37° C. and the residual Factor VIII activity measured thereafter. Those antibodies which significantly inhibit Factor VIII activity are shown with an asterisk in FIG. 1.

B cells (such as BO 2C11) producing anti-Factor VIII antibodies are then expanded and cloned by limiting dilution as described for instance in *Current Protocols in Immunology* (see supra). Anti-Factor VIII antibodies having the capacity to inhibit the procoagulant activity of Factor VIII as described above are identified using a chromogenic assay kit such as a Factor VIII chromogenic assay from Dade, Düchingen, Germany or Coatest® commercially available from Kabi Vitrum (Brussels, Belgium) or Chromogenix AB (Mölndal, Sweden).

Equal volumes of monoclonal antibodies BO 2C11 and a pool of normal blood plasma were incubated for 2 hours at 37° C. BO 2C11 concentrations before mixing are shown on the X axis. The reduction of Factor VIII activity was measured in a coagulation assay and was expressed as a percentage of the activity obtained in the absence of antibody (see FIG. 2). The residual activity goes to zero asymptotically (complete inhibition).

Figure 3:
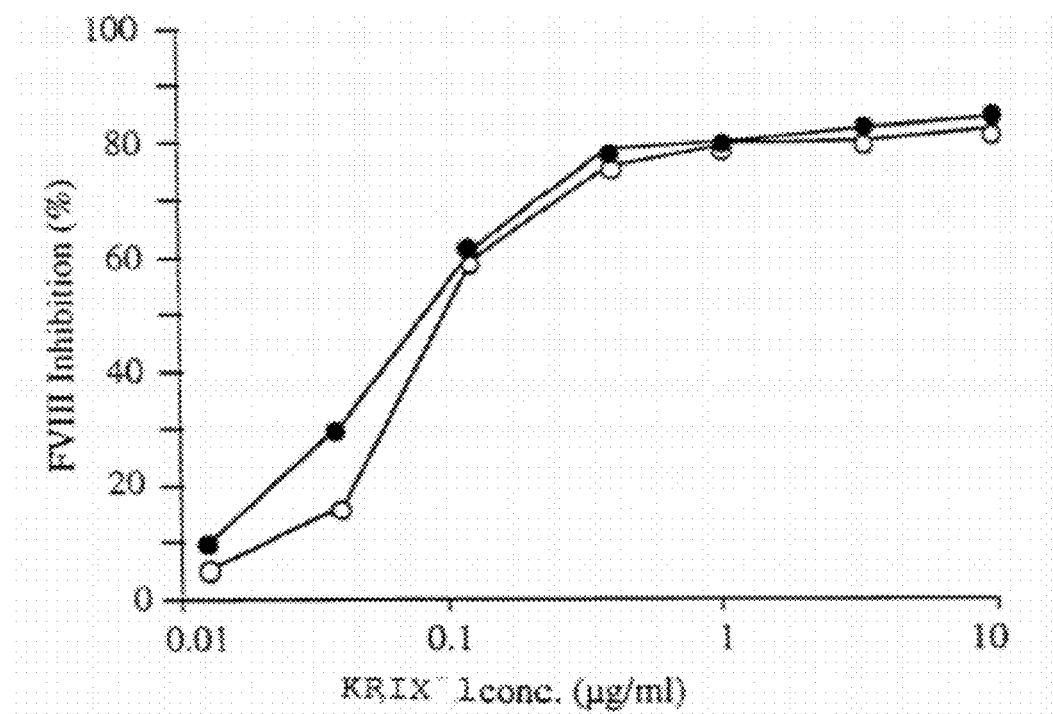

Antibodies which inhibit Factor VIII function with sufficient affinity but do not inhibit Factor VIII pro-coagulant activity completely, even when used in large antibody excess, were selected in a further embodiment of the present invention. A representative example of such an antibody is provided in FIG. 3 where, equal volumes of KRIX-1 and of recombinant Factor VIII or of normal plasma being incubated for two hours at 37° C. and concentrations (expressed in microgr/ml) of KRIX-1 before mixing with plasma being as indicated, the residual Factor VIII activity was measured using the above-mentioned chromogenic assay. FIG. 3 interestingly shows about 60% Factor VIII inhibition at a concentration of 0.1 microgr/ml and more interestingly an asymptotic Factor VIII inhibition of about 80% in the whole range of concentrations from 0.5 to 300 microgr/ml.

The thus selected antibodies are then produced in bulk culture and purified by affinity chromatography using methods well known to those skilled in the art.

The details of a non-limiting preparation technique are as follows. Human recombinant Factor VIII (specific activity: 4000 IU/mg) was obtained from Hyland (Glendale, Calif.) as material for laboratory use only; plasma-derived (pd) Factor VIII-von Willebrand factor complex, purified by ion exchange chromatography (specific activity ±160 IU/mg protein; 15:1 von Willebrand factor to Factor VIII w/w ratio), and purified Factor VIII-depleted von Willebrand factor (von Willebrand factor to Factor VIII w/w ratio 4800:1; lot 951016) were obtained from the Belgian Red Cross (Brussels, Belgium).

Peripheral blood samples were collected from donors suffering mild hemophilia and with inhibitors. The peripheral blood mononuclear cells (PBMC) were immortalized by EBV infection concomitantly to the activation of surface antigens. Four hundred and eighty cell lines were screened by ELISA for production of antibodies towards Factor VIII. For example, one cell line, named KRIX-1, was successfully cloned by limiting dilution. Clonality was verified by RT-PCR amplification of mRNA coding for the V regions of the antibody heavy and light chains: a single sequence was obtained from 10 clones of PCR products. Purified antibodies were obtained by passage of KRIX-1 cell culture supernatant on Protein-A Sepharose. An ELISA performed with IgG subclass-and light chain-specific antibodies identified KRIX-1 as an IgG4k.

Human monoclonal antibodies were purified by adsorption on immobilized Protein A (high-TRAP$^R$ Protein A; Pharmacia, Uppsala, Sweden). Fab fragments of human monoclonal antibody were prepared by papain digestion. One mg of a selected antibody was diluted to 500 microgr/ml in phosphate buffer (40 mmol/L $KH_2PO_4$, 60 mM $Na_2HPO_4$.2H2O, 0.15M NaCl) containing 50 mmol/L L-cystein (Sigma), 1 mmol/L EDTA (Merck) and 10 microgr papain (Sigma). The mixture was incubated for 3 h at 37° C. with continuous agitation. The reaction was stopped by addition of iodoacetamide to a final concentration of 75 mmol/L for 30 min at RT. The digested antibody was dialysed against phosphate-buffered saline (140 mmol/L NaCl, 67 mmol/L KCl, 20 mmol/L $Na_2HPO_4$, 4.4 mmol/L $KH_2PO_4$, pH 7.4). The undigested IgG and Fc fragments were then eliminated by passage over protein A sepharose (Hi Trap Protein A; Pharmacia). The Fab fragment was further purified by gel filtration chromatography on a Superdex 200 (Pharmacia).

Conventional methods were used for the detection of anti-Factor VIII IgG antibodies, the determination of IgG subclass, and the evaluation of inhibition of Factor VIII binding to von Willebrand factor. For the analysis of the inhibition of the binding of rFactor VIII to a selected antibody by Fab and native antibody, Maxisorb polystyrene plates (Nunc) were coated for 2 h with 50 µl of the antibody diluted to 5 microgr/ml in glycine-buffered saline (20 mmol/L glycine, 34 mmol/L NaCl, pH 9.2). After washing, 50 µl of biotin-labeled rFactor VIII diluted to 1 microgr/ml in Tris-casein (10 mmol/L tris (hydroxymethyl)-aminoethane, pH 7.3, containing 150 mmol/L NaCl and 0.5% casein) were mixed for 1 h at 37° C. with 50 µl of human IgG at various dilutions. A 50-µl aliquot of the mixture was added to the plates for 2 h at RT. After washing, the binding of biotinylated rFactor VIII was detected by sequential addition of avidin-peroxidase and OPD.

rFactor VIII (final concentration 0.2 microgr/mL) was incubated with human IgG antibody at different concentrations for 2 hours at 37° C. and the residual Factor VIII activity was assessed by a chromogenic assay (Coatest® Factor VIII, Chromogenix AB, Mölndal, Sweden or Kabi Vitrum, Brussels, Belgium) Inhibition of plasma Factor VIII activity was measured by the Bethesda method (Kasper et al. (1975) *Thromb Diath Haemorrh* 34, 612), in which a pool of normal plasma collected in buffered trisodium citrate was used as Factor VIII source. Residual Factor VIII activity was assessed by a chromogenic or by a one-stage clotting assay.

The Bethesda assay and residual activity measurement was performed as following: one volume of antibody at various dilutions in TBS (Tris 20 mM, NaCl 0.15 M, pH 7.4) was mixed with one volume of a pool of normal human plasma and incubated for 2 h at 37° C. The pool of normal plasma had been constituted by mixing plasma from 10 normal individuals and buffered by addition of Hepes (100 mM) to a final concentration of 10 mM. The residual Factor VIII activity was then measured using a modification of the DADE Factor VIII chromogenic assay (Dade A G, Marburg, Germany). In this assay, thrombin-activated Factor VIII accelerates the conversion of Factor X into Factor Xa in the presence of Factor IXa, PL and calcium ions; Factor Xa activity is then assessed by hydrolysis of a p-nitroanilide substrate. Reagents, which were reconstituted according to the manufacturer's instruction, comprised bovine Factor X (1 mM), Factor IXa (0.3 mM) and thrombin (0.3 mM); $CaCl_2$ (30 mM), PL (60 mM), a chromogenic Factor Xa substrate ($CH_3OCO$-D-CHG-Gly-Arg-pNA.AcOH; 3.4 mM), and a thrombin inhibitor (L-amidinophenylalanine piperidine). Aliquots of 30 µl of plasma/antibody mixture were retrieved at the end of the 2 h incubation period and displayed in microtitration plates; 30 µl of the Factor X and Factor IXa/thrombin reagents were added sequentially. After 90 sec, 60 µl of the chromogenic substrate was added and the incubation extended for 10 min at 37° C. The reaction was then blocked by addition of 30 µl citric acid (1 M), and OD was measured at 405 nm. The residual Factor VIII activity was determined by comparing the $OD_{405}$ nm of test samples with that obtained with Factor VIII solutions of known concentrations. The residual Factor VIII activity was expressed as the percentage of activity measured in plasma aliquots handled and diluted exactly as test samples throughout the entire experiment. Native KRIX-1 inhibited up to 90% of Factor VIII activity.

EXAMPLE 2

Production of Monoclonal Antibodies by Immunization in Animals

Alternatively, monoclonal antibodies having the same characteristics as disclosed in example 1 can be produced by on purpose immunization in animals. Thus, mice are injected with human Factor VIII in Freund's adjuvant Monoclonal anti-human Factor VIII antibodies are then obtained by fusion of spleen lymphocytes with a mouse myeloma cell line. Cell culture supernatants producing anti-Factor VIII antibodies are identified and cloned by limiting dilution, using methods described in *Current Protocols in Immunology* (see supra). Further selection of inhibitors having the desired capacity to inhibit the pro-coagulant activity of Factor VIII is carried out as described in example 1.

Monoclonal antibodies produced in mice are then humanized. Thus, sequences of the variable parts of mouse heavy and light chains are aligned with human immunoglobulin variable regions to identify human antibody with the greatest homology in framework regions. The DNA fragment encoding humanized variable regions are then synthesized by a PCR-based CDR (complementarity determining regions) grafting method as described for instance in Sato et al., *Cancer Research* (1993) 53:851-6. The final PCR product coding for the heavy chain variable part of the humanized antibody is digested and subcloned upstream of the human C gamma-1 gene in a first expression plasmid. The humanized light chain variable region of the final construction is inserted upstream of the C kappa gene in a second expression plasmid. The two constructions are then co-transfected into COS cells expression system.

EXAMPLE 3

Characterization of Anti-Factor VIII Antibodies

Figure 4:
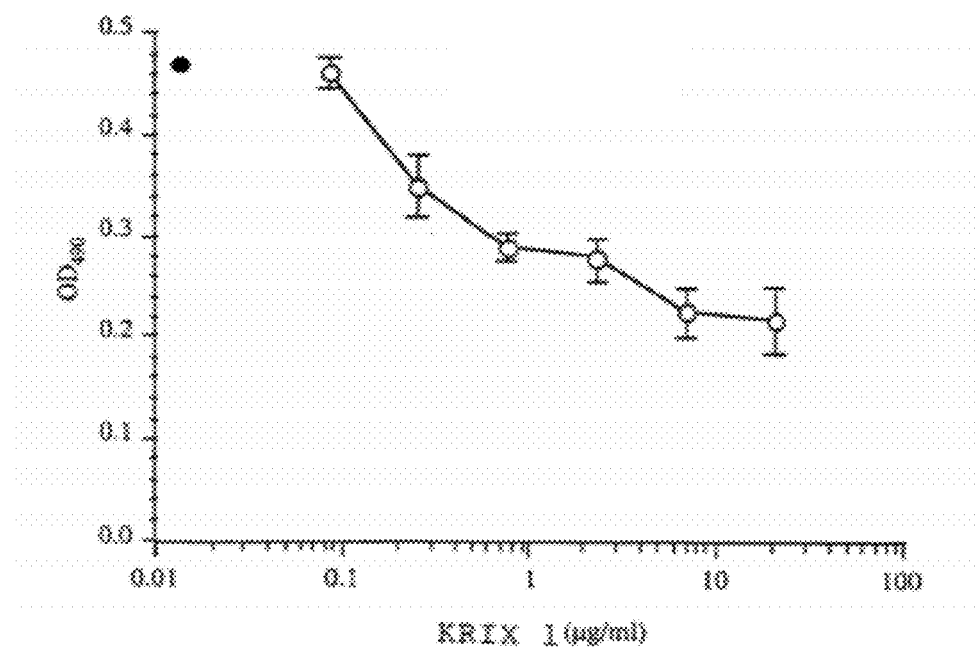

Monoclonal antibodies of either human (example 1) or animal (example 2) origin are characterized using an assay system by which their capacity to inhibit the binding of Factor VIII to phospholipids is evaluated. Thus, polystyrene microtitration plates are coated with phosphatidyl-L-serine. Soluble recombinant Factor VIII at 2 microgr/ml final concentration is mixed for 30 minutes at 37° C. with various concentrations of the antibody under evaluation. The mixture is then rapidly activated with thrombin and added to phosphatidyl-L-serine coated plates. The said plates were then incubated for two minutes at 21° C. and the binding of Factor VIII was detected by addition of the anti-Factor VIII A1 domain mAbF14A2, for two minutes, followed by a two minute incubation with HRP-conjugated goat anti-mouse Fc gamma Results of this experiment are shown in FIG. 4 for the monoclonal antibody produced from the cell line KRIX-1. On the figure, the average of activated Factor VIII binding in the absence (closed symbols) or presence (open symbols) of the antibody, as well as the standard deviation of triplicates are indicated. Controls in the absence of Factor VIII gave OD 490 lower than 0.05. FIG. 4 clearly shows that the monoclonal antibody produced from cell line KRIX-1 inhibits significantly the binding of Factor VIII to phospholipids but brings about incomplete inhibition even when added in large excess.

To demonstrate that in absence of plasma, KRIX-1 did not recognize the mutated Factor VIII light chain of the donor, DNA fragments encoding wild-type and mutated Factor VIII light chains were synthesized. The corresponding proteins were expressed in reticulocyte lysates. The correct folding of native and mutated light chains was determined by immunoprecipitation with the human monoclonal antibody BO2C11, which recognizes a conformational epitope within the carboxy-terminal part of the Factor VIII light chain Immunoprecipitation experiments indicated that BO2C11 bound wild-type and Arg2150His light chains, whereas KRIX-1 captured exclusively the wild-type light chain. Prolonged exposure of SDS-PAGE gels to the autoradiography film failed to detect any significant binding of KRIX-1 to the mutated light chain. Control experiments showed no binding to assay reagents other than Factor VIII or Factor VIII fragments, and preincubation with soluble rFactor VIII prevented the binding to methionine-labeled Factor VIII fragments, confirming the binding specificity.

KRIX-1 did not recognize Factor VIII in Western blotting indicating that the epitope recognized was conformational. Further epitope mapping was therefore performed with Factor VIII fragments produced in reticulocyte lysates. Preliminary experiments had indicated that such an approach was efficient for the synthesis of Factor VIII domains. The immunoprecipitation procedure using labeled Factor VIII domains produced in reticulocyte lysate was validated by mapping the epitope recognized by the human monoclonal antibody BO2C11. A complete agreement was observed between the binding to Factor VIII C2 deletion fragments produced in reticulocyte lysates and the binding to recombinant fragments produced in E. coli or COS cells. KRIX-1 bound to full-length light chain, to fragments corresponding to A3C1, C1C2, and the isolated C1 domain. In contrast, KRIX-1 did not bind to the C1 or C1C2 domains with the substitution Arg2150His, although in a control experiment, the Arg2150His C1C2 domain was bound by BO2C11 like its normal counterpart.

A search was made for other mutations in the light chain which could alter the binding of KRIX-1. As shown in Table 1, KRIX-1 inhibited the activity of all mutated Factor VIII molecules tested so far, except those carrying the mutation Arg2150His.

TABLE 1

Inhibition of Factor VIII activity in mild hemophilia A patients' plasma.

| Factor VIII mutation | Factor VIII activity (IU/ml) | KRIX-1 Inhibition (%) |
| --- | --- | --- |
| Arg1689Leu | 0.04 | >70 |
| Arg1749His | 0.39 | >70 |
| Gly1750Arg | 0.38 | >70 |
| Ala1824Val | 0.16 | >70 |
| Asp1825Gly | 0.17 | >70 |
| His1961Tyr | 0.24 | >70 |
| Arg1966Gln | 0.08 | >70 |
| Met2010Ile | 0.04 | >70 |
| Ser2011Asn | 0.23 | >70 |
| Val2016Ala | 0.05 | >70 |
| Asn2019ser | 0.13 | >70 |
| Leu2052Phe | 0.23 | >70 |
| Asp2074Gly | 0.13 | >70 |
| Thr2086Ile | 0.08 | >70 |
| Ile2098Ser | 0.20 | >70 |
| Phe2101Leu | 0.06 | >70 |
| Asn2129Ser | 0.20 | >70 |
| Arg2150His | 0.03 | 0 |
| Pro2153Gln | 0.02 | 65 |
| Arg2159Leu | 0.16 | >70 |
| Trp2229Cys | 0.02 | >70 |
| Gln2246Arg | 0.08 | >70 |

In the use of KRIX-1 as a medicament to partially inhibit Factor VIII mild mutations of Factor VIII will not affect the effectiveness of the therapy.

KRIX-1 inhibited the binding of Factor VIII to von Willebrand factor in a dose-dependent manner. The concentration of KRIX-1 required to achieve 50% inhibition ($IC_{50}$) of Factor VIII binding was 0.25 microgr/mL and more than 95% inhibition was obtained with 20 microgr/mL of KRIX-1. Fab fragments of KRIX-1 also inhibited Factor VIII binding to von Willebrand factor. However, on a molar basis 15 times more Fab than native KRIX-1 was required to inhibit 50% of Factor VIII binding to von Willebrand factor. Additional experiments were performed to exclude that the KRIX-1 Fab fragments still contained intact or partially digested antibody. SDS-PAGE analysis of the Fab fragments purified by protein A adsorption and gel filtration chromatography showed a single band. The presence of trace amounts of Fc gamma fragments remaining bound to Fab fragments was excluded in ELISA. Wells with insolubilised Factor VIII were incubated with native or Fab KRIX-1. Binding of both Fab and native KRIX-1 could be detected by addition of peroxidase-labeled anti-kappa light chain IgG. By contrast, addition of peroxidase-labeled anti-Fc gamma IgG did not reveal any specific binding even when 100 microgr/ml of the Fab preparation were incubated into the wells. By comparison, the addition 0.1 microgr/ml of the native antibody gave rise to a significant binding. In ELISA, a 15-fold higher concentration of Fab than of native antibody was required to inhibit 50% of the binding of biotinylated KRIX-1 onto insolubilised Factor VIII, indicating that the Fab KRIX-1 fragment had a lower affinity for Factor VIII than the native antibody. Accordingly, the requirement for higher concentrations of KRIX-1 Fab than of native antibody to inhibit Factor VIII binding to von Willebrand factor should be attributed to the reduced affinity of KRIX-1 Fab fragments for Factor VIII.

To determine whether KRIX-1 was representative of the polyclonal antibodies from the donor, a competitive assay was used. The binding of biotinylated KRIX-1 to insolubilised Factor VIII was measured in presence of increasing concentrations of either KRIX-1, polyclonal IgG from the donor, or control polyclonal IgG. IgG from the donor dose-dependently inhibited KRIX-1 binding to Factor VIII. The concentration of KRIX-1 and IgG from the donor inhibiting 50% of biotinylated KRIX-1 on Factor VIII were of 0.3 microgr/ml and of 170 microgr/ml, respectively, whereas no inhibition was observed with the control IgG.

EXAMPLE 4

Figure 5:
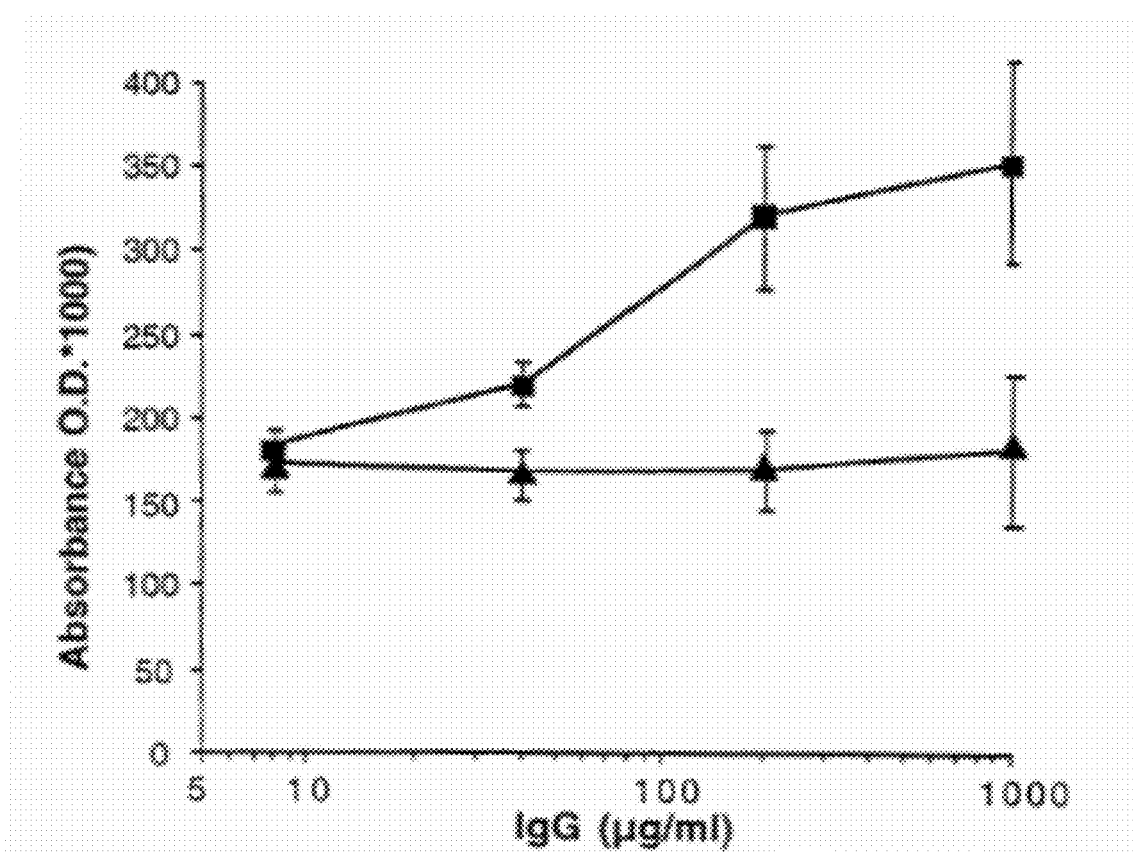

Production of Monoclonal Antibodies Derived from Hemophilia A Patients and which Bind to the Factor VIII—von Willebrand Factor Complex Alternatively, antibodies which reduce the release rate of Factor VIII from von Willebrand factor are identified as follows. Polystyrene microtitration plates are coated with a specific antibody to von Willebrand factor. A solution of biotinylated recombinant Factor VIII (0.5 microgr/mL) complexed to von Willebrand factor (5 microgr/mL) is mixed with various concentrations of IgG from a donor (FIG. 5 solid squares), e.g. the same patient as described above (from which KRIX-1 was derived), MoAb4H1D7, or of IgG from a non-hemophiliac subject (FIG. 5 solid triangles). IgG at the indicated concentrations was added to microtitration plates coated with a mouse antibody, MoAb4H1D7 against von Willebrand factor for an incubation of two hours at room temperature. After washing, Factor VIII was activated by thrombin during two minutes at 37° C. Factor VIII bound to von Willebrand factor was detected by addition of avidine peroxidase. Controls included the detection of bound biotinylated Factor VIII in the absence of thrombin digestion (OD450=460+47.7SD) and of biotinylated recombinant Factor VIII after thrombin digestion in the absence of antibody (OD450=160+16.0SD).

Results of these experiments are shown in FIG. 5 for polyclonal antibodies. On this figure, the average values as well as the standard deviation of triplicates are indicated. FIG. 5 clearly shows that a significantly higher proportion of activated Factor VIII remains bound to the plate in the presence of increasing concentrations of the antibody, i.e. it demonstrates a reduction of the dissociation of activated Factor VIII from von Willebrand factor in the presence of an inhibitor antibody recognizing Factor VIII bound to von Willebrand factor. Monoclonal antibodies have been obtained from these polyclonal antibodies in accordance with the methods described in this invention, thus indicating that the present invention may be extended to monoclonal antibodies and fragments and derivatives thereof which bind to Factor VIII/von Willebrand factor complexes.

EXAMPLE 5

Sequencing of Antibody Variable Domains

Sequencing of antibody variable domains was carried out as follows. The isolation of RNA from EBV-immortalized human B-cell lines was performed using TRIzol Reagent according to the manufacturer's instructions (Life Technologies). CDNA was synthesized with the SuperScript preamplification system for first-strand cDNA synthesis. The cDNA encoding the heavy chain variable region genes ($V_H$) was amplified by polymerase chain reaction (PCR) using primers specific for the leader sequence of the $V_H$ families and for the first exon of the C gamma region, as described (Bakkus et al, *Blood,* 80:2326, (1992)) Annealing was performed at 60° C. for 40 PCR cycles. PCR products of the appropriate size (460 bp) were isolated from 1.5% agarose gel and cloned using the TA Cloning Kit (Invitrogen BV, Leek, The Netherlands). A PCR screening using couples of primers corresponding to the $V_H$ gene family of interest was performed on cultures of randomly selected colonies. Plasmid DNA from positive colonies were isolated using Wizard Plus Minipreps (Promega, Menlo Park, Calif.) and sequenced in both directions with Sequenase (US Biochemical, Cleveland, Ohio), according to the manufacturer's instructions. Analysis of the variable gene sequences was made using the V BASE Sequence Directory (Tomlinson et al, MRC Centre for Protein Engineering, Cambridge, UK).

The complete sequences of the $V_H$ and $V_L$ of the antibody BO 2C11 described in example 1 were submitted to the EMBL Nucleotide Sequence Database under the accession numbers AJ224083 and AJ224084, respectively.

The amino acid sequences shown in FIGS. 6 and 7 define the VH and VL regions of the antibody BO2C11 including the three CDR's for each of the heavy and light chains. Also given are the polynucleotide sequences which encode for these regions. SEQ. ID NOs. 46 and 48 provide the amino acid sequences of the heavy and light chains of BO2C11, respectively while SEQ. ID NOs. 45 and 47 provide the polynucleotide sequences coding for these variable regions.

The amino acid sequences shown in FIGS. 8 and 9 define the VH and VL regions of the antibody KRIX-1 including the three CDR's 1-3 for each of the short and long chains. Also given are the polynucleotide sequences which encode for these regions. SEQ. ID NOs. 2 and 4 are the amino acid sequences of the heavy and light chains of KRIX-1, respectively while SEQ. ID NOs. 1 and 3 provide the polynucleotide sequences coding for these variable regions. The amino acid sequences which define the CDR1, CDR2 and CDR3 of the variable heavy chain of KRIX-1 are provided as SEQ ID NOs 33, 34 and 35. The amino acid sequences which define the CDR1, CDR2 and CDR3 of the variable light chain of KRIX-1 are provided as SEQ ID NOs 36, 37 and 38.

EXAMPLE 6 (Comparative)

Inhibition of Factor VIII Activity by the Antibody SAF8C-Ig

Figure 10:
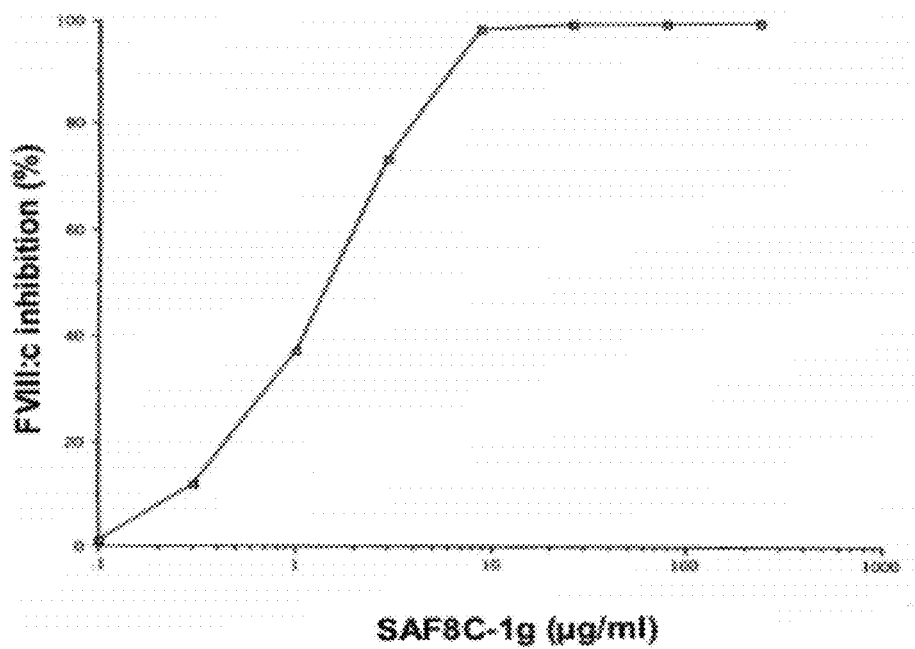

Levels of Factor VIII are measured in a functional assay following an incubation period of two hours at 37° C. with various concentrations of the antibody SAF8C-Ig, using the chromogenic assay described in example 1. As shown in FIG. 10, the residual Factor VIII activity is reduced in a dose dependent manner. Already at 100 microgr/ml of SAF8C-Ig, residual Factor VIII activity is less than 1% of the normal activity. Such low Factor VIII levels expose the patient to a high risk of spontaneous bleedings, as is well known for instance from Levine, *Ann. NY Acad. Sci.* (1975) 240:201 and Gilbert, *Mount Sinai J. Med.* (1977) 44: 339.

EXAMPLE 7

Inhibition of Venous Thrombosis in Hamsters by KRIX-1

Figure 12:
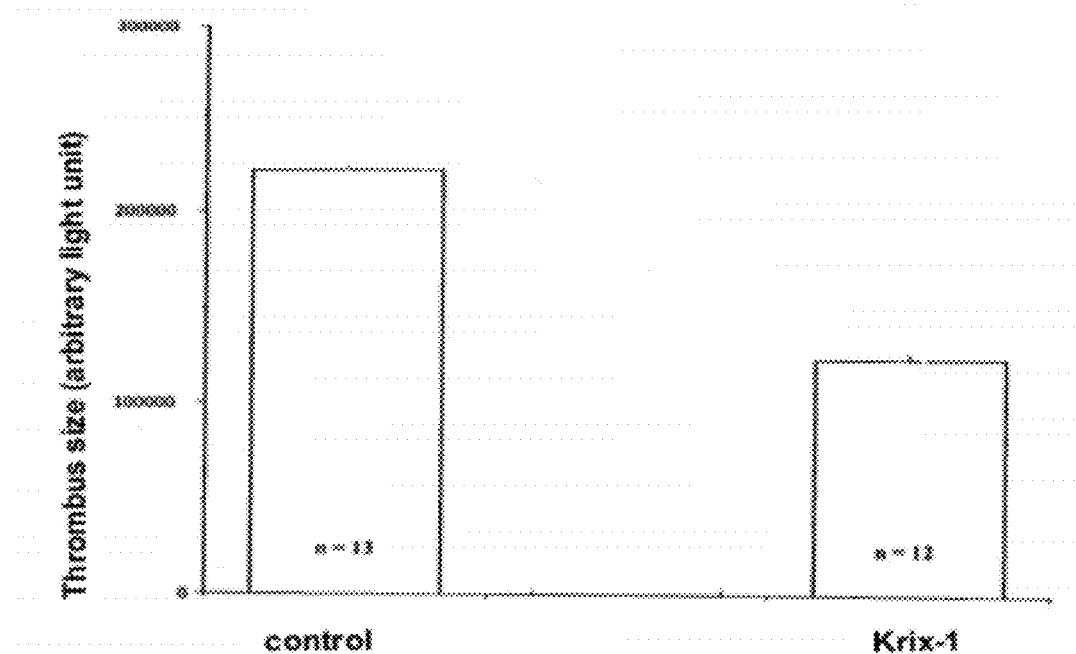
FIG. 12 illustrates the inhibition of venous thrombosis in a hamster model by KRIX-1.

Thrombosis was experimentally induced in the femoral vein of anesthetized hamsters, by injecting the dye rose-bengal in the jugular vein and by exposure of the femoral vein to the green light of a Xenon lamp for 4 minutes (Kawazaki et al. *Thromb Haemost* (1999) 81: 306-11). As a consequence of illumination of the vessel, the dye decomposes and generates radicals injuring the vessel endothelial cells. Thus, subendothelial structures are exposed to the blood circulation and thrombus formation is initiated. The amount of thrombus formed is measured via transillumination of the injured vessel (Kawazaki et al. *Thromb Haemost* (1999) 81: 306-11) and is quantified via the amount of white light being transilluminated through the vessel. As represented in FIG. 12, when this experiment is performed in control animals, the average thrombus size measured in 13 hamsters is 220,000±32,575 (mean±SEM) Arbitrary light Units (A.U.), whereas treatment of a group of 12 hamsters with KRIX-1 (400-800 microgr/kg, given as a bolus immediately prior to induction of thrombosis) reduced the mean thrombus size to 122,000±27,100 A.U. (p=0.0188, Mann-Whitney test).

Figure 11:
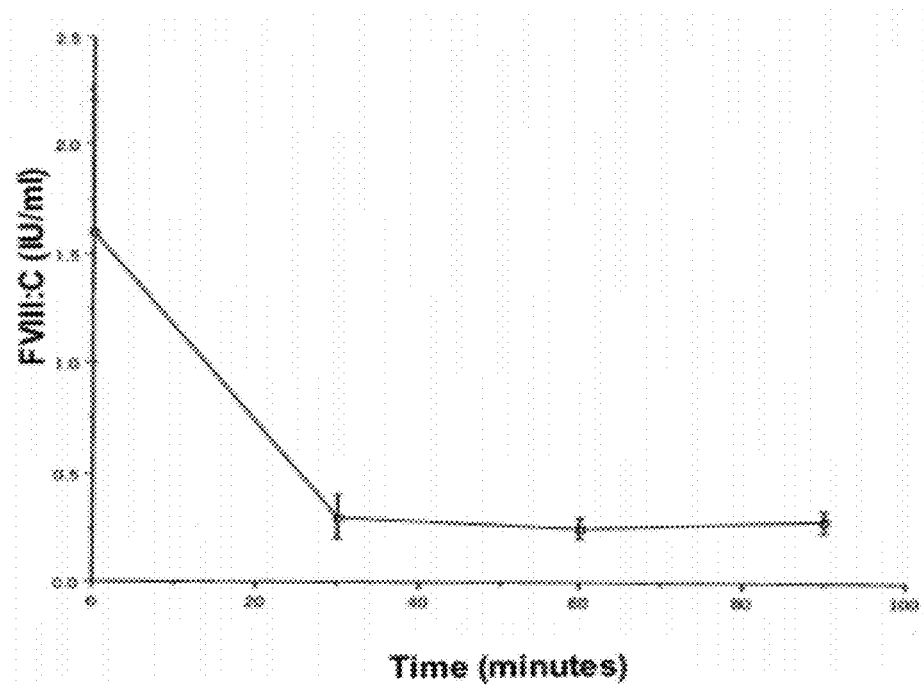
FIG. 11 illustrates the kinetics of Factor VIII inhibition by KRIX-1.

Additionally, the kinetics of Factor VIII inhibition by KRIX-1 was analyzed ex-vivo as follows: hamsters were injected intravenously with KRIX-1 (1600 microgr/kg). Levels of Factor VIII:c were measured in a chromogenic assay (Coatest Factor VIII$^R$ (Chromogenix A B, Mölndal, Sweden), and Factor VIII Chromogenic Assay (Dade, Düdingen, Switzerland)) using plasma collected before and at different periods of time after injection. FIG. 11 shows that in these hamsters, Factor VIII activity is reduced from 1.6 IU/ml to 0.3 IU/m1 already 30 minutes after antibody injection, thus confirming that KRIX-1 only partially inhibits Factor VIII.

EXAMPLE 8

Competition Between the Human Monoclonal Antibody RHD5 and KRIX-1

The human lymphoblastoid cell line RHD5 was derived by immortalisation of B lymphocytes from a patient who developed an autoimmune response to Factor VIII, according to described procedures (Jacquemin et al. (1998), Blood 92, 496-506). Briefly, $10^7$ peripheral blood mononuclear cells were resuspended in 2 ml culture medium and incubated for 2 hours at 37° C. with 200 µL Epstein-Barr virus supernatant (B95-8 strain). Cells were then seeded at 5,000 cells/well in 96-well microtiter plates (Nunc) containing feeder cells (3T6-TRAP cells irradiated with 7,000 rads). One hundred fifty microliters of culture supernatant was replaced every week by fresh culture medium. After 6 weeks, culture supernatant were tested in enzyme-linked immunosorbent assay for the presence of anti-Factor VIII antibodies. Positive cell lines were transferred to 24-well plates and immediately cloned at 60 cells per 96-well plate without feeder cells. One clone, producing an antibody called RHD5, was selected.

This cell line producing the monoclonal antibody RHD5 was deposited with the BCCM/LMBP (Belgian Co-ordinated Collections of Microorganisms/Plasmid Collection) Laboratorium voor Moleculaire Biologie, University of Ghent, Technologiepark 927, B-9052 Zwijnaarde, Belgium in August 2004, with the D. Collen Research Foundation (Onderwijs & navorsing, Campus Gasthuisberg, Herestraat 49, B-3000 Leuven, Belgium) as depositor (accession number LMBP 6165CB).

The sequencing of the rearranged immunoglobulin genes coding for RHD5 was performed as described in Jacquemin et al. (1998), Blood 92, 496-506.

The nucleotide and amino acid sequences of the variable regions of RHD5 heavy and light chain are listed in SEQ ID Nos 29 to 32. It was determined that RHD5 is an IgG1.

The antibody present in the culture supernatant was purified by adsorption on HiTRAP protein A (Pharmacia).

The inhibitory activity of RHD5 was assessed in a Bethesda assay (Kasper et al. (1975), cited supra) as described in example 1. RHD5 inhibited only partially Factor VIII activity up to the highest concentration tested. In a Bethesda assay performed by mixing one volume of antibody at 200 microgram/ml or of control buffer with one volume of plasma, the residual Factor VIII levels were 7.0±0.2 and 251.9±18.8 ng/ml, respectively (mean±SD of triplicates). The inhibition of Factor VIII activity reached at a final concentration of RHD5 of 100 microgram/ml was therefore 97%. Similarly, in a Bethesda assay performed by mixing one volume of antibody at 200 microgram/ml or of control buffer with one volume of full length recombinant Factor VIII (Recombinate$^R$, Baxter), the residual Factor VIII levels were 8.0±0.2 and 399.7±18.8 ng/ml, respectively (mean±SD of triplicates). The inhibition of Factor VIII activity reached at a final concentration of RHD5 of 100 microgram/ml was therefore 98%. A dose response curve of plasma Factor VIII inhibition by RHD5 is shown in FIG. 15.

The ability of RHD5 to compete with vWF for Factor VIII binding was tested in ELISA (FIG. 16). Microtitration plates were incubated overnight at 4° C. with the anti-vWF MoAb4H1D7 (Jacquemin et al., Blood: 1998, 92: 496) diluted at 4 µg/ml. After washing the plates, 50 µl of a normal human plasma pool was added for 1 hour at RT. The plates were then washed and then incubated for 30 minutes with 50 µl of 400 mM CaCl2 to detach Factor VIII from vWF. Fifty microliters of biotinylated recombinant Factor VIII diluted at 0.4 µg/ml in PBS-BSA was mixed with 50 µl RHD5 at different dilutions. The mixture was incubated for 30 min at 37° C. before adding a 50 µl to the plate for 2 hours at room temperature. After washing, bound Factor VIII was detected by addition of avidin-peroxidase followed by ortho-phenylenediamine (OPD) and the optical density (OD) was measured at 490 nM.

The ability of KRIX-1 to compete with RHD5 for Factor VIII binding was tested in ELISA. Polystyre microtitration plates were incubated overnight at 4° C. with 50 µL RHD5 at 2 microgram/ml in phosphate buffered saline (PBS). The plates were washed 4 times with PBS-Tween. Biotinylated recombinant Factor VIII (0.5 microgram/ml) in Tris-BSA-Tween was mixed with RHD5 or KRIX-1 at various concentrations before addition to RHD5 coated plates.

After a two hours incubation period at 4° C., the plates were washed 4 times and bound biotinylated Factor VIII was detected by addition of avidine peroxidase (Sigma) at 1 microgram/ml. After 30 min at RT, the plates were washed again and supplemented with 100 µL OPD. The resulting OD was read at 490 nm in a Emax Microplate Reader (Molecular Devices, Menlo Park, Calif.).

Biotinylated Factor VIII used in the above experiment was prepared by incubating recombinant Factor VIII (100 microgram/ml) dialysed in Hepes buffer (Hepes 10 mM, NaCl 0.15 M, CaCl2 10 mM, pH 8.5) with sulfo-NHS-LC-biotin (Pierce) at 1 microgram/ml for 2 hours at RT. The preparation was then dialysed against Hepes buffer and stored and −80° C.

As shown in FIG. 13, KRIX-1 was able to completely prevent Factor VIII binding to RHD5. This competition between KRIX-1 and RHD5 shows that mixing the two antibodies in different ratios will allow the production of antibody mixtures with inhibitory activity ranging between the inhibitory activity achieved with KRIX-1 (85%) and that achieved with RHD5 (97-98%).

EXAMPLE 9

KRIX-1 and RHD5 Epitope Mapping

The specificity of RHD5 was further evaluated in an immunoprecipitation assay using radiolabelled recombinant Factor VIII fragments as described in Jacquemin et al., Blood (2000), 95:156-163.

Radiolabelled native Factor VIII C1 domain and mutant C1 domain carrying the substitution Arg2150His were incubated with human mAbs RHD5 and KRIX-1 bound to protein A sepharose. After washing, the bound material was eluted by boiling in SDS-buffer. The radioactivity of bound material was measured using a scintillation counter (A) or analysed by SDS-PAGE followed by autoradiography (B). Controls included a human mAb, BO2C11, directed toward the Factor VIII C2 domain and normal human plasma (H. plasma).

Expression of Factor VIII recombinant fragments in reticulocyte transcription/translation system Five hundred ng to 1 µg of DNA, linearised by NotI digestion, was used as a template in a T7 RNA polymerase transcription system in micrococcal nuclease-treated reticulocyte lysates (Promega, Southampton, UK) according to the manufacturer's instructions in the presence of L-[$^{35}$S]methionine (Amersham, Bucks, UK). The [$^{35}$S]-methionine labeled Factor VIII fragments migrated on SDS-PAGE as bands matching the expected mass of corresponding Factor VIII polypeptides.

Immunoprecipitation of L-[$^{35}$S]methionine-labeled Factor VIII fragments

One to three µL of standard in vitro translation product was added to 500 µL human antibody at 2 µg/mL in NET-gel buffer (50 mM Tris-HCl, pH 7.5; 150 mM NaCl; 0.1% Nonided NP-40; 1 mM EDTA (pH 8); 0.25% gelatin and 5% BSA). Tubes were gently rocked for 1hour at 4° C. Twenty µL of a 50% solution of Protein A Sepharose was then added to the antigen/antibody mixture, and incubated for 1 hour at 4° C. on a rocking platform. The Sepharose beads were centrifuged and washed twice with Tris-NP40 (10 mM Tris-HCl (pH 7.5); 0.1% NP40). Bound antigen/antibody complexes were eluted from the beads by boiling for 4 minutes in 30 µL of SDS gel loading buffer. The radioactivity of eluted material was measured using a scintillation counter. In addition, an aliquot of 15 µL was analysed by 10% (w/v) polyacrylamide gel electrophoresis and visualized by autoradiography. Control experiments were performed with the human monoclonal antibody BO2C11, directed towards the Factor VIII C2 domain (Jacquemin et al., Blood (1998), 92: 496-506) and normal donor's polyclonal IgG antibodies purified on Protein A Sepharose.

KRIX-1 and RHD5 bound the isolated C1 domain (FIG. 17). By contrast, as shown in FIG. 17, neither KRIX-1 (LE2E9) nor RHD5 bound to the C1 domain with the substitution Arg2150His. In a control experiment, the C1 domain was not captured by the mAb BO2C11 recognising the C2 domain (Jacquemin et al. (1998) 92: 496-506) nor by control polyclonal antibodies.

EXAMPLE 10

Effect of RHD5 on Bleeding After Tail Cutting in Wild-Type Mice

The risk of severe bleeding associated with high concentrations of mAb-RHD5 in plasma was evaluated in a tail cutting experiment. This assay is based on the observation that section of the distal portion of the tail results in important blood loss leading to death in most Factor VIII deficient mice (Bi et al. Nat Genet. (1995) 10:119-2) whereas normal mice or animals with low Factor VIII levels survive. This procedure allows an in vivo evaluation of Factor VIII activity.

In a preliminary experiment, we compared Factor VIII inhibition by mAb-RHD5 in human and mice plasma. One volume of mice plasma or of human plasma was mixed with one volume of mAb-RHD5 at 10 µg/ml in 0.15 M NaCl, 0.5% bovine serum albumin, 50 mM Tris(hydroxymethyl)-aminomethane, pH 7.2. After a 2 h incubation period at 37° C., the residual Factor VIII activity was measured with a Factor VIII chromogenic assay (Dade Behring, Marburg, Germany) according to the manufacturer recommendations. MabRHD5 inhibited 80% Factor VIII activity in human plasma but did not inhibit Factor VIII activity in mice plasma. By contrast, mAb-RHD5 inhibited recombinant human Factor VIII added to plasma of Factor VIII deficient mice. Because mAb-LE2E9Q did not inhibit mice Factor VIII, a tail clipping experiment could not be performed in wild type mice. The experiment was therefore performed in Factor VIII deficient mice in which normal Factor VIII levels had been obtained by administration of recombinant human Factor VIII.

Factor VIII deficient mice (n=6) were injected intravenously with 10 IU recombinant human Factor VIII and 10 min later with 100 µg mAb-RHD5. A 7-mm section of the tail was cut 30 minutes later and survival rate monitored over the subsequent 24 hours. A group of 6 Factor VIII deficient mice was used as control. After 24 h, 5 mice were dead in the control groups whereas all animals that had received recombinant human Factor VIII followed by mAb-RHD5 administration survived. This experiment demonstrated that in vivo RHD5 only partially inhibits the Factor VIII, even when the antibody is in large excess (100 µg antibody for about 2 µg recombinant human Factor VIII).

EXAMPLE 11

Identification of Alternative Inhibitory Antibodies to Factor VIII

The present example describes how, starting from a first inhibitory antibody such as KRIX-1, additional partially inhibitory antibodies can be identified, based on the fact that they compete with binding of a first inhibitory antibody such as KRIX-1 to Factor VIII. The procedure described below can be performed similarly using RHD5 in stead of KRIX-1 as a first inhibitory antibody. Similarly, the first inhibitory antibody used in these assays can be a glycosylated, partially glycosylated or completely degylosylated (extensive enzymatic treatment or site directed mutagenesis at essential positions in the glycosylation consensus sequence) of RHD5 or KRIX-1, provided that said antibody is still capable of binding to KRIX-1 and of partially inhibiting the activity of Factor VIII.

An example of an assay to identify further inhibitory antibodies is one wherein labelled KRIX-1 (radioactive labelled or labelled with biotin or with a chromophoric group) is bound to Factor VIII. Uncharacterised antibodies are then screened for their ability to disrupt the binding of KRIX-1 to Factor VIII. A large number of uncharacterized antibodies can be screened simultaneously.

Alternatively the uncharacterised antibodies are first incubated with Factor VIII insolubilised on microtiter plates, whereafter labelled KRIX-1 is added and assayed for its binding to Factor VIII. Alternatively, KRIX-1 and the uncharacterized antibody are mixed together before assaying the residual binding of KRIX-1 to Factor VIII.

Using these assays, antibodies which impair the binding of KRIX-1 to the C1 domain of Factor VIII can be identified. This impairment can be achieved by an antibody directed to the same epitope in the C1 domain as for KRIX-1, by an antibody directed to another epitope that the one of KRIX-1 in the C1 domain, or by antibody with an epitope outside the C1 domain but which sterically competes with the binding of KRIX-1 antibody to its epitope in the C1 domain.

The screening for antibodies can for example be initiated by screening in first instance a scFv library for scFv fragments that bind to human Factor VIII and more particularly bind to the C1 domain of Factor VIII. For this technique, antibody fragments have been displayed on the surface of filamentous phage that encode the antibody genes (Hoogenboom and Winter (1992) *J Mol Biol.* 227, 381-388; Vaughan et al. (1996) *Nat. Biotechnol.* 14, 309-314; Tomlinson et al. (1992) *Hum Mol Genet.* 3, 853-860; Nissim et al. (1994) *EMBO J* 13, 692-698; Griffiths et al. (1994) *EMBO J.* 12,725-734). Variable heavy chain (VH) and variable light chain (VL) immunoglobulin libraries can be developed in phages. These phages can then be selected by panning with antigen (Factor VIII, or the C1 domain of Factor VIII). The encoded antibody fragments can then be secreted as soluble fragments from infected bacteria. This display of antibodies on phages and the selection with antigen mimics immune selection and can be used to make antibodies without immunization starting from a single library of phages (Hoogenboom and Winter (1992) *J Mol Biol.* 227, 381-388). Alternatively, the phages can be selected by panning with the first inhibitory antibody. A human synthetic VH and VscFv library has been made by recloning the heavy and light chain variable regions from the lox library vectors, wherein the heavy and light chain V-genes were shuffled at random and cloned for display as single-chain Fv (scFv) fragments on the surface of filamentous phage (Griffiths et al. (1994) *EMBO J.* 12,725-34) [Centre for Protein Engineering of Dr. G. Winter, LMB-MRC, Cambridge, UK] into the phagemid vector pHEN2.

Depending on the selection criteria used in the first step, antibody fragments can be identified which bind to the C1 domain of Factor VIII or which compete with the binding of an antibody such as KRIX-1 to Factor VIII. Hereafter, these fragments can be screened for ability to compete with the binding of a first inhibitory antibody or their affinity of binding to Factor VIII, respectively. Subsequently, they can be tested for their ability to inhibit Factor VIII activity and for the presence of a plateau effect of Factor VIII inhibition at a molar excess.

Considering the size of the fragments, it is envisaged that enlarging the size of these fragments, by cloning these scFv fragments into a complete antibody, will result in an increased inhibitory activity.

Alternatively, the identification of further inhibitory antibodies is done by screening antibodies isolated from one or more hemophilia patient(s) or by screening antibodies obtained by traditional immunization with Factor VIII or a fragment thereof comprising the C1 domain. These antibodies can also be tested in the competition assay described above.

Antibodies or fragments which have been obtained using the above mentioned assay are tested for their inhibitory effect on Factor VIII activity and/or for their capacity to disrupt a complex between Factor VIII and e.g. vWF. Further, inhibitory antibodies or fragments are then screened for the presence of partial Factor VIII inhibition at physiological excess ("plateau effect").

Further to obtaining these alternative inhibitory antibodies and/or antibody fragments it can be envisaged to modify the glycosylation of the antibodies in accordance with the invention.

Any second antibody which competes with KRIX-1 binding can be used in mixtures together with at least one other antibody which competes with the binding of native KRIX-1, including KRIX-1 itself or a fragment of native KRIX-1, or a modified version of KRIX-1 or a fragment thereof, more particularly a KRIX-1 or fragment thereof with a modified glycosylation, which mixtures have a resulting Factor VIII inhibitory activity which is an intermediate between the inhibitory activity of each of the at least two antibodies in the mixture (see also example 14 below). Alternatively, the mixtures with intermediate partial inhibitory activity can be obtained by combining at least two antibodies or fragments thereof capable of binding to the C1 domain and capable of competing with the binding of antibody RHD5 to Factor VIII.

EXAMPLE 12

Effect of Deglycosylation on Factor VIII Inhibition by KRIX-1

KRIX-1 (0.5mg/ml in PBS) was mixed with N-glycosidase-F (roche diagnostics Gmbh, Mannheim, Germany) at final concentration of 2 U/ml. The mixture was incubated at 37° C. during 72 hours under gentle stirring.

The inhibitory activity of native and deglycosylated KRIX-1 was assessed in a Bethesda assay (Kasper et al. (1975), cited supra). Therefore, one volume of antibody at various dilutions in TBS (Tris 20 mM, NaCl 0.15 M, pH 7.4) was mixed with one volume of a pool of normal human plasma and incubated for 2 h at 37° C. The pool of normal plasma had been constituted by mixing plasma from 10 normal individual and buffered by addition of Hepes (100 mM) to a final concentration of 10 mM. The residual Factor VIII activity was then measured using a modification of the DADE Factor VIII chromogenic assay (Dade A G, Marburg, Germany). In this assay, thrombin-activated Factor VIII accelerates the conversion of Factor X into Factor Xa in the presence of Factor IXa, PL and calcium ions; Factor Xa activity is then assessed by hydrolysis of a p-nitroanilide substrate. Reagents, which were reconstituted according to the manufacturer's instruction, comprised bovine Factor X (1 mM), Factor IXa (0.3 mM) and thrombin (0.3 mM); $CaCl_2$ (30 mM), PL (60 mM), a chromogenic Factor Xa substrate ($CH_3OCO$-D-CHG-Gly-Arg-pNA.AcOH; 3.4 mM), and a thrombin inhibitor (L-amidinophenylalanine piperidine). Aliquots of 30 μl of plasma/antibody mixture were retrieved at the end of the 2 h incubation period and displayed in microtitration plates; 30 μl of the Factor X and Factor IXa/thrombin reagents were added sequentially. After 90 sec, 60 μl of the chromogenic substrate were added and the incubation extended for 10 min at 37° C. The reaction was then blocked by addition of 30 μl citric acid (1 M), and OD was measured at 405 nm. The residual Factor VIII activity was determined by comparing the $OD_{405\,nm}$ of test samples with that obtained with Factor VIII solutions of known concentrations. The residual Factor VIII activity was expressed as the percentage of activity measured in plasma aliquots handled and diluted exactly as test samples throughout the entire experiment.

Native KRIX-1 inhibited up to 90% of Factor VIII activity. By contrast, a maximal inhibition (plateau inhibition) of only 50% was achieved with deglycosylated KRIX-1 (FIG. 18).

EXAMPLE 13

Mixing Native and Deglycosylated KRIX-1 allows the Selection of Antibody Mixtures Inhibiting Factor VIII to Different Levels Mixtures containing different ratios of KRIX-1 deglycosylated with N-glycosidase-F versus native KRIX-1 were prepared. Each mixture was diluted to various antibody concentrations ranging between 0.05 and 25 microgram/ml. One volume of each dilution was mixed with one volume of a pool of normal human plasma. After a 2 hour incubation at 37° C., the residual Factor VIII was assessed using a chromogenic assay (Factor VIII Chromogenic assay, Dade Behring, Marburg, Germany). The native and deglycosylated KRIX-1 inhibited Factor VIII activity by about 90% and 50%, respectively (FIG. 19). By contrast, a mixture of 4.5 native antibody for 1 deglycosylated antibody resulted in a maximal Factor VIII inhibition or plateau inhibition of about 80% whereas a mixture containing 1.5 native KRIX-1 for 1 native antibody inhibited about 65% Factor VIII activity (FIG. 19). Mixtures inhibiting Factor VIII activity to any level comprised between 50 and 90% can be similarly obtained by varying the ratio of native and deglycosylated KRIX-1.

EXAMPLE 14

Recombinant KRIX-1 Produced in CHO Cells (CHO-recKRIX-1) has a Lower Factor VIII Inhibitory Activity than KRIX-1 (Produced by a Human Lymphoblastoid Cell Line)

RNA from KRIX-1 EBV-immortalised human B cells was isolated using TRIzol Reagent according to the manufacturer's instructions (Life Technologies). cDNA was synthesised with the SuperScript pre-amplification system for first-strand cDNA synthesis.

The sequences encoding the heavy or light chain were amplified by RT.PCR on mRNA prepared from KRIX-1 cells using the QuickPrep®Micro mRNA Purification Kit (Amersham Pharmacia Biotech, Rosendaal, The Netherlands). Specific PCR primers for the heavy chain were: forward primer 5'-cggggtaccccaccATGGACTGGACCTGGAGGATC-3' (SEQ ID NO:5) corresponding to nucleotides (nt) 1 to 21 (in capitals) of the cDNA sequence (WO 01/04269 A1), and containing a KpnI site (underlined) for cloning purposes and a Kozak sequence (bold italic); reverse primer: 5'-tatggccgac gtcgactcATTTACCCGGAGACAGGGAGAG-3' (SEQ ID NO: 6) corresponding to nt 1800-1780 (capitals) of the 3' end of the human gamma-4 constant region (accession number K01316) and containing a stop codon (bold italic) and a SalI site (underlined) for cloning purposes. Specific primers for the light chain were: forward primer 5'-ccc aagcttccaccATGGAAACCCCAGCKCAGCT-3' (SEQ ID NO: 7) corresponding to nt 1-20 (capitals) of the cDNA sequence (WO 01/04269 A1), and containing a HindIII site (underlined) for cloning purposes and a Kozak sequence (bold italic); reverse primer: 5'-aaacagcc tctagactaACACTCT-CCCCTGTTGAAG-3' (SEQ ID NO: 8) corresponding nt 653-635 of the 3' end of the human kappa constant region (accession number V00557) and containing a stop codon (bold italic) and a XbaI site (underlined) for cloning purposes. After sequence verification, the heavy and light chain sequences were cloned consecutively into the pBudCE4 plasmid (Invitrogen, Merelbeke, Belgium) designed for double gene expression in eukaryotic cells under the control of the EF1-alpha and the CMV promoter, respectively, using the above indicated restriction sites. The final vector was used for stable transfection of CKO-K1 cells using the FuGENE6 system (Roche Diagnostics, Brussels, Belgium) according to the manufacturer's instructions. The transfected cells were cultured in DMEM (Life Technologies, Paisley, UK) supplemented with 10% FCS, 4 mmol/L glutamine and 80 mg/L gentamicine (Geomycin®, Schering-Plough, Heist-op-den-Berg, Belgium) in the presence of zeocin (0.7 mg/mL selection concentration or 0.35 mg/mL maintenance concentration; Life Technologies, Invitrogen), and were verified for antibody production by ELISA (see below). The cells were adapted to growth in serum-free medium by step-wise reduction of the FCS to 0%, and after clonal dilution, the best producer in terms of functionality (ELISA on huFactor VIII), as well as expression (ELISA with anti-humanIgG4 detection antibody), was used for batch production.

For detection of anti-Factor VIII antibodies, rFactor VIII was insolubilised by incubating plates for 2 h at 4° C. directly with 50 µl of rFactor VIII (1 microgram/ml) diluted in glycin-buffered saline (GBS). The plates were washed as above and 50 µl of culture supernatant were added for a further incubation of 2h at 4° C. After washing, 50 µl peroxidase-labelled anti-human Fc gamma goat IgG (Sigma) diluted 1000-fold in Tris-casein were added. After 2 h at RT, the plates were washed again and supplemented with 100 µl OPD. The resulting OD was read at 492 nm in a Emax Microplate Reader (Molecular Devices, Menlo Park, Calif.). Negative and positive controls were culture medium and IgG purified from a high-titer inhibitor hemophilia A patient, respectively.

The recombinant antibody was purified from the cell culture supernatant by adsorption on immobilized protein A (High-TRAP Protein A, Pharmacia, Uppsala, Sweden). Culture supernatant was passed through a high-TRAP® protein A (Pharmacia, Uppsala, Sweden) at a flow rate of 1 ml/min. Bound IgG was eluted with citric acid 100 mM, pH3. After pH neutralisation with Tris pH9, IgG was dialysed against Phosphate buffered saline (PBS). The concentration of proteins was determined with the Bio-Rad assay (Biorad).

The recombinant antibody produced in CHO cells was called CHO-recKRIX-1. Interestingly, the maximal inhibition observed in large excess of this antibody reaches only 75-85% Factor VIII activity, which is lower than the 85-95% maximal (plateau) inhibition observed when Factor VIII is incubated with KRIX-1 (produced by the human lymphoblastoid cell line (FIG. 20).

EXAMPLE 15

Prevention of Vena Cava Thrombosis Using CHO-recKRIX-1 in Mice

Thrombus was produced in the inferior vena cava of adult male wild-type mice (weight 18g-31g, age 8-10 weeks) using a previously described model (Singh et al. (2002) cited supra). Mice were anaesthetised with isoflurane, the inferior vena cava was exposed below the renal veins via a median laparotomy and a neurosurgical vascular clip (Braun Medical) was applied for 15 seconds on two occasions, 30 seconds apart to a segment of the vena cava. A 5/0 prolene thread was then placed alongside the vena cava and a stenosis produced by tying a 4/0 silk suture around the vena cava and the prolene thread. The thread was removed to allow blood flow to resume. The abdomen was closed and the animal allowed to recover. After 4 hours, the mice were reanaesthetised and a 1 cm portion of the inferior vena cava (between the point of ligature and iliac bifurcation) was excised and examined for the presence of thrombus. The excised segments were then washed in 10% PBS and soaked overnight in 1% paraformaldehyde. Vessel segments were embedded in paraffin wax and 7×10 µm transverse sections were cut at 0.5 mm intervals from the ligature down.

Sections were stained by haematoxylin and eosin, Martius Scarlet Blue (MSB) and a rabbit anti-platelet antibody (Accurate Chemical & Scientific Corporation, Westbury, N.Y. 11590). MSB stains fresh fibrin red or mature fibrin blue/gray, red cells yellow and collagen bright blue. Thrombus size was measured by scoring the 7 sections for the presence of thrombus, giving a score of 1 for the presence and 0 for the absence of thrombus in each. Scores were then added up for each animal. The investigators performing the operations and the microscopic analyses were blinded towards treatment groups.

Thrombosis was induced in three groups of wild-type mice 16 hours after subcutaneous injection of 150 microgram of antibody or saline. The statistical significance of differences between groups was evaluated on the presence or absence of thrombus using Fisher's exact test (2-sided). The effects on thrombus size were tested by comparing thrombus scores using the Mann-Whitney U test.

Ten out of 14 mice injected with saline developed a thrombus, visible macroscopically, compared with 0 out of the 7 animals in each of the groups pretreated with either KRIX-1 or CHO-recKRIX-1 (P<0.01).

Histological analysis identified thrombi in 11 out of 14 control animals and 1, 1, and 2 thrombi, respectively, in animals treated with KRIX-1 or CHO-recKRIX-1 (FIG. 21). Accordingly, although CHO-recKRIX-1 inhibits Factor VIII activity significantly less than KRIX-1, CHO-recKRIX-1 inhibits very efficiently thrombosis and therefore offers a better safety/efficacy profile than the native KRIX-1 antibody.

EXAMPLE 16

Antithrombotic Activity of CHO-recKRIX-1 in Mice with Type II Heparin Binding Site (HBS) Antithrombin Deficiency ($AT^{m/m}$)

The antithrombotic efficacy of CHO-recKRIX-1 was evaluated using the thrombotic priapism model in mice with type II heparin binding site (HBS) antithrombin deficiency (Dewerchin et al. submitted).

The mice were previously generated by targeted knock-in of an R48C mutation (corresponding to the "Toyama" R47C mutation in man, abolishing heparin/heparan sulphate binding and cofactor activity (Koide et al. (1983) *Thromb Res.* 31, 319-328; Koide et al. (1984) *Proc Natl Acad Sci USA.* 81, 289-293) in the HBS of antithrombin (AT) ($AT^{m/m}$ mice), resulting in life-threatening, spontaneous thrombosis at different sites, most prominently in the heart, liver, and in ocular, placental and penile vessels (Dewerchin et al. (2003) *Circ Res* 93,1120-1126). The observation of priapism occurrence upon mating of males $AT^{m/m}$ provided the basis to the development of a physiological model of venous thrombosis, providing a defined endpoint and an easy grading of the thrombotic outcome.

Age-matched groups of sexually mature males (2 to 4 months) were subcutaneously injected twice (three days before mating and on the day of mating) with 100 µl of saline or with 100 µl of a 1 mg/ml solution of KRIX-1, CHO-recKRIX-1Q or CHO-recKRIX-1. After the second injection, each male was mated to two wild type Swiss females, which were replaced by two new females on day 3 after mating. The formation of a vaginal mucus plug indicating recent mating was recorded daily for all females, and only the results obtained with males with confirmed sexual activity were incorporated in the analysis. Males were examined daily for development of priapism and were sacrificed when priapism was observed, or at day 8 after initial mating when the experiment was ended. At sacrifice, blood samples were collected for determination of residual Factor VIII activity and human IgG levels as described above. The penises were dissected and the presence of thrombus IN the dorsal penile vein and corpora cavernosae determined by visual inspection.

After sacrifice, the dissected penises were paraformaldehyde fixed, parafin-embedded and processed for histological analysis. Seven-µm transverse sections were stained with haematoxylin/eosin for microscopic analysis.

Scoring: Thrombotic outcome was scored using four categories: 0, no thrombosis; 1, thrombosis of the penile vein by microscopy; 2, macroscopically visible thrombosis of the penile vein; 3, irreversible thrombotic priapism. When no macroscopically visible thrombus was observed and no histology of the penile vein could be obtained for technical reasons, the animals were also scored 1. The investigators performing the injections and monitoring the mice were blinded towards the treatment groups. The statistical significance of differences between thrombus scores was tested using the Kruskal-Wallis or Mann-Whitney U test.

The presence of a vaginal mucus plug in at least 2 females within the follow-up period for each these males treated with antibody or saline, confirmed actual sexual activity of the males.

KRIX-1, CHO-rec-KRIX-1 were able to prevent priapism in all mice tested (p<0.05 versus saline) (FIG. 22). In the group injected with 2×100 µg KRIX-1 antibody, none of the five males developed priapism; four of them were also free of thrombosis upon visual inspection and by microscopic analysis at the end of the experiment; the remaining male did not show macroscopic thrombosis. For technical reasons, no histological analysis could be performed and the animal was therefore scored 1 (FIG. 22), the maximal score which could have been attributed if the analysis had been performed.

A similar outcome was observed for the recombinant CHO-rec-KRIX-1 antibody: none of seven treated males developed priapism; five males were also free of macroscopic or microscopic thrombosis (FIG. 22); one male showed only microscopically detectable thrombosis (score 1) (FIG. 22) and one male was free of macroscopically visible thrombosis but could not be analyzed by microscopy and was therefore also scored 1 (FIG. 22).

EXAMPLE 17

Antithrombotic Activity of CHO-recKRIX-1Q in Mice with Type II Heparin Binding Site (HBS) Antithrombin Deficiency ($AT^{m/m}$)

As outlined in example 16, the antithrombotic efficacy of CHO-recKRIX-1Q was evaluated using the thrombotic priapism model in mice with type II heparin binding site (HBS) antithrombin deficiency (Dewerchin et al. (2003) *Circ Res* 93,1120-1126).

In the present example, age-matched groups of sexually mature males were subcutaneously injected twice (three days before mating and on the day of mating) with 100 µl of saline or with 100 µl of a 1 mg/ml solution of CHO-recKRIX-1Q, a control human IgG4 monoclonal antibody, which does not recognise Factor VIII, or the vehicle (PBS).

CHO-recKRIX-1 was able to reduce thrombosis development (p<0.05 versus PBS and control IgG4) (FIG. 27). In the group injected with 2×100 microgram CHO-recKRIX-1Q antibody, none of the males died or developed priapism. All animals treated with CHO-recKRIX-1Q were also free of thrombosis upon visual inspection For technical reasons, no histological analysis could be performed and the animal were therefore scored 1 (FIG. 27), the maximal score which could have been attributed if the analysis had been performed. By contrast, in the groups treated with PBS or a control human IgG4 monoclonal antibody, several animals died or developed priapism (p<0.01, CHO-recKRIX-1Q versus PBS and control IgG4).

EXAMPLE 18

Production and Characterisation of Variant of CHO-recKRIX-1 Devoid of N-glycosylation Site in the Antigen Binding Site CHOrecKRIX-1Q was produced by site directed mutagenesis on the pCR4-Blunt-TOPO-KRIX-1H plasmid resulting in a single amino acid change in the heavy chain altering the Asn47 into Gln47 in order to disrupt the N-linked glycosylation site at Asn47-Thr49. Other plasmids comprising the coding sequence of the KRIX-1 antibody can similarly be used in the context of the present invention. Amino acid sequences comprising the CDRs of the heavy and light chains of KRIX-1 are provided in SEQ ID NOs33 to 35 and 36 to 38 for the heavy and light chains, respectively. Nucleotide sequences encoding sequences of the CDRs of the heavy and light chains of KRIX-1 can be identified within the nucleotide sequence encoding the heavy and light chain variable region of KRIX-1 provided in SEQ ID NO:1 and SEQ ID NO: 3, respectively.

The mutagenesis at Asn47 was obtained using the Site Directed Mutagenesis Kit (Stratagene, La Jolla, Calif.) in combination with the following specific PCR primers:
Forward Primer:
5'-CCTGCAAGACCTCTGGATACcAaTTCAC-CGGCTACTCTGCTTCTGG-3' (SEQ ID NO: 9) corresponding to nt 119 to 164 of the KRIX-1 Heavy chain sequence (capital) containing two altered nucleotides (a to c and c to a; bold italic);
Reverse Primer:
5'-CCAGAAGCAGAGTAGCCGGTGAAtTgG-TATCCAGAGGTCTTGCAG-G-3' (SEQ ID NO: 10) corresponding to nt 119 to 164 of the KRIX-1 Heavy chain sequence (capital) containing two altered nucleotides (g to t and t to g; bold italic)

CHO-recKRIX-1A was produced by site directed mutagenesis resulting in a single amino acid change altering Thr49 into Ala49 in order to disrupt the N-linked glycosylation site at Asn47-Thr49

This was obtained using the Site Directed Mutagenesis Kit (Stratagene, La Jolla, Calif.) in combination with the following specific PCR primers:
Forward Primer:
5'-CCTCTGGATACAACTTCgCtGGC-TACTCTGCTTCTGG-3' (SEQ ID NO: 11) corresponding to nt 128 to 164 of the KRIX-1 Heavy chain sequence (capital) containing two altered nucleotides (a to g and c to t; bold italic);
Reverse Primer:
5'-CCAGAAGCAGAGTAGCCaGcGAAGTTG-TATCCAGAGG-3' (SEQ ID NO: 12) corresponding to nt 128 to 164 of the KRIX-1 Heavy chain sequence (capital) containing two altered nucleotides (g to a and t to c; bold italic);

CHO-recKRIX-1E was produced by site directed mutagenesis resulting in a single amino acid change altering Asn47 into Glu47 in order to disrupt the N-linked glycosylation site at Asn47-Thr49
Forward Primer:
5'-CCTGCAAGACCTCTGGATACgAgTTCAC-CGGCTACTCTGCTTCTGG-3' (SEQ ID NO: 13) corresponding to nt 119 to 164 of the KRIX-1 Heavy chain sequence (capital) containing two altered nucleotides (a to g and c to g; bold italic);
Reverse Primer:
5'-CCAGAAGCAGAGTAGCCGGTGAAcTcG-TATCCAGAGGTCTTGCAG-G-3' (SEQ ID NO: 14) corresponding to nt 119 to 164 of the KRIX-1 Heavy chain sequence (capital) containing two altered nucleotides (g to c and t to c; bold italic).

CHO-recKRIX-1D was produced by site directed mutagenesis resulting in a single amino acid change altering Asn47 into Asp47 in order to disrupt the N-linked glycosylation site at Asn47-Thr49.
Forward Primer:
5'-CCTGCAAGACCTCTGGATACgACTTCAC-CGGCTACTCTGCTTCTGG-3' (SEQ ID NO: 15) corresponding to nt 119 to 164 of the KRIX-1 Heavy chain sequence (capital) containing one altered nucleotide (a to g; bold italic);
Reverse Primer:
5'-CCAGAAGCAGAGTAGCCGGTGAAGTcG-TATCCAGAGGTCTTGCAG-G-3' (SEQ ID NO: 16) corresponding to nt 119 to 164 of the KRIX-1 Heavy chain sequence (capital) containing one altered nucleotide (t to c; bold italic)

After sequence verification, the mutated heavy and wild-type (native) KRIX-1 light chains were cloned into the pEE6.4 and pEE14.4 vector (Lonza Biologics, Portsmouth, N.H.) respectively. The two vectors were combined to a double gene vector—containing both heavy and light chain—using the NodI and SalI restriction sites present in both vectors. Heavy and light chain expression in eukaryotic cells is under the control of the hCMV-MIE promoter (present in pEE14.4 and pEE6.4). The double gene vector was linearised with SalI before transfection.

The linearised vector was used for stable transfection of CKO-K1 cells using the FuGENE6 transfection reagent (Roche, Brussels, Belgium) according to the manufacturer's instructions. The transfected cells were cultured in glutamine-free DMEM (JRH Biosciences, Lenexa, Kans.) supplemented with FBS 10%, GS Supplement (JRH Biosciences, Lenexa, Kans.) and 25 µM L-Methionine Sulfoximine (MSX) (Sigma-Aldrich, Bornem, Belgium) for selection.

The best producers were adapted to growth in serum-free medium (EX-CELL 302 serum-free medium w/o L-Glutamine, JRH Biosciences, Lenexa, Kans.)—supplemented with 25 µM MSX and GS Supplement—by step-wise reduction of the FBS to 0%. The best expressing (ELISA with anti-humanIgG4 detection antibody) functional cell line was used for batch production of the mutated rec-mAb-KRIX-1, either using the adherent or the suspension cell line.

The recombinant antibody was purified from the cell culture supernatant by affinity chromatography using a HiTrap rProtein A FF column (Amersham Biosciences, Uppsala, Sweden). After concentration the rec-mAb-KRIX-1Q (A, E and D resp.) were assayed for functionality (Chromogenic assay to evaluate the ability of the mutated rec-mAb KRIX-1 to inhibit fVIII activity) Inhibitory capacity towards fVIII was compared to that of the wild type rec-mAb KRIX-1 (FIGS. 23 and 24). Factor VIII inhibition by these mutants ranged from 30 to 40%.

Measurement of Surface Plasmon Resonance (SPR).
The rate of Factor VIII association and dissociation to CHO-rec-KRIX-1Q, CHO-rec-KRIX-1A and native CHO-rec-KRIX-1 was analysed using a Pharmacia Biosensor BIAcore™ instrument (Pharmacia Biosensor AB). Purified antibody (20 microgram/ml in 10 mM sodium acetate buffer pH 5.0) was immobilised on the activated surface of a CM5 sensor chip, according to the manufacturer's instructions. All binding experiments were carried out in HBS at a constant flow rate of 10 µl/min. Factor VIII in Hepes Buffered Saline (HBS) was infused at various concentrations over the antibody coated on the sensor chip surface. At the end of each cycle, the surface was regenerated by flushing HCl, pH 2, for 36 sec. Control experiments ensured that Factor VIII bound only to insolubilised antibody. Thus, rFactor VIII did not bind to the sensor chip in the absence of antibody, and preincubation of rFactor VIII with soluble antibody prior to addition to the chip completely prevented Factor VIII binding.

Association and dissociation rate constants were determined by non-linear fitting of individual sensorgram data (O'Shanessy et al. (1993), *Analyt Biochem* 212: 457) using the BIA evaluation 2.1 software (Pharmacia Biotech, Uppsala, Sweden). Values of $k_{ass}$ and $k_{diss}$ were determined by averaging the values obtained for individual curves established with various analyte concentrations. Values of $k_{diss}$ were determined from the individual curves obtained with only the highest analyte concentration, in order to reduce bias due to rebinding of the analyte to free immobilized ligand. All data were analysed after correction of the baseline by subtracting the response observed before injection of the analyte (rfVIII) from the response values obtained during the association and dissociation phases.

The dissociation constant ($K_D$) of Factor VIII from CHO-rec-KRIX-1Q, CHO-rec-KRIX-1A and native CHO-rec-KRIX-1 was very similar (Table 2). Accordingly, the glycosylation site in the antigen binding site of mAb KRIX-1 influences the antibody inhibitory activity but does not contribute significantly to binding to Factor VIII.

TABLE 2 surface plasmon resonance analysis of Factor VIII binding to mAb KRIX-1 and derivative thereof.

| Modified mAb KRIX-1 (LCL): | $K_D$ (nM) |
|---|---|
| CHO-recKRIX-1 | 0.14 ± 0.03 |
| CHO-recKRIX-1Q | 0.17 ± 0.02 |
| CHO-recKRIX-1A | 0.13 ± 0.01 |

EXAMPLE 19

Prevention of Arterial and Venous Thrombosis in Baboons Methods

Protocol

Male baboons (*Papio ursinus*) were used. The animals weighed between 8 and 17 kg and were disease-free for at least 6 months prior to the experiments. All procedures were approved by the Ethics Committee for Animal Experimentation of the University of the Free State in accordance with the National Code for Animal Use in Research, Education, Diagnosis and Testing of Drugs and Related Substances in South Africa.

Permanent polytetrafluoroethylene (Teflon) and silicone rubber (Silastic) arteriovenous (AV) shunts were implanted in the baboon femoral vessels. Blood flow through the shunts varied between 100 and 120 mL/min. Handling of the baboons was achieved through anesthesia with ketamine hydrochloride (Anaket-V, Centaur Laboratory).

In each experiment, a thrombogenic device prefilled with saline to avoid a blood-air interface was incorporated as an extension segment into the permanent arteriovenous shunt by means of Teflon connectors (Kotze et al. (1983) *Thromb Haemost.* 70, 672-675). Platelet-dependent arterial thrombus was induced by using Dacron inserted into the wall of Silastic tubing (3-mm inside diameter) according to Hanson et al. (1985) *Arteriosclerosis* 5, 595-603 (FIG. 25).

The Dacron vascular graft material (1.26 $cm^2$) served as a generator of platelet-dependent arterial-type thrombosis. An expansion chamber (3.77 $cm^2$) was used to generate coagulation-dependent venous thrombosis. Blood flowed through the thrombogenic devices at a rate of approximately 120 ml/min. The initial shear stress was 318 $sec^{-1}$ for the Dacron section and 10 $sec^{-1}$ for the expansion chamber.

In the control studies, the devices were kept in place for 60 minutes or until they occluded, after which they were removed and blood flow through the permanent AV-shunt re-established. The baboons were then treated with a single intravenous bolus of 1.25 or 5 mg/kg CHO-rec-KRIX-1Q. The thrombogenic devices were placed for 60 minutes, 1 h after antibody injection, after which the devices were removed and blood flow through the permanent AV-shunt reestablished. Additional 60-minute studies were carried at 24 h and 48 h after the antibody bolus injection. The extracorporeal shunts were then removed after the last thrombosis experiment. Blood samples were taken according to the sampling schedule either directly from the shunt or by venopuncture. Factor VIII activity, mAb KRIX-1 concentrations monitored, PT, APTT, fibrinogen, were measured on all samples.

Graft Imaging.

Autologous platelets were labeled with 111In-tropolone and reinjected into the animal 1 h before the start of the control experiment. This allowed image acquisition on day 0, 1 and 2. To provide image acquisition on day 6 or 14 the labeling procedure was repeated. Image acquisition of the grafts was done with a gamma scintillation camera fitted with a high-resolution collimator. The images were stored on and analysed with a computer imaging and analysis system interfaced with the scintillation camera. Dynamic image acquisition, 3-minute image of a 5ml autologous blood sample were also acquired each time the grafts were imaged to determine blood radioactivity (blood standard). Regions of interest of the graft and expansion segments were selected to determine the deposited and circulation radio-activity in the dynamic image. The total number of platelets deposited on the vascular graft material and in the expansion chamber were calculated.

In 6 animals treated with CHO-rec-KRIX-1E, platelet deposition was lower than in the control animal treated with saline in both the venous and arterial thrombosis chambers (FIG. 26).

EXAMPLE 20

Treatment of Sepsis Related Conditions with Inhibitory Antibodies Against Factor VIII with Modified Glycosylation Injection of endotoxin elicits the production of pro-inflammatory cytokines among which IL-6 and TNF-α are important for their interactions with the coagulation system. Thus, IL-6 increases the production of tissue Factor and, consequently, the generation of thrombin. It also increases the production of fibrinogen by an independent mechanism. TNF-α increases the levels of plasminogen activation inhibitor type I (PAI-1) and thereby reduces fibrinolysis.

Groups of six mice (C57B1/6) are constituted for each treatment.

Wild type and F VIII knock-out mice are intravenously injected with 30 and 100 microgram of the following antibodies:
no antibody
control antibody (IgG4)
mutated Krix 1 at Asn47 (CHO-recKRIX-1Q)
(KRIX-1)/(CHO-recKRIX-1Q) in a ¼ or other ratio Other mixtures comprising KRIX-1 or KRIX-1 derivatives are envisaged for testing such as mixtures comprising fragments of native or deglycosylated KRIX-1 (more particularly, Fab or scFv fragments). Other mixtures comprising KRIX-1 or KRIX-1 derivatives and a second antibody (as disclosed in example 13) or derivatives thereof are also considered. A particular mixture comprises KRIX-1 and RHD5 or fragments of KRIX-1 and/or RHD5.

60 minutes after the administration of the antibody, the different mouse population are injected intraperitoneally with either microgram4 microgram or 40 microgram or 400 microgram lipopolysaccharide (from *E. coli* serotype 0:111: B4) per 20 g of body weight. 90 minutes later, for each experimental setting blood is taken of part of the population by cardiac puncture in citrate buffer for evaluation of cytokine and coagulation factor levels. Plasma is obtained by centrifugation for 5 minutes at 5,000 rpm.

The survival of the remaining mice is followed for one week.

The extent to which the fibrinolytic pathway is by a lipopolysaccharide injection of 40 microgram per 20 g body weight is evaluated by measuring concentrations of the two main pathway inactivators, namely PAI-1 (Plasminogen activator inhibitor-I) and $\alpha_2$-antiplasmin, using a sandwich-type ELISA with two specific monoclonal antibodies directed towards different sites of the molecule under evaluation.

The evolution of fibrinogen plasma concentrations is used as a reading of its conversion into fibrin.

Determination of zymogen and activated protein C can be measured for example in accordance to Richards et al. (1990) *Clin. Chem.* 36, 1892-1896.

The present experiment allows the identification of a suitable antibody or mixture of antibodies in order to prevent the endotoxin related sepsis. Analogous experiments can be devised for other components, or conditions which lead to the upregulation of the inflammatory cytokines IL-6 and/or TNF-alpha.

EXMAPLE 21

Production of Antigen Binding Fragment (Fab) of Native and Deglycosylated KRIX-1.

LCL-and CHO-KRIX-1 (0.5 mg/ml in PBS) was mixed with N-glycosidase-F (Roche Diagnostics Gmbh, Mannheim, Germany) at final concentration of 2 U/ml. The mixture was incubated at 37° C. during 72 hours under gentle stirring.

Fab fragments were produced by incubating LCL-and CHO-KRIX-1 (0.5 mg/ml) in phosphate buffer ($KH_2PO_4$ 0.039M, $Na_2HPO_4$ 0.068M, pH 7.0 with Cysteine (0.05 M), EDTA (1 mM) and papain (10 microgram/ml). After 3 h incubation at 37° C., the reaction was stopped by adding 0.075M Iodoacetamine. After 30 min at 20° C., the mixture was dialysed against phosphate buffered saline (PBS). Undigested antibodies were removed by adsorption on HiTrap Protein A (Pharmacia).

The inhibitory activity of native and deglycosylated KRIX-1 Fab was assessed in a Bethesda assay (Kasper et al. (1975), cited supra) and is shown in FIG. 28.

EXAMPLE 22

Production and Characterization of KRIX-1 and KRIX-1Q scFv Fragment

Cloning of scFv-KRIX-1VLVH in *Pichia* Expression Vector

An scFv fragment of KRIX-1 was constructed by adding a linker sequence between the 3' end of the KRIX-1 light chain variable part (VL) and the 5'end of the heavy chain variable part (VH). This was obtained by PCR amplification of KRIX-1 light chain and heavy chains using the following primers:

For the light chain: forward primer 5'-gtatct ctcgagaaaaga*GAAATTGTGT-TGACGCAGTCTCCAG-GC-3*' [SEQ ID NO:17] corresponding to the 5' end of the KRIX-1 VL sequence (capital), and containing a XhoI restriction site (underlined) and a KEX1 sequence (bold italic); reverse primer 5'-cgccagagccacctccgcctgaaccgcctccacc-TCGTTTGATCTCCACCTTGGTC [SEQ ID NO:18] corresponding to the 3' end of the KRIX-1 Jk sequence (capital), and containing a part of the linker sequence (italic)

For the heavy chain: forward primer 5'-caggcggaggtg-gctctggcggtg-gcggatcgCAGGTMCAGCTGGTG-CAGTCTGGG-3' (SEQ ID NO:19) corresponding to the 5' end of the KRIX-1 VH sequence (capital), and containing a part of the linker sequence (italic); reverse primer 5'-gatc tctagaTGAGGAGACGGTGACCAGGGTTCC [SEQ ID NO:20] corresponding to the 3' end of the KRIX-1 JH sequence (capitals), and containing a XbaI restriction site (underlined)

The PCR products were annealed and a second PCR was performed using the forward primer for the light chain (SEQ ID NO:17) and the reverse primer for the heavy chain (SEQ ID NO: 20). The resulting scFv-KRIX-1VLVH was cloned into the pPICZalphaC expression vector (Invitrogen, Merelbeke, Belgium)

Cloning of scFv-KRIX-1VLVH with His(6)tag in *Pichia* Expression Vector

A SalI restriction site was added to the scFv-KRIX-1VLVH sequence in order to clone it in frame with the His(6) sequence included in the pPICZalphaC expression vector (Invitrogen; Merelbeke; Belgium). This was obtained by PCR using the forward primer 5'-gtatctctcgagaaaagaG-AAATTGTGTTGACGCAGTCTCCAGGC-3' (SEQ ID NO:21) corresponding to the 5' end of the KRIX-1 VL sequence (capital), and containing a XhoI restriction site (underlined) and a KEX1 sequence (bold italic); and the reverse primer 5'-catggtcgacTGAGGAGACG-GTGACCAGGGTTCCCCGGCC-3' (SEQ ID NO:22) corresponding to the 3' end of the KRIX-1 heavy chain JH sequence (capital), and containing a SalI restriction site (underlined).

The final pPICZalphaC-scFv-KRIX-1VLVH(His) vector was used to transform X33 cells for scFv production. The supernatant was tested to demonstrate the presence of a functional scFv fragment.

The scFv fragment was purified using the HisTrap Kit (Amersham Pharmacia Biotech, Uppsala, Sweden). After concentration the scFvKRIX-1VLVH(His) was tested in a Factor VIII chromogenic assay to evaluate the ability of the scFvKRIX-1VLVH(His) to inhibit Factor VIII activity. The Factor VIII inhibitory capacity was evaluated in a Besthesda assay according to the method in example 1 and is shown in FIG. 29.

Cloning of scFv-KRIX-1VLVHQ with His(6)tag in *Pichia* Expression Vector

The scFv-KRIX-1VLVHQ(His) was produced by site directed mutagenesis on the pPICZalphaC-scFv-KRIX-1VLVH(His) resulting in a single amino acid change in the heavy chain replacing Asn47 by a glutamine in order to disrupt the N-linked glycosylation site at Asn47-Thr49

This was obtained using the Site Directed Mutagenesis Kit (Stratagene, La Jolla, Calif.) in combination with the following specific PCR primers:

Forward primer: 5'-CCTGCAAGACCTCTGGATAC-cAaTTCACCGGCTAC-TCTGCTTCTGG-3' (SEQ ID NO: 23) corresponding to nt 119 to 164 of the KRIX-1 Heavy chain sequence (capital) containing two altered nucleotides (a to c and c to a; bold italic).

Reverse primer: 5'-CCAGAAGCAGAGTAGCCGGT-GAAtTgGTATC-CAGAGGTCTTGCAGG-3' (SEQ ID NO: 24) corresponding to nt 119 to 164 of the KRIX-1 Heavy chain sequence (capital) containing two altered nucleotides (g to t and t to g; bold italic).

The full length nucleotide and protein sequence of scFv-KRIX-1VLVHQ with His(6)tag is described in SEQ ID NO: 25 and 26.

Cloning of scFv-KRIX-1VLVH and scFvKRIX-1VLVHQ (His) with His(6)tag in a CHO Expression Vector The KRIX-1 light chain leader sequence was introduced into pPICZalphaC-scFv-KRIX-1VLVH(His) and pPICZalphaC-scFv-KRIX-1VLVHQ(His) by cloning of a HindIII/PstI restriction fragment of pCR4-KRIX-1L containing the leader sequence into HindIII/PstI digested pPICZalphaC-scFv-KRIX-1VLVH and pPICZalphaC-KRIX-1VLVHQ respectively. The resulting scFv sequence was adapted for cloning and expression purposes by PCR using the following specific primers:

Forward primer: 5'-cccaagcttgccgccaccAT-GGAAACCCCAGCKCAGCTTC-3' (SEQ ID NO:27) corresponding to the 5' end of the KRIX-1 Light chain sequence (capital), and containing a HindIII site (underlined) and a Kozak sequence (bold italic).

Reverse primer: 5'-ccggaattctcaatgatg-atgatgatgatgTGAGGAGACGGTGA-CCAGGGTTCC-3' (SEQ ID NO:28) corresponding to the 3' end of the KRIX-1 heavy chain JH sequence (capital), and containing a EcoRI site (underlined), a stop signal sequence (bold italic) and a His(6)tag sequence (italic)

The resulting PCR products were cloned into the pGEM-T-Easy vector (Promega; Leiden, Netherlands). After sequence verification the scFvKRIX-1VLVH(His) and scFv-KRIX-1VLVHQ(His) were cloned into the pEE14.4 vector (Lonza Biologics, Portsmouth, N.H.). The resulting vector was linearised with SalI before transfection.

The linearised vector was used for stable transfection of CKO-K1 cells using the FuGENE6 transfection reagent (Roche, Brussels, Belgium) according to the manufacturer's instructions. The transfected cells were cultured in glutamine-free DMEM (JRH Biosciences, Lenexa, Kans.) supplemented with FBS 10%, GS Supplement (JRH Biosciences, Lenexa, Kans.) and 50 µM L-Methionine Sulfoximine (MSX) (Sigma-Aldrich, Bornem, Belgium) for selection.

The best producers were adapted to growth in serum-free medium (EX-CELL 302 serum-free medium w/o L-Glutamine, JRH Biosciences, Lenexa, Kans.)—supplemented with GS Supplement and MSX in the respective concentration—by step-wise reduction of the FBS to 0%.

The supernatants were assayed for production of scFv-KRIX-1VLVH(His) and scFv-KRIX-1VLVHQ(His) in a Factor VIII chromogenic assay as described in example. The Factor VIII inhibitory capacity of the culture supernatant is shown in FIG. 30.

We claim:

1. An isolated monoclonal anti-Factor VIII antibody wherein said antibody is binding to an epitope of the isolated C1 domain of Factor VIII, said Cl domain comprising the residue Arg at amino acid position 2150 of Factor VIII, and wherein said binding is abrogated when said Arg residue is mutated into a His residue; and inhibiting Factor VIII activity by at most 98%, even when said antibody is, on a molar basis, in large excess of Factor VIII;

or an antigen-binding fragment of said antibody.

2. A pharmaceutical composition comprising an isolated monoclonal anti-Factor VIII antibody or fragment thereof of claim 1 in admixture with a pharmaceutically acceptable carrier.

* * * * *

```
                        SEQUENCE LISTING

<160> NUMBER OF SEQ ID NOS: 48

<210> SEQ ID NO 1
<211> LENGTH: 496
<212> TYPE: DNA
<213> ORGANISM: Homo sapiens
<220> FEATURE:
<221> NAME/KEY: CDS
<222> LOCATION: (1)..(495)
<223> OTHER INFORMATION: KRIX-1 heavy chain variable region
<220> FEATURE:
<221> NAME/KEY: misc_feature
<222> LOCATION: (1)..(57)
<223> OTHER INFORMATION: Nucleotide sequence encoding leader sequence
<220> FEATURE:
<221> NAME/KEY: misc_feature
<222> LOCATION: (133)..(192)
<223> OTHER INFORMATION: nucleotide sequence encoding CDR1
<220> FEATURE:
<221> NAME/KEY: misc_feature
<222> LOCATION: (235)..(285)
<223> OTHER INFORMATION: nucleotide sequence encoding CDR2
<220> FEATURE:
<221> NAME/KEY: misc_feature
<222> LOCATION: (382)..(435)
<223> OTHER INFORMATION: nucleotide sequence encoding CDR2

<400> SEQUENCE: 1 atg gac tgg acc tgg agg atc ctc ttc ttg gtg gca gca gcc aca gga        48
```

```
Met Asp Trp Thr Trp Arg Ile Leu Phe Leu Val Ala Ala Ala Thr Gly
1               5                   10                  15 gcc cac tcc cag gtg caa ctg gtg caa tct ggg gct gag gtg aag aag      96
Ala His Ser Gln Val Gln Leu Val Gln Ser Gly Ala Glu Val Lys Lys
                20                  25                  30 cct ggg gcc tca gtg aag gtc tcc tgc aag acc tct gga tac aac ttc     144
Pro Gly Ala Ser Val Lys Val Ser Cys Lys Thr Ser Gly Tyr Asn Phe
            35                  40                  45 acc ggc tac tct gct tct gga cat atc ttc acc gcc tac tct gtg cac     192
Thr Gly Tyr Ser Ala Ser Gly His Ile Phe Thr Ala Tyr Ser Val His
        50                  55                  60 tgg gtg cga cag gcc cct gga caa ggg ctt gag tgg atg gga agg atc     240
Trp Val Arg Gln Ala Pro Gly Gln Gly Leu Glu Trp Met Gly Arg Ile
65                  70                  75                  80 aac cct aac agt ggt gcc aca gac tat gca cat aaa ttt cag ggc agg     288
Asn Pro Asn Ser Gly Ala Thr Asp Tyr Ala His Lys Phe Gln Gly Arg
                85                  90                  95 gtc acc atg tcc agg gac acg tcc atc agc aca gcc tac atg gaa ctg     336
Val Thr Met Ser Arg Asp Thr Ser Ile Ser Thr Ala Tyr Met Glu Leu
            100                 105                 110 agc agg ctg aca tct gac gac acg gcc atg tat tac tgt gcg aga gcc     384
Ser Arg Leu Thr Ser Asp Asp Thr Ala Met Tyr Tyr Cys Ala Arg Ala
        115                 120                 125 gac aac tat ttc gat att gtg act ggc tat act tct cat tac ttt gac     432
Asp Asn Tyr Phe Asp Ile Val Thr Gly Tyr Thr Ser His Tyr Phe Asp
130                 135                 140 tac tgg ggc cgg gga acc ctg gtc acc gtc tcc tca gcc tcc acc aag     480
Tyr Trp Gly Arg Gly Thr Leu Val Thr Val Ser Ser Ala Ser Thr Lys
145                 150                 155                 160 ggc cca tcg gtc ttc c                                                496
Gly Pro Ser Val Phe
                165

<210> SEQ ID NO 2
<211> LENGTH: 165
<212> TYPE: PRT
<213> ORGANISM: Homo sapiens

<400> SEQUENCE: 2

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Thr Ser Gly Tyr Asn Phe
            35                  40                  45

Thr Gly Tyr Ser Ala Ser Gly His Ile Phe Thr Ala Tyr Ser Val His
        50                  55                  60

Trp Val Arg Gln Ala Pro Gly Gln Gly Leu Glu Trp Met Gly Arg Ile
65                  70                  75                  80

Asn Pro Asn Ser Gly Ala Thr Asp Tyr Ala His Lys Phe Gln Gly Arg
                85                  90                  95

Val Thr Met Ser Arg Asp Thr Ser Ile Ser Thr Ala Tyr Met Glu Leu
            100                 105                 110

Ser Arg Leu Thr Ser Asp Asp Thr Ala Met Tyr Tyr Cys Ala Arg Ala
        115                 120                 125

Asp Asn Tyr Phe Asp Ile Val Thr Gly Tyr Thr Ser His Tyr Phe Asp
130                 135                 140

Tyr Trp Gly Arg Gly Thr Leu Val Thr Val Ser Ser Ala Ser Thr Lys
145                 150                 155                 160
```

```
Gly Pro Ser Val Phe
            165

<210> SEQ ID NO 3
<211> LENGTH: 429
<212> TYPE: DNA
<213> ORGANISM: Homo sapiens
<220> FEATURE:
<221> NAME/KEY: CDS
<222> LOCATION: (1)..(429)
<223> OTHER INFORMATION: KRIX-1 light chain variable region
<220> FEATURE:
<221> NAME/KEY: misc_feature
<222> LOCATION: (1)..(60)
<223> OTHER INFORMATION: nucleotide sequence encoding leader peptide
<220> FEATURE:
<221> NAME/KEY: misc_feature
<222> LOCATION: (130)..(164)
<223> OTHER INFORMATION: nucleotide sequence encoding CDR1
<220> FEATURE:
<221> NAME/KEY: misc_feature
<222> LOCATION: (211)..(231)
<223> OTHER INFORMATION: nucleotide sequence encoding CDR2
<220> FEATURE:
<221> NAME/KEY: misc_feature
<222> LOCATION: (328)..(357)
<223> OTHER INFORMATION: nucleotide sequence encoding CDR3

<400> SEQUENCE: 3 atg gaa acc cca gct cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
            20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
        35                  40                  45 gtt gcc agc gcc tac tta gcc tgg tac cag caa aaa cct ggc cag gct     192
Val Ala Ser Ala Tyr Leu Ala Trp Tyr Gln Gln Lys Pro Gly Gln Ala
    50                  55                  60 ccc agg ctc ctc atc tat ggt gca tcc agt agg gcc act gac atc cca     240
Pro Arg Leu Leu Ile Tyr Gly Ala Ser Ser Arg Ala Thr Asp Ile Pro
65                  70                  75                  80 cac agg ttc agt ggc agt ggg tct ggg aca gac ttc act ctc acc atc     288
His Arg Phe Ser Gly Ser Gly Ser Gly Thr Asp Phe Thr Leu Thr Ile
                85                  90                  95 agc aga ctg gag cct gaa gat ttt gca gtg tac tac tgt cag caa tat     336
Ser Arg Leu Glu Pro Glu Asp Phe Ala Val Tyr Tyr Cys Gln Gln Tyr
            100                 105                 110 ggt acc tca gcc tta ctc act ttc ggc gga ggg acc aag gtg gag atc     384
Gly Thr Ser Ala Leu Leu Thr Phe Gly Gly Gly Thr Lys Val Glu Ile
        115                 120                 125 aaa cga act gtg gct gca cca tct gtc ttc atc ttc ccg cca tct         429
Lys Arg Thr Val Ala Ala Pro Ser Val Phe Ile Phe Pro Pro Ser
    130                 135                 140

<210> SEQ ID NO 4
<211> LENGTH: 143
<212> TYPE: PRT
<213> ORGANISM: Homo sapiens

<400> SEQUENCE: 4

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
```

```
            20                  25                  30
Leu Ser Pro Gly Glu Arg Ala Thr Leu Ser Cys Arg Ala Ser Gln Ser
        35                  40                  45

Val Ala Ser Ala Tyr Leu Ala Trp Tyr Gln Gln Lys Pro Gly Gln Ala
    50                  55                  60

Pro Arg Leu Leu Ile Tyr Gly Ala Ser Ser Arg Ala Thr Asp Ile Pro
65                  70                  75                  80

His Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Thr Ser Ala Leu Leu Thr Phe Gly Gly Gly Thr Lys Val Glu Ile
        115                 120                 125

Lys Arg Thr Val Ala Ala Pro Ser Val Phe Ile Phe Pro Pro Ser
    130                 135                 140
```

```
<210> SEQ ID NO 5
<211> LENGTH: 35
<212> TYPE: DNA
<213> ORGANISM: artificial sequence
<220> FEATURE:
<223> OTHER INFORMATION: Krix-1 heavy chain forward primer

<400> SEQUENCE: 5
cggggtaccc caccatggac tggacctgga ggatc                           35

<210> SEQ ID NO 6
<211> LENGTH: 40
<212> TYPE: DNA
<213> ORGANISM: artificial sequence
<220> FEATURE:
<223> OTHER INFORMATION: Krix-1 heavy chain reverse primer

<400> SEQUENCE: 6
tatggccgac gtcgactcat ttacccggag acagggagag                      40

<210> SEQ ID NO 7
<211> LENGTH: 34
<212> TYPE: DNA
<213> ORGANISM: artificial sequence
<220> FEATURE:
<223> OTHER INFORMATION: Krix-1 light chain forward primer

<400> SEQUENCE: 7
cccaagcttc caccatggaa accccagckc agct                            34

<210> SEQ ID NO 8
<211> LENGTH: 36
<212> TYPE: DNA
<213> ORGANISM: artificial sequence
<220> FEATURE:
<223> OTHER INFORMATION: Krix-1 light chain reverse primer

<400> SEQUENCE: 8
aaacagcctc tagactaaca ctctcccctg ttgaag                          36

<210> SEQ ID NO 9
<211> LENGTH: 46
<212> TYPE: DNA
<213> ORGANISM: artificial sequence
<220> FEATURE:
<223> OTHER INFORMATION: Krix-1 forward mutagenic primer Asn47Gln

<400> SEQUENCE: 9
```
cctgcaagac ctctggatac caattcaccg gctactctgc ttctgg            46

<210> SEQ ID NO 10
<211> LENGTH: 46
<212> TYPE: DNA
<213> ORGANISM: artificial sequence
<220> FEATURE:
<223> OTHER INFORMATION: Krix-1 reverse mutagenic primer Asn47Gln

<400> SEQUENCE: 10
ccagaagcag agtagccggt gaattggtat ccagaggtct tgcagg            46

<210> SEQ ID NO 11
<211> LENGTH: 37
<212> TYPE: DNA
<213> ORGANISM: artificial sequence
<220> FEATURE:
<223> OTHER INFORMATION: Krix-1 forward mutagenic primer Thr49Ala

<400> SEQUENCE: 11
cctctggata caacttcgct ggctactctg cttctgg                      37

<210> SEQ ID NO 12
<211> LENGTH: 37
<212> TYPE: DNA
<213> ORGANISM: artificial sequence
<220> FEATURE:
<223> OTHER INFORMATION: Krix-1 reverse mutagenic primer Thr49Ala

<400> SEQUENCE: 12
ccagaagcag agtagccagc gaagttgtat ccagagg                      37

<210> SEQ ID NO 13
<211> LENGTH: 46
<212> TYPE: DNA
<213> ORGANISM: artificial sequence
<220> FEATURE:
<223> OTHER INFORMATION: Krix-1 forward mutagenic primer Asn49Glu

<400> SEQUENCE: 13
cctgcaagac ctctggatac gagttcaccg gctactctgc ttctgg            46

<210> SEQ ID NO 14
<211> LENGTH: 46
<212> TYPE: DNA
<213> ORGANISM: artificial sequence
<220> FEATURE:
<223> OTHER INFORMATION: Krix-1 reverse mutagenic primer Asn49Glu

<400> SEQUENCE: 14
ccagaagcag agtagccggt gaactcgtat ccagaggtct tgcagg            46

<210> SEQ ID NO 15
<211> LENGTH: 46
<212> TYPE: DNA
<213> ORGANISM: artificial sequence
<220> FEATURE:
<223> OTHER INFORMATION: Krix-1 forward mutagenic primer Asn49Asp

<400> SEQUENCE: 15
cctgcaagac ctctggatac gacttcaccg gctactctgc ttctgg            46

<210> SEQ ID NO 16
<211> LENGTH: 46
<212> TYPE: DNA
<213> ORGANISM: artificial sequence

```
<220> FEATURE:
<223> OTHER INFORMATION: Krix-1 reverse mutagenic primer Asn49Asp

<400> SEQUENCE: 16
ccagaagcag agtagccggt gaagtcgtat ccagaggtct tgcagg            46

<210> SEQ ID NO 17
<211> LENGTH: 45
<212> TYPE: DNA
<213> ORGANISM: artificial sequence
<220> FEATURE:
<223> OTHER INFORMATION: scFv-KRIX-1VL forward primer

<400> SEQUENCE: 17
gtatctctcg agaaaagaga aattgtgttg acgcagtctc caggc             45

<210> SEQ ID NO 18
<211> LENGTH: 56
<212> TYPE: DNA
<213> ORGANISM: artificial sequence
<220> FEATURE:
<223> OTHER INFORMATION: scFv-KRIX-1VL reverse primer

<400> SEQUENCE: 18
cgccagagcc acctccgcct gaaccgcctc cacctcgttt gatctccacc ttggtc 56

<210> SEQ ID NO 19
<211> LENGTH: 56
<212> TYPE: DNA
<213> ORGANISM: artificial sequence
<220> FEATURE:
<223> OTHER INFORMATION: scFv-KRIX-1VH forward primer

<400> SEQUENCE: 19
caggcggagg tggctctggc ggtggcggat cgcaggtmca gctggtgcag tctggg 56

<210> SEQ ID NO 20
<211> LENGTH: 34
<212> TYPE: DNA
<213> ORGANISM: artificial sequence
<220> FEATURE:
<223> OTHER INFORMATION: scFv-KRIX-1VH reverse primer

<400> SEQUENCE: 20
gatctctaga tgaggagacg gtgaccaggg ttcc                         34

<210> SEQ ID NO 21
<211> LENGTH: 45
<212> TYPE: DNA
<213> ORGANISM: artificial sequence
<220> FEATURE:
<223> OTHER INFORMATION: scFv-KRIX-1VLVH with His(6)tag forward primer

<400> SEQUENCE: 21
gtatctctcg agaaaagaga aattgtgttg acgcagtctc caggc             45

<210> SEQ ID NO 22
<211> LENGTH: 40
<212> TYPE: DNA
<213> ORGANISM: artificial sequence
<220> FEATURE:
<223> OTHER INFORMATION: scFv-KRIX-1VLVH with His(6)tag reverse primer

<400> SEQUENCE: 22
catggtcgac tgaggagacg gtgaccaggg ttccccggcc                   40
```

<210> SEQ ID NO 23
<211> LENGTH: 46
<212> TYPE: DNA
<213> ORGANISM: artificial sequence
<220> FEATURE:
<223> OTHER INFORMATION: scFv- Asn47Gln KRIX-1VLVH(His) forward primer

<400> SEQUENCE: 23
cctgcaagac tctctggatac caattcaccg gctactctgc ttctgg     46

<210> SEQ ID NO 24
<211> LENGTH: 46
<212> TYPE: DNA
<213> ORGANISM: artificial sequence
<220> FEATURE:
<223> OTHER INFORMATION: scFv- Asn47Gln KRIX-1VLVH(His) reverse primer

<400> SEQUENCE: 24
ccagaagcag agtagccggt gaattggtat ccagaggtct tgcagg     46

<210> SEQ ID NO 25
<211> LENGTH: 867
<212> TYPE: DNA
<213> ORGANISM: Artificial sequence
<220> FEATURE:
<223> OTHER INFORMATION: scFv- Asn47Gln KRIX-1VLVH(His)
<220> FEATURE:
<221> NAME/KEY: CDS
<222> LOCATION: (1)..(867)

<400> SEQUENCE: 25

| atg | gaa | acc | cca | gcg | cag | ctt | ctc | ttc | ctc | ctg | cta | ctc | tgg | ctc | cca | 48 |
| Met | Glu | Thr | Pro | Ala | Gln | Leu | Leu | Phe | Leu | Leu | Leu | Leu | Trp | Leu | Pro | |
| 1   |     |     |     | 5   |     |     |     |     | 10  |     |     |     |     | 15  |     | |

| gat | acc | acc | gga | gaa | att | gtg | ttg | acg | cag | tct | cca | ggc | acc | ctg | tct | 96 |
| Asp | Thr | Thr | Gly | Glu | Ile | Val | Leu | Thr | Gln | Ser | Pro | Gly | Thr | Leu | Ser | |
|     |     |     | 20  |     |     |     |     | 25  |     |     |     |     | 30  |     |     | |

| ttg | tct | cca | ggg | gaa | aga | gcc | acc | ctc | tcc | tgc | agg | gcc | agt | cag | agt | 144 |
| Leu | Ser | Pro | Gly | Glu | Arg | Ala | Thr | Leu | Ser | Cys | Arg | Ala | Ser | Gln | Ser | |
|     |     | 35  |     |     |     |     | 40  |     |     |     |     | 45  |     |     |     | |

| gtt | gcc | agc | gcc | tac | tta | gcc | tgg | tac | cag | caa | aaa | cct | ggc | cag | gct | 192 |
| Val | Ala | Ser | Ala | Tyr | Leu | Ala | Trp | Tyr | Gln | Gln | Lys | Pro | Gly | Gln | Ala | |
|     | 50  |     |     |     |     | 55  |     |     |     |     | 60  |     |     |     |     | |

| ccc | agg | ctc | ctc | atc | tat | ggt | gca | tcc | agt | agg | gcc | acc | gac | atc | cca | 240 |
| Pro | Arg | Leu | Leu | Ile | Tyr | Gly | Ala | Ser | Ser | Arg | Ala | Thr | Asp | Ile | Pro | |
| 65  |     |     |     |     | 70  |     |     |     |     | 75  |     |     |     |     | 80  | |

| cac | agg | ttc | agt | ggc | agt | ggg | tct | ggg | aca | gac | ttc | act | ctc | acc | atc | 288 |
| His | Arg | Phe | Ser | Gly | Ser | Gly | Ser | Gly | Thr | Asp | Phe | Thr | Leu | Thr | Ile | |
|     |     |     |     | 85  |     |     |     |     | 90  |     |     |     |     | 95  |     | |

| agc | aga | ctg | gag | cct | gaa | gat | ttt | gca | gtg | tac | tac | tgt | cag | caa | tat | 336 |
| Ser | Arg | Leu | Glu | Pro | Glu | Asp | Phe | Ala | Val | Tyr | Tyr | Cys | Gln | Gln | Tyr | |
|     |     |     | 100 |     |     |     |     | 105 |     |     |     |     | 110 |     |     | |

| ggt | acc | tca | gcc | tta | ctc | act | ttc | ggc | gga | ggg | acc | aag | gtg | gag | atc | 384 |
| Gly | Thr | Ser | Ala | Leu | Leu | Thr | Phe | Gly | Gly | Gly | Thr | Lys | Val | Glu | Ile | |
|     |     | 115 |     |     |     |     | 120 |     |     |     |     | 125 |     |     |     | |

| aaa | cga | ggt | gga | ggc | ggt | tca | ggc | gga | ggt | ggc | tct | ggc | ggt | ggc | gga | 432 |
| Lys | Arg | Gly | Gly | Gly | Gly | Ser | Gly | Gly | Gly | Gly | Ser | Gly | Gly | Gly | Gly | |
|     | 130 |     |     |     |     | 135 |     |     |     |     | 140 |     |     |     |     | |

| tcg | cag | gta | cag | ctg | gtg | cag | tct | ggg | gct | gag | gtg | aag | aag | cct | ggg | 480 |
| Ser | Gln | Val | Gln | Leu | Val | Gln | Ser | Gly | Ala | Glu | Val | Lys | Lys | Pro | Gly | |
| 145 |     |     |     |     | 150 |     |     |     |     | 155 |     |     |     |     | 160 | |

| gcc | tca | gtg | aag | gtc | tcc | tgc | aag | acc | tct | gga | tac | caa | ttc | acc | ggc | 528 |
| Ala | Ser | Val | Lys | Val | Ser | Cys | Lys | Thr | Ser | Gly | Tyr | Gln | Phe | Thr | Gly | |
|     |     |     |     | 165 |     |     |     |     | 170 |     |     |     |     | 175 |     | |

```
tac tct gct tct gga cat atc ttc acc gcc tac tct gtg cac tgg gtg      576
Tyr Ser Ala Ser Gly His Ile Phe Thr Ala Tyr Ser Val His Trp Val
            180                 185                 190 cga cag gcc cct gga caa ggg ctt gag tgg atg gga agg atc aac cct      624
Arg Gln Ala Pro Gly Gln Gly Leu Glu Trp Met Gly Arg Ile Asn Pro
        195                 200                 205 aac agt ggt gcc aca gac tat gca cat aaa ttt cag ggc agg gtc acc      672
Asn Ser Gly Ala Thr Asp Tyr Ala His Lys Phe Gln Gly Arg Val Thr
    210                 215                 220 atg tcc agg gac acg tcc atc agc aca gcc tac atg gaa ctg agc agg      720
Met Ser Arg Asp Thr Ser Ile Ser Thr Ala Tyr Met Glu Leu Ser Arg
225                 230                 235                 240 ctg aca tct gac gac aca gcc atg tat tac tgt gcg aga gcc gac aac      768
Leu Thr Ser Asp Asp Thr Ala Met Tyr Tyr Cys Ala Arg Ala Asp Asn
                245                 250                 255 tat ttc gat att gtg act ggc tat act tct cat tac ttt gac tac tgg      816
Tyr Phe Asp Ile Val Thr Gly Tyr Thr Ser His Tyr Phe Asp Tyr Trp
            260                 265                 270 ggc cgg gga acc ctg gtc acc gtc tcc tca cat cat cat cat cat cat      864
Gly Arg Gly Thr Leu Val Thr Val Ser Ser His His His His His His
        275                 280                 285 tga                                                                   867

<210> SEQ ID NO 26
<211> LENGTH: 288
<212> TYPE: PRT
<213> ORGANISM: Artificial sequence
<220> FEATURE:
<223> OTHER INFORMATION: Synthetic Construct

<400> SEQUENCE: 26

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ala Ser Ala Tyr Leu Ala Trp Tyr Gln Gln Lys Pro Gly Gln Ala
    50                  55                  60

Pro Arg Leu Leu Ile Tyr Gly Ala Ser Ser Arg Ala Thr Asp Ile Pro
65                  70                  75                  80

His Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Thr Ser Ala Leu Leu Thr Phe Gly Gly Gly Thr Lys Val Glu Ile
        115                 120                 125

Lys Arg Gly Gly Gly Gly Ser Gly Gly Gly Ser Gly Gly Gly Gly
    130                 135                 140

Ser Gln Val Gln Leu Val Gln Ser Gly Ala Glu Val Lys Lys Pro Gly
145                 150                 155                 160

Ala Ser Val Lys Val Ser Cys Lys Thr Ser Gly Tyr Gln Phe Thr Gly
                165                 170                 175

Tyr Ser Ala Ser Gly His Ile Phe Thr Ala Tyr Ser Val His Trp Val
            180                 185                 190

Arg Gln Ala Pro Gly Gln Gly Leu Glu Trp Met Gly Arg Ile Asn Pro
        195                 200                 205

Asn Ser Gly Ala Thr Asp Tyr Ala His Lys Phe Gln Gly Arg Val Thr
```

```
            210                 215                 220
Met Ser Arg Asp Thr Ser Ile Ser Thr Ala Tyr Met Glu Leu Ser Arg
225                 230                 235                 240

Leu Thr Ser Asp Asp Thr Ala Met Tyr Tyr Cys Ala Arg Ala Asp Asn
                245                 250                 255

Tyr Phe Asp Ile Val Thr Gly Tyr Thr Ser His Tyr Phe Asp Tyr Trp
                260                 265                 270

Gly Arg Gly Thr Leu Val Thr Val Ser Ser His His His His His
            275                 280                 285

<210> SEQ ID NO 27
<211> LENGTH: 40
<212> TYPE: DNA
<213> ORGANISM: artificial sequence
<220> FEATURE:
<223> OTHER INFORMATION: CHO-scFvKRIX-1VLVH(His) forward primer

<400> SEQUENCE: 27
cccaagcttg ccgccaccat ggaaacccca gckcagcttc                         40

<210> SEQ ID NO 28
<211> LENGTH: 54
<212> TYPE: DNA
<213> ORGANISM: artificial sequence
<220> FEATURE:
<223> OTHER INFORMATION: CHO-scFvKRIX-1VLVH(His) reverse primer

<400> SEQUENCE: 28
ccggaattct caatgatgat gatgatgatg tgaggagacg gtgaccaggg ttcc         54

<210> SEQ ID NO 29
<211> LENGTH: 450
<212> TYPE: DNA
<213> ORGANISM: Homo sapiens
<220> FEATURE:
<221> NAME/KEY: CDS
<222> LOCATION: (1)..(450)
<223> OTHER INFORMATION: RHD5 heavy chain variable region
<220> FEATURE:
<221> NAME/KEY: misc_feature
<222> LOCATION: (1)..(60)
<223> OTHER INFORMATION: nucleotide sequence encoding leader peptide
<220> FEATURE:
<221> NAME/KEY: misc_feature
<222> LOCATION: (133)..(162)
<223> OTHER INFORMATION: nucleotide sequence encoding CDR1
<220> FEATURE:
<221> NAME/KEY: misc_feature
<222> LOCATION: (205)..(255)
<223> OTHER INFORMATION: nucleotide sequence encoding CDR2
<220> FEATURE:
<221> NAME/KEY: misc_feature
<222> LOCATION: (352)..(384)
<223> OTHER INFORMATION: nucleotide sequence encoding CDR3

<400> SEQUENCE: 29 atg gac tgg acc tgg agg ttc ctc ttt gtg gtg gca gca gct gca ggt    48
Met Asp Trp Thr Trp Arg Phe Leu Phe Val Val Ala Ala Ala Ala Gly
1               5                   10                  15 gtc cag tcc cag gtg cag ctg gtg cag tct ggg gct gag gtg aag aag    96
Val Gln Ser Gln Val Gln Leu Val Gln Ser Gly Ala Glu Val Lys Lys
            20                  25                  30 ccc ggg tcg tcg gtg atg gtc tcc tgc aag gct tct gga ggc acc ttc   144
Pro Gly Ser Ser Val Met Val Ser Cys Lys Ala Ser Gly Gly Thr Phe
        35                  40                  45 agc agc ttt ggt atc agc tgg gtg cga cag gcc cct gga caa ggg ctt   192
Ser Ser Phe Gly Ile Ser Trp Val Arg Gln Ala Pro Gly Gln Gly Leu
```

```
                    50                    55                    60
gag tgg gtg gga ggg atc atc cct atc ttt ggt aca gca aac acc gca      240
Glu Trp Val Gly Gly Ile Ile Pro Ile Phe Gly Thr Ala Asn Thr Ala
 65                  70                  75                  80 cgg aac ttc cag aat aga gtc acc att acc gcg gac gaa ttc acg agc      288
Arg Asn Phe Gln Asn Arg Val Thr Ile Thr Ala Asp Glu Phe Thr Ser
                 85                  90                  95 aca gcc tac ata cga ctg agg agc ctg aga tct gaa gat acg gcc gtg      336
Thr Ala Tyr Ile Arg Leu Arg Ser Leu Arg Ser Glu Asp Thr Ala Val
            100                 105                 110 tat tac tgt gtc ggc ggt cga gat gcc tac agc ttt gat ggt ttt gat      384
Tyr Tyr Cys Val Gly Gly Arg Asp Ala Tyr Ser Phe Asp Gly Phe Asp
        115                 120                 125 gtc tgg ggc caa ggg aca atg gtc acc gtc tct tca gcc tcc acc aag      432
Val Trp Gly Gln Gly Thr Met Val Thr Val Ser Ser Ala Ser Thr Lys
130                 135                 140 ggc cca tcg gtc ttc ccc                                              450
Gly Pro Ser Val Phe Pro
145                 150

<210> SEQ ID NO 30
<211> LENGTH: 150
<212> TYPE: PRT
<213> ORGANISM: Homo sapiens

<400> SEQUENCE: 30

Met Asp Trp Thr Trp Arg Phe Leu Phe Val Val Ala Ala Ala Ala Gly
 1               5                  10                  15

Val Gln Ser Gln Val Gln Leu Val Gln Ser Gly Ala Glu Val Lys Lys
            20                  25                  30

Pro Gly Ser Ser Val Met Val Ser Cys Lys Ala Ser Gly Gly Thr Phe
        35                  40                  45

Ser Ser Phe Gly Ile Ser Trp Val Arg Gln Ala Pro Gly Gln Gly Leu
    50                  55                  60

Glu Trp Val Gly Gly Ile Ile Pro Ile Phe Gly Thr Ala Asn Thr Ala
 65                  70                  75                  80

Arg Asn Phe Gln Asn Arg Val Thr Ile Thr Ala Asp Glu Phe Thr Ser
                 85                  90                  95

Thr Ala Tyr Ile Arg Leu Arg Ser Leu Arg Ser Glu Asp Thr Ala Val
            100                 105                 110

Tyr Tyr Cys Val Gly Gly Arg Asp Ala Tyr Ser Phe Asp Gly Phe Asp
        115                 120                 125

Val Trp Gly Gln Gly Thr Met Val Thr Val Ser Ser Ala Ser Thr Lys
130                 135                 140

Gly Pro Ser Val Phe Pro
145                 150

<210> SEQ ID NO 31
<211> LENGTH: 420
<212> TYPE: DNA
<213> ORGANISM: Homo sapiens
<220> FEATURE:
<221> NAME/KEY: CDS
<222> LOCATION: (1)..(420)
<223> OTHER INFORMATION: RHD5 light chain variable region
<220> FEATURE:
<221> NAME/KEY: misc_feature
<222> LOCATION: (1)..(60)
<223> OTHER INFORMATION: nucleotide sequence encoding leader peptide
<220> FEATURE:
<221> NAME/KEY: misc_feature
<222> LOCATION: (124)..(156)
```

<223> OTHER INFORMATION: nucleotide sequence encoding CDR1
<220> FEATURE:
<221> NAME/KEY: misc_feature
<222> LOCATION: (202)..(222)
<223> OTHER INFORMATION: nucleotide sequence encoding CDR2
<220> FEATURE:
<221> NAME/KEY: misc_feature
<222> LOCATION: (316)..(348)
<223> OTHER INFORMATION: nucleotide sequence encoding CDR3

<400> SEQUENCE: 31

| atg | gca | tgg | atc | cct | ctc | ttc | ctc | ggc | gtc | ctt | gtt | tac | tgc | aca | gga | 48 |
|---|---|---|---|---|---|---|---|---|---|---|---|---|---|---|---|---|
| Met | Ala | Trp | Ile | Pro | Leu | Phe | Leu | Gly | Val | Leu | Val | Tyr | Cys | Thr | Gly | |
| 1 | | | | 5 | | | | | 10 | | | | | 15 | | |

| tcc | gtg | gcc | tcc | tct | ggg | ctg | act | cag | cca | cac | tca | gtg | tcc | gtg | tcc | 96 |
|---|---|---|---|---|---|---|---|---|---|---|---|---|---|---|---|---|
| Ser | Val | Ala | Ser | Ser | Gly | Leu | Thr | Gln | Pro | His | Ser | Val | Ser | Val | Ser | |
| | | | 20 | | | | | 25 | | | | | 30 | | | |

| cca | gga | cag | aca | gcc | aac | atc | acc | tgc | tct | aga | gat | aag | ttg | ggt | cat | 144 |
|---|---|---|---|---|---|---|---|---|---|---|---|---|---|---|---|---|
| Pro | Gly | Gln | Thr | Ala | Asn | Ile | Thr | Cys | Ser | Arg | Asp | Lys | Leu | Gly | His | |
| | | 35 | | | | | 40 | | | | | 45 | | | | |

| aaa | ttt | gct | tcc | tgg | tat | caa | cag | aag | cca | ggc | cag | tcc | cct | gct | ctt | 192 |
|---|---|---|---|---|---|---|---|---|---|---|---|---|---|---|---|---|
| Lys | Phe | Ala | Ser | Trp | Tyr | Gln | Gln | Lys | Pro | Gly | Gln | Ser | Pro | Ala | Leu | |
| | 50 | | | | | 55 | | | | | 60 | | | | | |

| ctc | atc | tat | caa | gac | agc | aag | cgg | ccc | tca | ggg | atc | cct | gag | cga | ttc | 240 |
|---|---|---|---|---|---|---|---|---|---|---|---|---|---|---|---|---|
| Leu | Ile | Tyr | Gln | Asp | Ser | Lys | Arg | Pro | Ser | Gly | Ile | Pro | Glu | Arg | Phe | |
| 65 | | | | | 70 | | | | | 75 | | | | | 80 | |

| tct | ggc | tcc | aac | tct | ggg | aac | aca | gcc | act | ctg | acc | atc | agc | ggg | acc | 288 |
|---|---|---|---|---|---|---|---|---|---|---|---|---|---|---|---|---|
| Ser | Gly | Ser | Asn | Ser | Gly | Asn | Thr | Ala | Thr | Leu | Thr | Ile | Ser | Gly | Thr | |
| | | | | 85 | | | | | 90 | | | | | 95 | | |

| cag | gct | atg | gat | gag | gct | gac | tat | tac | tgt | cag | gcg | tgg | gac | aac | acc | 336 |
|---|---|---|---|---|---|---|---|---|---|---|---|---|---|---|---|---|
| Gln | Ala | Met | Asp | Glu | Ala | Asp | Tyr | Tyr | Cys | Gln | Ala | Trp | Asp | Asn | Thr | |
| | | | 100 | | | | | 105 | | | | | 110 | | | |

| act | gcc | gta | ttc | ggc | gga | ggg | acc | aag | ttg | aca | gtc | cta | agt | cag | ccc | 384 |
|---|---|---|---|---|---|---|---|---|---|---|---|---|---|---|---|---|
| Thr | Ala | Val | Phe | Gly | Gly | Gly | Thr | Lys | Leu | Thr | Val | Leu | Ser | Gln | Pro | |
| | | | 115 | | | | | 120 | | | | | 125 | | | |

| aag | gct | gcc | ccc | tcg | gtc | act | ctg | ttc | ccg | ccc | tcc | | | | | 420 |
|---|---|---|---|---|---|---|---|---|---|---|---|---|---|---|---|---|
| Lys | Ala | Ala | Pro | Ser | Val | Thr | Leu | Phe | Pro | Pro | Ser | | | | | |
| | 130 | | | | | 135 | | | | | 140 | | | | | |

<210> SEQ ID NO 32
<211> LENGTH: 140
<212> TYPE: PRT
<213> ORGANISM: Homo sapiens

<400> SEQUENCE: 32

Met Ala Trp Ile Pro Leu Phe Leu Gly Val Leu Val Tyr Cys Thr Gly
1               5                   10                  15

Ser Val Ala Ser Ser Gly Leu Thr Gln Pro His Ser Val Ser Val Ser
            20                  25                  30

Pro Gly Gln Thr Ala Asn Ile Thr Cys Ser Arg Asp Lys Leu Gly His
        35                  40                  45

Lys Phe Ala Ser Trp Tyr Gln Gln Lys Pro Gly Gln Ser Pro Ala Leu
    50                  55                  60

Leu Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Asn Thr
            100                 105                 110

Thr Ala Val Phe Gly Gly Gly Thr Lys Leu Thr Val Leu Ser Gln Pro
        115                 120                 125

```
Lys Ala Ala Pro Ser Val Thr Leu Phe Pro Pro Ser
        130                 135                 140

<210> SEQ ID NO 33
<211> LENGTH: 20
<212> TYPE: PRT
<213> ORGANISM: Artificial
<220> FEATURE:
<223> OTHER INFORMATION: KRIX-1 heavy chain CDR1

<400> SEQUENCE: 33

Gly Tyr Asn Phe Thr Gly Tyr Ser Ala Ser Gly His Ile Phe Thr Ala
1               5                   10                  15

Tyr Ser Val His
            20

<210> SEQ ID NO 34
<211> LENGTH: 17
<212> TYPE: PRT
<213> ORGANISM: Artificial
<220> FEATURE:
<223> OTHER INFORMATION: KRIX-1 heavy chain CDR2

<400> SEQUENCE: 34

Arg Ile Asn Pro Asn Ser Gly Ala Thr Asp Tyr Ala His Lys Phe Gln
1               5                   10                  15

Gly

<210> SEQ ID NO 35
<211> LENGTH: 18
<212> TYPE: PRT
<213> ORGANISM: Artificial sequence
<220> FEATURE:
<223> OTHER INFORMATION: KRIX-1 heavy chain CDR3

<400> SEQUENCE: 35

Ala Asp Asn Tyr Phe Asp Ile Val Thr Gly Tyr Thr Ser His Tyr Phe
1               5                   10                  15

Asp Tyr

<210> SEQ ID NO 36
<211> LENGTH: 12
<212> TYPE: PRT
<213> ORGANISM: Artificial sequence
<220> FEATURE:
<223> OTHER INFORMATION: KRIX-1 light chain CDR1

<400> SEQUENCE: 36

Arg Ala Ser Gln Ser Val Ala Ser Ala Tyr Leu Ala
1               5                   10

<210> SEQ ID NO 37
<211> LENGTH: 7
<212> TYPE: PRT
<213> ORGANISM: Artificial sequence
<220> FEATURE:
<223> OTHER INFORMATION: KRIX-1 light chain CDR2

<400> SEQUENCE: 37

Gly Ala Ser Ser Arg Ala Thr
1               5

<210> SEQ ID NO 38
<211> LENGTH: 10
<212> TYPE: PRT
<213> ORGANISM: Artificial sequence
```

```
<220> FEATURE:
<223> OTHER INFORMATION: KRIX-1 light chain CDR3

<400> SEQUENCE: 38

Gln Gln Tyr Gly Thr Ser Ala Leu Leu Thr
1               5                   10

<210> SEQ ID NO 39
<211> LENGTH: 10
<212> TYPE: PRT
<213> ORGANISM: Artificial sequence
<220> FEATURE:
<223> OTHER INFORMATION: RHD5 heavy chain CDR1

<400> SEQUENCE: 39

Gly Gly Thr Phe Ser Ser Phe Gly Ile Ser
1               5                   10

<210> SEQ ID NO 40
<211> LENGTH: 18
<212> TYPE: PRT
<213> ORGANISM: Artificial sequence
<220> FEATURE:
<223> OTHER INFORMATION: RHD5 heavy chain CDR2

<400> SEQUENCE: 40

Gly Gly Ile Ile Pro Ile Phe Gly Thr Ala Asn Thr Ala Arg Asn Phe
1               5                   10                  15

Gln Asn

<210> SEQ ID NO 41
<211> LENGTH: 11
<212> TYPE: PRT
<213> ORGANISM: Artificial sequence
<220> FEATURE:
<223> OTHER INFORMATION: RHD5 heavy chain CDR3

<400> SEQUENCE: 41

Gly Arg Asp Ala Tyr Ser Phe Asp Gly Phe Asp
1               5                   10

<210> SEQ ID NO 42
<211> LENGTH: 11
<212> TYPE: PRT
<213> ORGANISM: Artificial sequence
<220> FEATURE:
<223> OTHER INFORMATION: RHD5 light chain CDR1

<400> SEQUENCE: 42

Ser Arg Asp Lys Leu Gly His Lys Phe Ala Ser
1               5                   10

<210> SEQ ID NO 43
<211> LENGTH: 7
<212> TYPE: PRT
<213> ORGANISM: Artificial sequence
<220> FEATURE:
<223> OTHER INFORMATION: RHD5 light chain CDR2

<400> SEQUENCE: 43

Gln Asp Ser Lys Arg Pro Ser
1               5

<210> SEQ ID NO 44
<211> LENGTH: 11
<212> TYPE: PRT
<213> ORGANISM: Artificial sequence
```

-continued

```
<220> FEATURE:
<223> OTHER INFORMATION: RHD5 light chain CDR3

<400> SEQUENCE: 44

Cys Gln Ala Trp Asp Asn Thr Thr Ala Val Phe
1               5                   10

<210> SEQ ID NO 45
<211> LENGTH: 450
<212> TYPE: DNA
<213> ORGANISM: Homo sapiens
<220> FEATURE:
<221> NAME/KEY: CDS
<222> LOCATION: (1)..(450)
<223> OTHER INFORMATION: BO 2C11 variable heavy chain
<220> FEATURE:
<221> NAME/KEY: misc_feature
<222> LOCATION: (130)..(159)
<223> OTHER INFORMATION: sequence encoding CDR1
<220> FEATURE:
<221> NAME/KEY: misc_feature
<222> LOCATION: (202)..(258)
<223> OTHER INFORMATION: sequence encoding CDR2
<220> FEATURE:
<221> NAME/KEY: misc_feature
<222> LOCATION: (343)..(375)
<223> OTHER INFORMATION: sequence encoding CDR3

<400> SEQUENCE: 45 atg gac tgg acc tgg agg atc ctc ttc ttg gtg gca gca gct aca ggc      48
Met Asp Trp Thr Trp Arg Ile Leu Phe Leu Val Ala Ala Ala Thr Gly
1               5                   10                  15 acc cac gcc cag gtc caa ctg gta cag tct ggg gct gag gtg aag aag      96
Thr His Ala Gln Val Gln Leu Val Gln Ser Gly Ala Glu Val Lys Lys
                20                  25                  30 cct ggg gcc tca gtg aag gtc tcc tgc aag gtt tcc gga tac acc ctc     144
Pro Gly Ala Ser Val Lys Val Ser Cys Lys Val Ser Gly Tyr Thr Leu
            35                  40                  45 act gaa tta ccc gtg cac tgg gtc gga cag gct cct gga aaa ggg ctt     192
Thr Glu Leu Pro Val His Trp Val Gly Gln Ala Pro Gly Lys Gly Leu
        50                  55                  60 gag tgg gtg gga agt ttt gat cct gaa agt gga gaa tca atc tac gca     240
Glu Trp Val Gly Ser Phe Asp Pro Glu Ser Gly Glu Ser Ile Tyr Ala
65                  70                  75                  80 cgg gag ttc cag ggc agc gtc acc atg acc gcg gac aca tct aca gac     288
Arg Glu Phe Gln Gly Ser Val Thr Met Thr Ala Asp Thr Ser Thr Asp
                85                  90                  95 ata gcc tac atg gag ctg agc agc ctg aga tct gac gac acg gcc gtg     336
Ile Ala Tyr Met Glu Leu Ser Ser Leu Arg Ser Asp Asp Thr Ala Val
            100                 105                 110 tat tac tgt gca gtc cct gac cct gat gct ttt gat atc tgg ggc caa     384
Tyr Tyr Cys Ala Val Pro Asp Pro Asp Ala Phe Asp Ile Trp Gly Gln
        115                 120                 125 ggg aca atg gtc acc gtc tct tca gcc tcc acc aag ggc cca tcg gtc     432
Gly Thr Met Val Thr Val Ser Ser Ala Ser Thr Lys Gly Pro Ser Val
    130                 135                 140 ttc ccc ctg gga tcc cgt                                              450
Phe Pro Leu Gly Ser Arg
145                 150

<210> SEQ ID NO 46
<211> LENGTH: 150
<212> TYPE: PRT
<213> ORGANISM: Homo sapiens

<400> SEQUENCE: 46
```

```
Met Asp Trp Thr Trp Arg Ile Leu Phe Leu Val Ala Ala Thr Gly
1               5                   10                  15

Thr His Ala Gln Val Gln Leu Val Gln Ser Gly Ala Glu Val Lys Lys
                20                  25                  30

Pro Gly Ala Ser Val Lys Val Ser Cys Lys Val Ser Gly Tyr Thr Leu
            35                  40                  45

Thr Glu Leu Pro Val His Trp Val Gly Gln Ala Pro Gly Lys Gly Leu
    50                  55                  60

Glu Trp Val Gly Ser Phe Asp Pro Glu Ser Gly Glu Ser Ile Tyr Ala
65                  70                  75                  80

Arg Glu Phe Gln Gly Ser Val Thr Met Thr Ala Asp Thr Ser Thr Asp
                85                  90                  95

Ile Ala Tyr Met Glu Leu Ser Ser Leu Arg Ser Asp Asp Thr Ala Val
            100                 105                 110

Tyr Tyr Cys Ala Val Pro Asp Pro Asp Ala Phe Asp Ile Trp Gly Gln
            115                 120                 125

Gly Thr Met Val Thr Val Ser Ser Ala Ser Thr Lys Gly Pro Ser Val
130                 135                 140

Phe Pro Leu Gly Ser Arg
145             150
```

<210> SEQ ID NO 47
<211> LENGTH: 426
<212> TYPE: DNA
<213> ORGANISM: Homo sapiens
<220> FEATURE:
<221> NAME/KEY: CDS
<222> LOCATION: (1)..(426)
<223> OTHER INFORMATION: BO2C11 variable light chain
<220> FEATURE:
<221> NAME/KEY: misc_feature
<222> LOCATION: (127)..(162)
<223> OTHER INFORMATION: sequence encoding CDR1
<220> FEATURE:
<221> NAME/KEY: misc_feature
<222> LOCATION: (205)..(225)
<223> OTHER INFORMATION: sequence encoding CDR2
<220> FEATURE:
<221> NAME/KEY: misc_feature
<222> LOCATION: (325)..(351)
<223> OTHER INFORMATION: sequence encoding CDR3

<400> SEQUENCE: 47

```
atg gaa acc cca gct cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gcg ttg acg cag tct cca ggc acc ctg tct      96
Asp Thr Thr Gly Glu Ile Ala Leu Thr Gln Ser Pro Gly Thr Leu Ser
                20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
            35                  40                  45 ttt agc agc agc tac tta gcc tgg tat cag cag aaa cct ggc cag gct     192
Phe Ser Ser Ser Tyr Leu Ala Trp Tyr Gln Gln Lys Pro Gly Gln Ala
    50                  55                  60 ccc agg ctc ctc atc tat ggt gca tcc acc agg gcc act ggc atc cca     240
Pro Arg Leu Leu Ile Tyr Gly Ala Ser Thr Arg Ala Thr Gly Ile Pro
65                  70                  75                  80 gac agg ttc agt ggc agt ggg tct ggg aca gac ttc act ctc acc atc     288
Asp Arg Phe Ser Gly Ser Gly Ser Gly Thr Asp Phe Thr Leu Thr Ile
                85                  90                  95 agc aga ctg gag cct gaa gat ttt gca gtg tat tac tgt cag aag tat     336
Ser Arg Leu Glu Pro Glu Asp Phe Ala Val Tyr Tyr Cys Gln Lys Tyr
```

-continued

```
            100                 105                 110 ggt acg tca gcg atc acc ttc ggg caa ggg aca cga ctg gag att aaa      384
Gly Thr Ser Ala Ile Thr Phe Gly Gln Gly Thr Arg Leu Glu Ile Lys
        115                 120                 125 gga act gtg gct gca cca tct gtc ttc atc ttc ccg cca tct              426
Gly Thr Val Ala Ala Pro Ser Val Phe Ile Phe Pro Pro Ser
    130                 135                 140

<210> SEQ ID NO 48
<211> LENGTH: 142
<212> TYPE: PRT
<213> ORGANISM: Homo sapiens

<400> SEQUENCE: 48

Met Glu Thr Pro Ala Gln Leu Leu Phe Leu Leu Leu Leu Trp Leu Pro
1               5                   10                  15

Asp Thr Thr Gly Glu Ile Ala Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Phe Ser Ser Ser Tyr Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Lys Tyr
            100                 105                 110

Gly Thr Ser Ala Ile Thr Phe Gly Gln Gly Thr Arg Leu Glu Ile Lys
        115                 120                 125

Gly Thr Val Ala Ala Pro Ser Val Phe Ile Phe Pro Pro Ser
    130                 135                 140
```